US011680044B2

(12) United States Patent
Feilding-Mellen et al.

(10) Patent No.: US 11,680,044 B2
(45) Date of Patent: *Jun. 20, 2023

(54) PHARMACEUTICAL COMPOSITION COMPRISING 5-METHOXY-N,N-DIMETHYLTRYPTAMINE

(71) Applicant: Beckley Psytech Limited, Oxford (GB)

(72) Inventors: Cosmo Feilding-Mellen, Oxford (GB); Timothy Mason, Oxford (GB)

(73) Assignee: Beckley Psytech Limited, Oxford (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/935,256

(22) Filed: Sep. 26, 2022

(65) Prior Publication Data

US 2023/0031944 A1    Feb. 2, 2023

Related U.S. Application Data

(63) Continuation of application No. 17/660,981, filed on Apr. 27, 2022, now Pat. No. 11,518,743, which is a continuation of application No. PCT/GB2021/051476, filed on Jun. 14, 2021.

(30) Foreign Application Priority Data

| Jun. 12, 2020 | (GB) | 2008961 |
| Jun. 12, 2020 | (GB) | 2008964 |
| Jun. 12, 2020 | (GB) | 2008968 |
| Dec. 7, 2020 | (GB) | 2019241 |
| Feb. 5, 2021 | (GB) | 2101634 |
| Feb. 5, 2021 | (GB) | 2101640 |
| Feb. 15, 2021 | (GB) | 2102095 |
| Feb. 15, 2021 | (GB) | 2102100 |
| Apr. 8, 2021 | (GB) | 2105047 |
| Apr. 8, 2021 | (GB) | 2105049 |
| Apr. 16, 2021 | (GB) | 2105462 |

(51) Int. Cl.
  *C07D 209/16* (2006.01)
  *A61P 25/24* (2006.01)

(52) U.S. Cl.
  CPC .......... *C07D 209/16* (2013.01); *A61P 25/24* (2018.01); *C07B 2200/13* (2013.01)

(58) Field of Classification Search
  CPC .................................................. C07D 209/16
  See application file for complete search history.

(56) References Cited

U.S. PATENT DOCUMENTS

| 2,774,763 | A | 12/1956 | Garbrecht |
| 2,997,470 | A | 8/1961 | Pioch |
| 3,078,214 | A | 2/1963 | Hofmann et al. |
| 3,224,945 | A | 12/1965 | Tyler, Jr. |
| 2012/0108510 | A1 | 5/2012 | Young et al. |
| 2017/0348303 | A1 | 12/2017 | Bosse et al. |
| 2018/0021326 | A1 | 1/2018 | Stamets |
| 2018/0147142 | A1 | 5/2018 | Knight |
| 2020/0179349 | A1 | 6/2020 | Yun et al. |
| 2020/0187777 | A1 | 6/2020 | Luderer et al. |
| 2021/0058956 | A1 | 2/2021 | Chatterjee et al. |
| 2021/0069170 | A1 | 3/2021 | Stamets |
| 2021/0085671 | A1 | 3/2021 | Chadeayne |
| 2021/0322743 | A1 | 10/2021 | Rinti et al. |

FOREIGN PATENT DOCUMENTS

| CH | 578565 | A5 | 8/1976 |
| CN | 103816150 | A | 5/2014 |
| CN | 113288883 | A | 8/2021 |
| DE | 2617738 | A1 | 11/1976 |
| EP | 0026899 | A1 | 4/1981 |
| EP | 3868364 | A1 | 8/2021 |
| GB | 981192 | A | 1/1965 |
| GB | 1410349 | A | 10/1975 |
| GB | 1584464 | A | 2/1981 |
| GB | 2596884 | A | 1/2022 |
| WO | 0115677 | A2 | 3/2001 |
| WO | 0115677 | A3 | 3/2001 |
| WO | 0238142 | A2 | 5/2002 |
| WO | 2004000849 | A2 | 12/2003 |
| WO | 2008003028 | A2 | 1/2008 |
| WO | 2010054202 | A2 | 5/2010 |
| WO | 2013063492 | A1 | 5/2013 |
| WO | 2018195455 | A1 | 10/2018 |
| WO | 2019073379 | A1 | 4/2019 |
| WO | 2019081764 | A1 | 5/2019 |
| WO | 2019173797 | A1 | 9/2019 |
| WO | 2019246532 | A1 | 12/2019 |
| WO | 2020169850 | A1 | 8/2020 |
| WO | 2020169851 | A1 | 8/2020 |
| WO | 2020176597 | A1 | 9/2020 |
| WO | 2020181194 | A1 | 9/2020 |
| WO | 2020212951 | A1 | 10/2020 |
| WO | 2021003467 | A1 | 1/2021 |
| WO | 2021041407 | A1 | 3/2021 |
| WO | 2021089872 | A1 | 5/2021 |
| WO | 2021209815 | A1 | 10/2021 |
| WO | 2021222885 | A1 | 11/2021 |
| WO | 2021225796 | A1 | 11/2021 |
| WO | 2021250434 | A1 | 12/2021 |

OTHER PUBLICATIONS

International Search Report in International Application No. PCT/GB2021/051475, dated Sep. 16, 2021 (3 pages).
International Search Report in International Application No. PCT/GB2021/051476, dated Sep. 15, 2021 (5 pages).

(Continued)

*Primary Examiner* — Shawquia Jackson
(74) *Attorney, Agent, or Firm* — Bookoff McAndrews, PLLC

(57) ABSTRACT

An intranasal composition comprising a dosage amount of 50-150 mg/ml 5-methoxy-N,N-dimethyltryptamine (5MeODMT) in a liquid medium, wherein the 5MeODMT is formulated as the chloride salt of 5MeODMT (5MeODMT hydrochloride) and wherein the 5MeODMT hydrochloride is crystalline and characterised by one or more of: peaks in an XRPD diffractogram; an endothermic event in a DSC thermograph; an onset of decomposition in a TGA thermograph; and a DVS isotherm profile.

19 Claims, 16 Drawing Sheets

(56) References Cited

OTHER PUBLICATIONS

Uthaug, M.V et al., "Prospective examination of synthetic 5-methoxy-N,N-dimethyltryptamine inhalation: effects on IL-6, cortisol levels, affect, and non-judgment," Psychopharmacology, vol. 237, pp. 773-785 (2020).
Database Registry; Chemical Abstracts Service: Columbus, OH; Chemical Name: 1H-Indole-3-ethanamine, 5-methoxy-N,N dimethyl-, benzoate (1:1); RN 282103-25-7; ED Aug. 1, 2000 (1 page).
Benington, F. et al., "Synthesis of O- and N-Methylated Derivatives of 5-Hydroxytryptamine," The Journal of Organic Chemistry, vol. 23, pp. 1977-1979 (1958).
Falkenberg, G. et al., "The Crystal and Molecular Structure of 5-Methoxy-(N,N)-dimethyltryptamine Hydrochloride," Acta Crystallographica Section B, vol. 27, pp. 411-418 (1971).
Roseman, L. et al., "Increased amygdala responses to emotional faces after psilocybin treatment-resistant depression," Neuropharmacology, vol. 142, pp. 263-269 (2018).
Griffiths, R.R. et al., "Psilocybin produces substantial and sustained decreases in depression and anxiety in patients with life-threatening cancer: A randomized double-blind trial," Journal of Psychopharmacology, vol. 30, pp. 1181-1197 (2016).
Carhart-Harris, R.L. et al., "Psilocybin with psychological support for treatment-resistant depression: six-month follow-up," Psychopharmacology, vol. 235, pp. 399-408 (2018).
Monte, A.P. et al., "Stereoselective LSD-like Activity in a Series of d-Lysergic Acid Amides of (R) and (S)-2-Aminoalkanes," Journal of Medicinal Chemistry, vol. 38, pp. 958-966 (1995).
Ishii, H et al., "Studies on Lysergic Acid Diethylamide and Related Compounds. Part 8. Structural Identification of New Metabolites of Lysergic Acid Diethylamide obtained by Microbial Transformation using Streptomyces roseochromogenes," Journal of the Chemical Society, Perkin Transactions 1: Organic & Bio-organic Chemistry, vol. 4, pp. 902-905 (1980).
Nakahara, Y. et al., "Studies on Lysergic Acid Diethylamide and Related Compounds. III. Improvement of Amidation of Lysergic Acid," Yakugaku Zasshi, vol. 94, pp. 407-412 (1974).
Huang, X. et al., "Drug Discrimination and Receptor Binding Studies of N-Isopropyl Lysergamide Derivatives," Pharmacology Biochemistry and Behavior, vol. 47, pp. 667-673 (1994).
Ishii, H. et al., "Studies on Lysergic Acid Diethylamide and Related Compounds. IX. Microbial Transformation of Amides Related to Lysergic Acid Diethylamide by Streptomyces roseochromogenes," Chemical & Pharmaceutical Bulletin, vol. 27, pp. 3029-3038 (1979).
Johnson, F.N. et al., "Emetic Activity of Reduced Lysergamides," Journal of Medicinal Chemistry, vol. 16, pp. 532-537 (1973).
Vangveravong, S. et al., "Synthesis and Serotonin Receptor Affinities of a Series of trans-2-(Indol-3-yl) cyclopropylamine Derivatives," Journal of Medicinal Chemistry, vol. 41, pp. 4995-5001 (1998).
Schneller, S.W. et al., "Synthesis of 4-Amino-1H-pyrrolo[2,3-b]pyridine (1,7-Dideazaadenine) and 1H-Pyrrolo[2,3-b]pyridin-4-ol (1,7-Dideazahypoxanthine)," The Journal of Organic Chemistry A, vol. 45, pp. 4045-4048 (1980).
Singh, S.K. et al., "An ab Initio Study of the Effect of Substituents on the n→π Interactions between 7-Azaindole and 2,6 Difluorosubstituted Pyridines," The Journal of Physical Chemistry A, vol. 120, pp. 6258-6269 (2016).
Monson, C.M. et al., "MDMA-facilitated cognitive-behavioural conjoint therapy for posttraumatic stress disorder: an uncontrolled trial," European Journal of Psychotraumatology, vol. 11, pp. 1-7 (2020).
Wolfson, P.E. et al., "MDMA-assisted psychotherapy for treatment of anxiety and other psychological distress related to life-threatening illnesses: a randomized pilot study," Scientific Reports, vol. 10, pp. 1-15 (2020).
Yazar-Klosinski, B.B. et al., "Potential Psychiatric Uses for MDMA," Developments, vol. 101, pp. 194-196 (2017).

PharmaTher Holdings Ltd. Dec. 14, 2021. PharmaTher Announces Positive Research Results for LSD Microneedle Patch. Press Release. <URL: https://psychedelicinvest.com/pharmather-announces-positive-research-results-for-lsd-microneedle-patch/>.
Szabo, A et al., "Psychedelic N,N-Dimethyltryptamine and 5-Methoxy-N,N-Dimethyltryptamine Modulate Innate and Adaptive Inflammatory Responses through the Sigma-1 Receptor of Human Monocyte-Derived Dendritic Cells," PLoS One, vol. 9, pp. 1-12 (2014).
Sherwood, A.M. et al., "Synthesis and Characterization of 5-MeO-DMT Succinate for Clinical Use," ACS Omega, vol. 5, pp. 32067-32075 (2020).
Galeffi, C. et al., "N,N-Dimethyl-5-Methoxytryptamine, a Component of a Dart Poison of the Yanoáma Indians," Journal of Natural Products, vol. 46, pp. 586-587 (1983).
Shulgin, A. et al. TiHKAL: The Continuation. #38. 5-MEO-DMT. Tryptamine, 5-Methoxy-N,N-Dimethyl; Indole, 5-Methoxy-3-[2-(Dimethylamino)Ethyl]; 5-Methoxy-N,N-Dimethyltryptamine; 5-Methoxy-3-[2-(Dimethylamino)Ethyl]Indole; N,N,O-Trimethylserotonin; N,N,O-TMS; Bufotenine Methyl Ether; O-Methylbufotenine; OMB. <URL: https://erowid.org/library/books_online/tihkal/tihkal38.shtml >.
CHEMCATS. Chemical Abstracts Service: Columbus, OH. Chemical Name: 4H-Pyrrolo[2,3-b]pyridine-4-one, 1,7-dihydro-. CHEMCATS Accession No. 1756550559. Catalog Name: Sagechem Limited Product List. Order No. Catalog: S243355. CAS Registry No. 1076197-59-5 (1 page).
CHEMCATS. Chemical Abstracts Service: Columbus, OH. Chemical Name: 1-methyl-1H-pyrrolo[2,3-b]pyridin-4-ol. CHEMCATS Accession No. 1545199867. Catalog Name: Azepine Product List. Order No. Catalog: AZ04819515. CAS Registry No. 1781876-60-5 (1 page).
CHEMCATS. Chemical Abstracts Service: Columbus, OH. Chemical Name: 1-methylpyrrolo[2,3-b]pyridin-4-ol. CHEMCATS Accession No. 1442516433. Catalog Name: Aurora Building Blocks 2. Order No. Catalog: 115.267.167. CAS Registry No. 1781876-60-5 (1 page).
CHEMCATS. Chemical Abstracts Service: Columbus, OH. Chemical Name: 1-methyl-1H-pyrrolo[2,3-b]pyridin-4-ol. CHEMCATS Accession No. 0002254898. Catalog Name: FCH Group Reagents for Synthesis. Order No. Catalog: FCH1635008. CAS Registry No. 1781876-60-5 (1 page).
CHEMCATS. Chemical Abstracts Service: Columbus, OH. Chemical Name: 1H-Pyrrolo[2,3-B]Pyridin-4(7H)-One. CHEMCATS Accession No. 2022337458. Catalog Name: Chemieliva Pharmaceutical Product List. Order No. Catalog: CE0957308. CAS Registry No. 1076197-59-5 (1 page).
CHEMCATS. Chemical Abstracts Service: Columbus, OH. Chemical Name: 1H-Pyrrolo[2,3-b]pyridin-4(7H)-one. CHEMCATS Accession No. 1621739382. Catalog Name: Ambeed, Inc. Product List. Order No. Catalog: A763560 CAS Registry No. 1076197-59-5 (1 page).
CHEMCATS. Chemical Abstracts Service: Columbus, OH. Chemical Name: 1H-Pyrrolo[2,3-b]pyridin-4-ol hydrate. CHEMCATS Accession No. 1773869211. Catalog Name: Aurora Building Blocks 3. Order No. Catalog: 129.194.895. CAS Registry No. 2031269-35-7 (1 page).
CHEMCATS. Chemical Abstracts Service: Columbus, OH. Chemical Name: 1H-pyrrolo[2,3-b]pyridin-4-ol hydrate. CHEMCATS Accession No. 0968477988. Catalog Name: ASW MedChem Product List. Order No. Catalog: TH-45275. CAS Registry No. 2031269-35-7 (1 page).
CAplus. Chemical Abstracts Service: Columbus. CAplus Accession No. 2017:1595854. Title: Preparation of tetrahydropyridoindolylcycloalkylacrylic acid derivatives and analogs for us as estrogen receptor modulators. Inventor: Huang, P.Q. et al. (4 pages).
Sohlberg, E. et al., "The impact of the site of blood sampling on pharmacokinetic parameters following sublingual dosing to dogs," Journal of Pharmacological and Toxicological Methods, vol. 67, pp. 1-4 (2013).

(56) References Cited

OTHER PUBLICATIONS

Illum, L. et al., "The Effect of Blood Sampling Site and Physicochemical Characteristics of Drugs on Bioavailability after Nasal Administration in the Sheep Model," Pharmaceutical Research, vol. 20, pp. 1474-1484 (2003).

Gupta, S.P., "QSAR Studies on Drugs Acting at the Central Nervous System," Chemical Reviews, vol. 89, pp. 1765-1800 (1989).

Stoll, A. et al., "49. Amide der stereoisomeren Lysergsäuren und Dihydro-lysergsäuren," Helvetica Chimica Acta, vol. 38, pp. 421-433 (1955).

Halberstadt, A.L. et al., "Pharmacological characterization of the LSD analog N-ethyl-N-cyclopropyl lysergamide (ECPLA)," Psychopharmacology, vol. 236, pp. 799-808 (2019).

McKenna, D.J. et al., "Differential interactions of indolealkylamines with 5-hydroxytryptamine receptor subtypes," Neuropharmacology, vol. 29, pp. 193-198 (1990).

Glennon, R.A. et al., "Serotonin Receptor Binding Affinities of Tryptamine Analogues," Journal of Medicinal Chemistry, vol. 22, pp. 428-432 (1979).

Klein, A.K. et al., "Investigation of the Structure—Activity Relationships of Psilocybin Analogues," ACS Pharmacology & Translational Science, vol. 4, pp. 533-542 (2021).

Sard, H. et al., "SAR of psilocybin analogs: Discovery of a selective 5-HT2C agonist," Bioorganic & Medicinal Chemistry Letters, vol. 15, pp. 4555-4559 (2005).

Lyon, R.A. et al., "Indolealkylamine analogs share 5-HT2 binding characteristics with phenylalkylamine hallucinogens," European Journal of Pharmacology, vol. 145, pp. 291-297 (1988).

Glässer, A., "Some Pharmacological Actions of D-Lysergic Acid Methyl Carbinolamide," Nature, vol. 189, pp. 313-314 (1961).

Lala, P.K. et al., "Role of nitric oxide in tumor progression: Lessons from experimental tumors," Cancer and Metastasis Reviews, vol. 17, pp. 91-106 (1998).

Golub, T.R. et al., "Molecular Classification of Cancer: Class Discovery and Class Prediction by Gene Expression Monitoring," Science, vol. 286, pp. 531-537 (1999).

Medline Plus, "Cancer," National Institute of Health (2007) <URL: www.nlm.nih.gov/medlineplus/cancer.html>.

(A)

(B)

(A)

(B)

(A)

(B)

(A)

(B)

PHARMACEUTICAL COMPOSITION COMPRISING 5-METHOXY-N,N-DIMETHYLTRYPTAMINE

CROSS-REFERENCE TO RELATED APPLICATIONS

This application is a continuation of U.S. application Ser. No. 17/660,981, filed on Apr. 27, 2022, which is a continuation of International Application No. PCT/GB2021/051476, filed on Jun. 14, 2021, each of which is incorporated by reference herein, PCT/GB2021/051476 claiming the benefit of priority to GB Application No. 2008964.5, filed on Jun. 12, 2020, GB Application No. 2008961.1, filed on Jun. 12, 2020, GB Application No. 2008968.6, filed on Jun. 12, 2020, GB Application No. 2019241.5, filed on Dec. 7, 2020, GB Application No. 2101640.7, filed on Feb. 5, 2021, GB Application No. 2101634.0, filed on Feb. 5, 2021, GB Application No. 2102100.1, filed on Feb. 15, 2021, GB Application No. 2102095.3, filed on Feb. 15, 2021, GB Application No. 2105049.7, filed on Apr. 8, 2021, GB Application No. 2105047.1, filed on Apr. 8, 2021, and GB Application No. 2105462.2, filed on Apr. 16, 2021.

FIELD OF THE INVENTION

This invention relates to pharmaceutically acceptable salts of 5-methoxy-N,N-dimethyltryptamine. In particular, though not exclusively, the invention relates to formulations and uses of the same as a medicament.

BACKGROUND OF THE INVENTION 5-methoxy-N,N-dimethyltryptamine (5MeODMT) is a pharmacologically active compound of the tryptamine class and has the chemical formula:

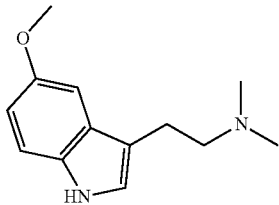 [SMILES: COc1ccc2[nH]cc(CCN(C)C)c2c1]

5MeODMT is a psychoactive/psychedelic substance found in nature and is believed to act mainly through serotonin receptors. It is also believed to have a high affinity for the 5-$HT_2$ and 5-$HT_{1A}$ subtypes, and/or inhibits monoamine reuptake.

However, 5MeODMT is not well understood and uses of this compound have not been well explored. Further, 5MeODMT is not easy to handle, and there are challenges in formulating it for effective delivery in pharmaceutically useful compositions.

There remains a need in the art for improved formulations and uses of 5MeODMT.

SUMMARY OF THE INVENTION

In a first aspect of the invention, there is provided a composition comprising a pharmaceutically effective amount of a pharmaceutically acceptable salt of 5-methoxy-N,N-dimethyltryptamine (5MeODMT).

The invention provides for improved formulations and uses of 5MeODMT salts.

In an embodiment the composition comprises a dosage amount of 5MeODMT in the range of 0.05 mg to 100 mg.
In an embodiment the composition comprises a dosage amount of 5MeODMT in the range of 0.1 mg to 50 mg.
In an embodiment the composition comprises a dosage amount of 5MeODMT in the range of 0.5 mg to 25 mg.
In an embodiment the composition comprises a dosage amount of 5MeODMT in the range of 0.5 mg to 10 mg.
In an embodiment the composition comprises a dosage amount of 5MeODMT in the range of 1 mg to 10 mg.
In an embodiment the composition comprises a dosage amount of 5MeODMT in the range of 1 mg to 8 mg.
In an embodiment the composition comprises a dosage amount of 5MeODMT in the range of 3 mg to 15 mg.
In an embodiment the composition comprises a dosage amount of 5MeODMT in the range of 0.005 mg to 100 mg.
In an embodiment the composition comprises a dosage amount of 5MeODMT in the range of 0.001 mg to 100 mg.
In an embodiment the composition comprises a dosage amount of 5MeODMT in the range of 0.0005 mg to 100 mg.

The level of the active agent can be adjusted as required by need for example to suit a certain patient group (e.g. the elderly) or the conditions being treated.

In an embodiment the composition is formulated in a dosage form selected from: oral, transdermal, inhalable, intravenous, or rectal dosage form.

It is advantageous to be able to deliver the active agent in different forms, for example to suit a certain patient group (e.g. the elderly) or the conditions being treated.

In an embodiment the composition is formulated in a dosage form selected from: tablet, capsule, granules, powder, free-flowing powder, inhalable powder, aerosol, nebulised, vaping, buccal, sublingual, sublabial, injectable, or suppository dosage form.

In an embodiment the powder is suitable for administration by inhalation via a medicament dispenser selected from a reservoir dry powder inhaler, a unit-dose dry powder inhaler, a pre-metered multi-dose dry powder inhaler, a nasal inhaler or a pressurized metered dose inhaler.

In an embodiment the powder comprises particles, the particles having a median diameter of less than 2000 μm, 1000 μm, 500 μm, 250 μm, 100 μm, 50 μm, or 1 μm.

In an embodiment the powder comprises particles, the particles having a median diameter of greater than 500 μm, 250 μm, 100 μm, 50 μm, 1 μm or 0.5 μm.

In an embodiment the powder comprises particles, and wherein the powder has a particle size distribution of d10=20-60 μm, and/or d50=80-120 μm, and/or d90=130-300 μm.

The nature of the powder can be adjusted to suit need. For example, if being made for nasal inhalation, then the particles may be adjusted to be much finer than if the powder is going to be formulated into a gelatine capsule, or differently again if it is going to be compacted into a tablet.

In an embodiment the 5MeODMT salt is amorphous or crystalline.

In an embodiment the 5MeODMT salt is in a polymorphic crystalline form, optionally 5MeODMT salt is Polymorph A.

In an embodiment the 5MeODMT salt is a benzoate, fumarate, citrate, acetate, succinate, halide, fluoride, chloride, bromide, iodide, oxalate, or triflate salt, optionally the salt is the chloride, benzoate or fumarate salt.

In an embodiment, the 5MeODMT salt is the chloride salt. In an embodiment, the 5MeODMT salt is the chloride salt in a liquid medium. In an embodiment, the 5MeODMT salt is the chloride salt in solution.

For the salt, the dosage amount is the equivalent amount of the free base delivered when the salt is taken. So 100 mg dosage amount of 5MeODMT corresponds to 117 mg of the hydrochloride salt (i.e. both providing the same molar amount of the active substance). The greater mass of the salt needed is due to the larger formula weight of the hydrogen chloride salt (i.e. 218.3 g/mol for the free base as compared to 254.8 g/mol for the salt). Similarly, for the deuterated or triturated version of 5MeODMT (also considered within the scope of the invention), a slight increase in mass can be expected due to the increased formula weight of these isotopic compounds.

Amorphous and crystalline substances often show different chemical/physical properties, e.g. improved rate of dissolution in a solvent, or improved thermal stability. Similarly, different polymorphs may also show different and useful chemical/physical properties.

In an embodiment the composition comprises one or more pharmaceutically acceptable carriers or excipients.

In an embodiment the composition comprises one or more of: mucoadhesive enhancer, penetrating enhancer, cationic polymers, cyclodextrins, Tight Junction Modulators, enzyme inhibitors, surfactants, chelators, and polysaccharides.

In an embodiment the composition comprises one or more of: chitosan, chitosan derivatives (such as N,N,N-trimethyl chitosan (TMC), n-propyl-(QuatPropyl), n-butyl-(Quat-Butyl) and n-hexyl (QuatHexyl)-N,N-dimethyl chitosan, chitosan chloride), β-cyclodextrin, *Clostridium perfringens* enterotoxin, zonula occludens toxin (ZOT), human neutrophil elastase inhibitor (ER143), sodium taurocholate, sodium deoxycholate sodium, sodium lauryl sulphate, glycodeoxycholat, palmitic acid, palmitoleic acid, stearic acid, oleyl acid, oleyl alchohol, capric acid sodium salt, DHA, EPA, dipalmitoyl phophatidyl choline, soybean lecithin, lysophosphatidylcholine, dodecyl maltoside, tetradecyl maltoside, EDTA, lactose, cellulose, and citric acid.

In an embodiment the composition disclosed herein is for use as a medicament. In an embodiment the composition disclosed herein is for use in a method of treatment of a human or animal subject by therapy.

In an embodiment the method of treatment is a method of treatment of:
- conditions caused by dysfunctions of the central nervous system,
- conditions caused by dysfunctions of the peripheral nervous system,
- conditions benefiting from sleep regulation (such as insomnia),
- conditions benefiting from analgesics (such as chronic pain),
- migraines,
- trigeminal autonomic cephalgias (such as short-lasting unilateral neuralgiform headache with conjunctival injection and tearing (SUNCT), and short-lasting neuralgiform headaches with cranial autonomic symptoms (SUNA)),
- conditions benefiting from neurogenesis (such as stroke, traumatic brain injury, Parkinson's dementia),
- conditions benefiting from anti-inflammatory treatment,
- depression,
- treatment resistant depression,
- anxiety,
- substance use disorder,
- addictive disorder,
- gambling disorder,
- eating disorders,
- obsessive-compulsive disorders, or
- body dysmorphic disorders,
- optionally the condition is SUNCT and/or SUNA.

Treatment of the above conditions may be beneficially improved by taking the invention.

In an embodiment, the method of treatment is a method of treatment of alcohol-related diseases and disorders, eating disorders, impulse control disorders, nicotine-related disorders, tobacco-related disorders, methamphetamine-related disorders, amphetamine-related disorders, *cannabis*-related disorders, cocaine-related disorders, hallucinogen use disorders, inhalant-related disorders, benzodiazepine abuse or dependence related disorders, and/or opioid-related disorders.

In an embodiment, the method of treatment is a method of treatment of tobacco addiction. In an embodiment, the method is a method of reducing tobacco use. In an embodiment, the method of treatment is a method of treatment of nicotine addiction. In an embodiment, the method is a method of reducing nicotine use.

In an embodiment, the method of treatment is a method of treating alcohol abuse and/or addiction. In an embodiment, the method of treatment is a method of reducing alcohol use.

In an embodiment, the method of treatment is a method of treating or preventing heavy drug use.

In an embodiment, the method of treatment is a method of treating or preventing heavy drug use, including, but not limited to, alcohol, tobacco, nicotine, cocaine, methamphetamine, other stimulants, phencyclidine, other hallucinogens, marijuana, sedatives, tranquilizers, hypnotics, and opiates. It will be appreciated by one of ordinary skill in the art that heavy use or abuse of a substance does not necessarily mean the subject is dependent on the substance.

In an embodiment the method of treatment is a method of treatment of more than one of the above conditions, for example, the method of treatment may be a method of treatment of depression and anxiety.

In an embodiment the composition is administered one or more times a year.

In an embodiment the composition is administered one or more times a month.

In an embodiment the composition is administered one or more times a week.

In an embodiment the composition is administered one or more times a day.

In an embodiment the composition is administered at such a frequency as to avoid tachyphylaxis.

In an embodiment the composition is administered together with a complementary treatment and/or with a further active agent.

In an embodiment the further active agent is a psychedelic compound, optionally a tryptamine. In an embodiment the further active agent is lysergic acid diethylamide (LSD), psilocybin, psilocin or a prodrug thereof.

In an embodiment the further active agent is an antidepressant compound.

In an embodiment the further active agent is selected from an SSRI, SNRI, TCA or other antidepressant compounds.

In an embodiment the further active agent is selected from Citalopram (Celexa, Cipramil), Escitalopram (Lexapro, Cipralex), Fluoxetine (Prozac, Sarafem), Fluvoxamine (Luvox, Faverin), Paroxetine (Paxil, Seroxat), Sertraline (Zoloft, Lustral), Desvenlafaxine (Pristiq), Duloxetine (Cymbalta), Levomilnacipran (Fetzima), Milnacipran (Ixel, Savella), Venlafaxine (Effexor), Vilazodone (Viibryd), Vortioxetine (Trintellix), Nefazodone (Dutonin, Nefadar, Serzone), Trazodone (Desyrel), Reboxetine (Edronax), Teniloxazine (Lucelan, Metatone), Viloxazine (Vivalan), Bupropion (Wellbutrin), Amitriptyline (Elavil, Endep), Amitriptylinoxide (Amioxid, Ambivalon, Equilibrin), Clomipramine (Anafranil), Desipramine (Norpramin, Pertofrane), Dibenzepin (Noveril, Victoril), Dimetacrine (Istonil), Dosulepin (Prothiaden), Doxepin (Adapin, Sinequan), Imipramine (Tofranil), Lofepramine (Lomont, Gamanil), Melitracen (Dixeran, Melixeran, Trausabun), Nitroxazepine (Sintamil), Nortriptyline (Pamelor, Aventyl), Noxiptiline (Agedal, Elronon, Nogedal), Opipramol (Insidon), Pipofezine (Azafen/Azaphen), Protriptyline (Vivactil), Trimipramine (Surmontil), Amoxapine (Asendin), Maprotiline (Ludiomil), Mianserin (Tolvon), Mirtazapine (Remeron), Setiptiline (Tecipul), Isocarboxazid (Marplan), Phenelzine (Nardil), Tranylcypromine (Parnate), Selegiline (Eldepryl, Zelapar, Emsam), Caroxazone (Surodil, Timostenil), Metralindole (Inkazan), Moclobemide (Aurorix, Manerix), Pirlindole (Pirazidol), Toloxatone (Humoryl), Agomelatine (Valdoxan), Esketamine (Spravato), Ketamine (Ketalar), Tandospirone (Sediel), Tianeptine (Stablon, Coaxil), Amisulpride (Solian), Aripiprazole (Abilify), Brexpiprazole (Rexulti), Lurasidone (Latuda), Olanzapine (Zyprexa), Quetiapine (Seroquel), Risperidone (Risperdal), Trifluoperazine (Stelazine), Buspirone (Buspar), Lithium (Eskalith, Lithobid), Modafinil (Provigil), Thyroxine (T4), Triiodothyronine (T3).

In an embodiment the further active agent is selected from Celexa (citalopram), Cymbalta (duloxetine), Effexor (venlafaxine), Lexapro (escitalopram), Luvox (fluvoxamine), Paxil (paroxetine), Prozac (fluoxetine), Remeron (mirtazapine), Savella (milnacipran), Trintellix (vortioxetine), Vestra (reboxetine), Viibryd (vilazodone), Wellbutrin (bupropion), Zoloft (sertraline).

In an embodiment the complementary treatment is psychotherapy.

In an embodiment, there is provided a composition comprising a pharmaceutically effective amount of a pharmaceutically acceptable salt of 5MeODMT for use in a method of treatment of treatment resistant depression.

In an embodiment, there is provided a composition comprising a pharmaceutically effective amount of a pharmaceutically acceptable salt of 5MeODMT for use in a method of treatment of depression.

In an embodiment, there is provided a composition comprising a pharmaceutically effective amount of a pharmaceutically acceptable salt of 5MeODMT for use in a method of treatment of PTSD.

In an embodiment, there is provided a composition comprising a pharmaceutically effective amount of a pharmaceutically acceptable salt of 5MeODMT for use in a method of treatment of addiction/substance misuse disorders.

In an embodiment, there is provided a nasal inhalation composition comprising a pharmaceutically effective amount of a pharmaceutically acceptable salt of 5MeODMT for use in a method of treatment of treatment resistant depression.

Treatment of the above conditions may be beneficially improved by taking the invention together with some complementary treatments; also these treatments may occur much less regularly than some other treatments that require daily treatments or even multiple treatments a day.

The present invention will now be further described with reference to the following, and the accompanying drawings, of which:

DETAILED DESCRIPTION OF THE INVENTION

Figure 1:
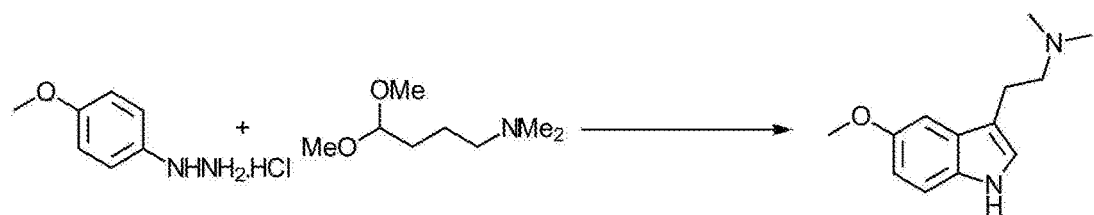
FIG. 1 is a schematic route for the synthesis of 5MeODMT.

FIG. 1 shows a one-step synthesis of 5MeODMT from the reaction of 4-methoxyphenylhydrazine hydrochloride with (N,N)-dimethylamino)butanal dimethyl acetal.

Figure 2:
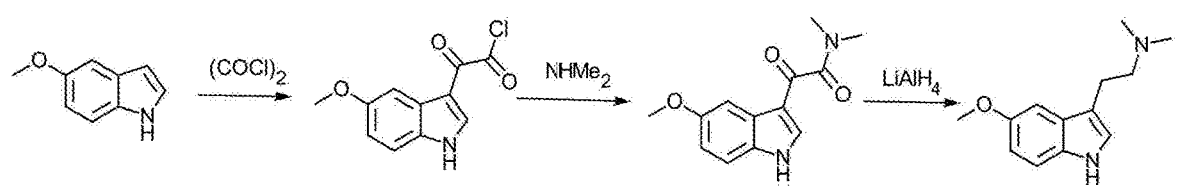
FIG. 2 is a further schematic route for the synthesis of 5MeODMT.

FIG. 2 shows a three step synthesis of 5MeODMT. The first step involves the reaction of 5-methoxyindole with oxalyl chloride. The resultant product is aminated with dimethylamine and then is reduced with lithium aluminium hydride.

Figure 3:
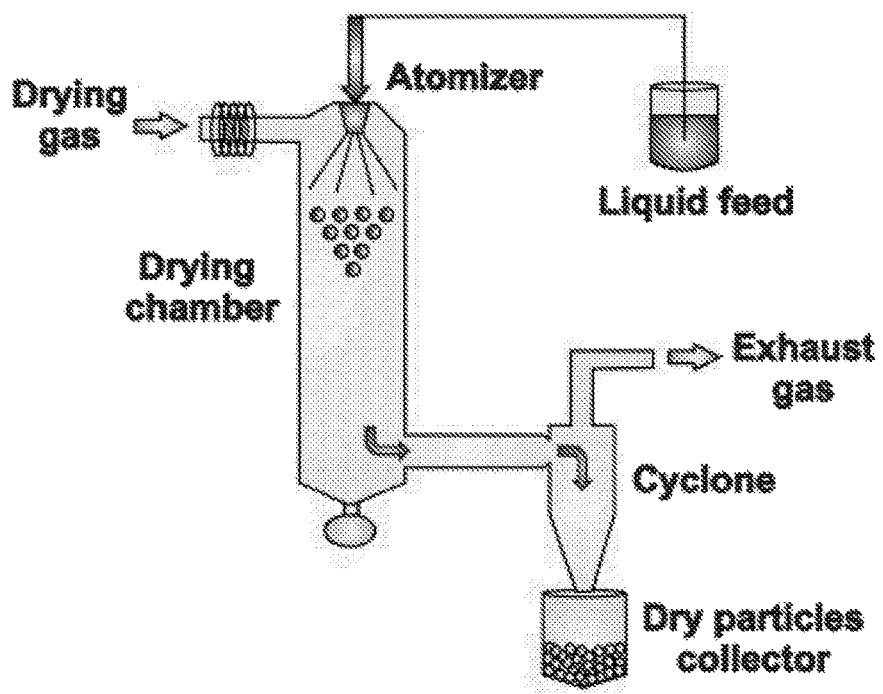
FIG. 3 is a schematic route for the preparation of a powder form of 5MeODMT.

FIG. 3 shows the schematic route for the formation of a powder form of 5MeODMT using a spray drying process.

EXAMPLES

Example 1: Synthesis of 5MeODMT (the Free Base) in on Step (the Free Base)

A schematic representation of this reaction is shown in FIG. 1.

Hydrazine (1.0 eq), diethyl acetal (1.2 eq), and aqueous sulfuric acid (0.1 eq) where heated together at 65-75° C. for 18 hours. MTBE (10 vol) was added, followed by adjustment to about pH10 using 12% caustic (about 1.1 eq.). The layers were separated and the aqueous fraction back extracted with MTBE (10 vol). The combined organic fractions were washed with water (10 vol) twice, then evaporated to dryness under vacuum. Yield 100%.

Example 2: Synthesis of 5MeODMT (the Free Base) in Three Steps

A schematic representation of this reaction is shown in FIG. 2.

Step 1—Add methyl tert-butyl ether (MTBE) (15 vol) into the reaction vessel and cool to −20 to −30° C., before adding oxalyl chloride (1.5 eq), maintaining the temperature at no more than −20° C. Add a solution of 5-methoxyindole (1.0 eq) in THF (1 vol) to the reaction vessel, maintaining the temperature at no more than −20° C. Allow the reaction to warm to 0-5° C. and stir for at least 1 hour, ensuring that no more than 2% of the starting material indole remains.

Cool the reaction to between −20 to −30° C. and add a solution of methanol (1 vol) and MTBE (1 vol), maintaining the temperature at no more than −20° C. Allow the reaction to warm to 0-5° C. over no less than 30 minutes and stir for at least 1 hour.

Filter and wash the solids with MTBE cooled to 0-5° C. Add the washed filtered solids and methanol (20 vol) to a reaction vessel. Heat to 60-65° C. and stir for no more than 30 minutes. Cool to 0-5° C. over no less than 2 hours and stir for no less than 2 hours. Filter and wash the solids with MTBE cooled to 0-5° C. Dry the solids obtained at no more than 40° C. for no less than 12 hours. Yield 95%.

Step 2—Add the compound obtained in step 1 (1.0 eq) to a reaction vessel together with dimethylamine hydrochloride (3.0 eq) and methanol (2 vol). Add 25% NaOMe in methanol (3.5 eq), to the reaction maintaining the temperature at no more than 30° C. Warm to and stir for no less than 5 hours, ensuring that no more than 0.5% of the starting material from step 1 remains. Adjust the temperature to 0-5° C. over no less than 2 hours, then add water (5 vol) over no less than 1 hour with stirring at 0-5° C. for no less than 1 hour.

Filter and wash the solids with water cooled to 0-5° C., and dry the solids obtained at no more than 40° C. for no less than 12 hours. Yield 85%.

Step 3—Add the compound obtained in step 2 (1.0 eq) to a reaction vessel. Add 1M LiAlH$_4$ in THF (1.5 eq) in THF (8 vol) to the reaction maintaining no more than 40° C. Heat at reflux for no less than 4 hours ensuring that no more than 2% of the starting material from step 2 remains.

Adjust to 0-5° C. and add water (0.25 vol) in THF (0.75 vol) over no less than 30 minutes, maintaining no more than 10° C. Then add 15% caustic (0.25 vol) maintaining the temperature at no more than 10° C. Add water (0.65 vol) maintaining the temperature at no more than 10° C. Add THF (0.25 vol) as a vessel rinse and stir the contents at 0-5° C. for no less than 30 minutes. Add sodium sulfate (100 wt %) and stir contents at 0-5° C. for no less than 30 minutes.

Filter and wash the solids with toluene (2×10 vol) and keep liquors separate. Recharge THF liquors to a clean vessel and distil under vacuum to minimum stir. Charge toluene liquors and distil under vacuum to about 10 vol. Then add water (5 vol) and stir for no less than 15 minutes. Stop, settle and remove aqueous layer to waste. Charge with 4% HCl to a pH of between 1-2 (about 4 vol) and stir for no less than 15 minutes. Stop, settle and remove organic layer to waste. Charge MTBE (15 vol). Charge with 15% caustic to a pH between 11-13 (about 0.9 vol). Stir for no less than 15 minutes. Stop, settle and remove aqueous layer to waste. Charge with water (5 vol). Stir for no less than 15 minutes. Stop, settle and remove the aqueous layer to waste.

Example 3: Synthesis of 5MeODMT Hydrochloride Salt

5MeODMT (the free base) is dissolved in toluene (1.0 to 2.5 vol). Isopropyl alcohol (IPA) was then added (2.5 vol) followed by 1.25M HCl in IPA (1.0 eq) and the temperature adjusted to 0-5° C. over 1 hour.

If no precipitation/crystallization occurs, toluene (6.25 vol) is added over 30 minutes. The mixture was then stirred at 0-5° C. for 2 hours. The resultant solid is filtered, washed with toluene (3.8 vol). The solid was dried under vacuum at ambient temperature. Yield 58%.

Example 4: Synthesis of 5MeODMT Benzoate Salt

5MeODMT (the free base) is dissolved in toluene (1 eq) and benzoic acid (1 eq) in toluene (10 vol) is added over a period of 20 minutes and stirred at room temperature for 2 hours. The resultant precipitation/crystallization was filtered and washed with toluene (2.5 vol) and dried under vacuum at room temperature.

Isopropyl acetate (IPAc) (15.8 vol) was added to the solids obtained above and the temperature was raised to about 73° C. until the solid dissolved. The solution was allowed to cool to 0-5° C. over 2 hours and this temperature was maintained for 1 hour with stirring. The resultant benzoate salt was filtered and vacuum dried at room temperature. Yield 68%.

Example 5: Synthesis of 5MeODMT Fumarate Salt

5MeODMT (the free base) is added to a solution of fumaric acid (0.5 eq) in IPA over 15 minutes at 40-45° C. The resultant solution was cooled at room temperature and stirred for 16 hours. The solution was then cooled to 0-5° C. with stirring for 2 hours. The resulting precipitation/crystallization was filtered and was rinsed with toluene (2.5 vol). Yield 68%.

Example 6: 5MeODMT Powder

A schematic route for the preparation of a powder form of 5MeODMT (or the salt thereof) is shown in FIG. 3. The three main steps in the process are:
1. Spray drying a solution containing the substance(s) of interest (e.g. 5MeODMT, or the salt, thereof inclusive of any excipients). This can be done via an atomizing nozzle such as with rotary atomizers, pressure atomizers, twin fluid nozzles, ultrasonic atomizers, four-fluid nozzles. This is done so as to form droplets capable of generating co-formed particles in the desired particle size range.
2. Drying of the atomized droplets (e.g. with nitrogen gas, optionally at an elevated temperature).

3. Separating and collecting the dried particles from the gas stream (e.g. using a cyclone separator to capture the required size fraction).

Example 7: Effects on the Central Nervous System Function

In the following examples, BPL-5MEO refers to 5-methoxy-N,N-dimethyltryptamine (5MeODMT).

In the following examples, the hydrochloride salt of 5MeODMT was used.

The following Examples (7-11) summarizes applicant-sponsored safety pharmacology studies to assess the effects of BPL-5MEO on CNS, cardiovascular system, and respiratory system function. The study designs are based on those in the International Council for Harmonisation (ICH) S7A/B Guidance and were conducted in compliance with GLP regulations.

The pharmacological effects of BPL-5MEO on CNS function was assessed using a Functional Observational Battery (FOB) in male Sprague-Dawley rats following a single intranasal administration (ITR study 15951).

The test and control/vehicle items were administered by single dose intranasal administration to both nostrils, as shown in Table 1.

TABLE 1

Experimental Design of Study 15951

| Group No. | Group Designation a | Dose Level (mg/kg) | Dose Concentration (mg/mL) | Dose Volume c (µL/kg) | No. of Male Animals |
|---|---|---|---|---|---|
| 4 | Control b | 0 | 0 | 75 Right | 6 |
| 3 | Low Dose | 1.5 | 10 | Nostril + | 6 |
| 2 | Mid Dose | 3 | 20 | 75 Left | 6 |
| 1 | High Dose | 10 | 66.67 | Nostril | 6 | a The observers performing the FOB were not aware of the specific treatment administered to the animals.
b Control animals were administered 0.1% hydroxypropyl methyl cellulose (HPMC) in water.
c Dose volume did not exceed 25 µL/nostril for all animals regardless of their bodyweight.

Parameters monitored included mortality and clinical signs. General behavioral changes were assessed using FOB at 6 timepoints: before dosing, and at 15 minutes, 1, 2, 4, and 24 hours postdosing. On each occasion, the FOB was performed at 4 stages: when the animals were in their home cage, while handling the animals, when the animals were freely moving in an open-field, and when they received diverse stimuli for reactivity evaluation. The body temperature and neuromuscular strength were also measured on each of the occasions detailed above.

The FOB examinations were grouped according to functional domains of the nervous system as shown in Table 2.

TABLE 2

Functional Domains of the Nervous System and Associated Observations

| Domain | Behavioral Observations Performed |
|---|---|
| Behavioral | Posture and activity in home cage/bin |
| | Ease of removal from the cage/bin |
| | Handling reactivity |
| | Arousal |
| | Rearing |
| | Exploratory activity |
| | Touch response |
| | Abnormal or stereotyped behavior |

TABLE 2-continued

Functional Domains of the Nervous System and Associated Observations

| Domain | Behavioral Observations Performed |
|---|---|
| Neurological (sensorimotor)/ Neuromuscular | Vision test |
| | Touch response |
| | Auditory test |
| | Tail pinch response |
| | Eye blink response |
| | Flexor reflex |
| | Extensor thrust reflex |
| | Pinna reflex |
| | Proprioceptive positioning |
| | Righting reaction |
| | Hindlimb foot splay |
| | Involuntary motor movements (such as convulsion and tremors) |
| | Gait |
| | Forelimb and hindlimb grip strength |
| Domain | Behavioral Observations Performed |
| Autonomic | Lacrimation |
| | Salivation |
| | Pupil response to light |
| | Palpebral closure |
| | Defecation |
| | Urination |
| | Piloerection |
| | Exophthalmos |
| | Body temperature |

There was no treatment-related mortality/morbidity. Transient BPL-5MEO-related clinical signs were noted immediately following dosing and consisted mainly of decreased activity, lying on the cage floor, shallow/increased respiration and dilated pupils at all dose groups. Tremors, salivation, and gasping were observed in some animals at the 3 and 10 mg/kg doses, and twitching was noted in one animal at 10 mg/kg.

In the behavioral domain of the FOB, a single intranasal administration of BPL-5MEO at doses of 1.5, 3, and 10 mg/kg resulted in transient decreased activity, lying on the cage floor, and decreased rearing at 15 minutes postdose. All behavioral parameters were comparable to control animals at 1-hour postdose.

In the neurological (sensorimotor)/neuromuscular domain of the FOB, a single intranasal administration of BPL-5MEO at 1, 5, and 10 mg/kg resulted in transient changes in gait (difficulty in movement) at all dose levels. All neurological (sensorimotor)/neuromuscular parameters were comparable to control animals at 1-hour postdose.

In the autonomic domain, a single intranasal administration of BPL-5MEO of 1, 5, and 10 mg/kg was associated with salivation, piloerection, increased respiration, dilated pupils and changes in body temperature was noted across all dose levels. All autonomic parameters were comparable with control animals at 2 hours postdose.

In conclusion, the single intranasal administration of BPL-5MEO at doses of 1.5, 3, and 10 mg/kg resulted in transient clinical signs, consistent with observable changes in behavior, neurological (sensorimotor)/neuromuscular and autonomic parameters which were fully resolved within 1 or 2 hours following dosing.

Example 8: Effects on Cardiovascular Function

In Vitro Study

The in vitro effect of 5MeODMT on the hERG potassium channel current ($I_{Kr}$), the rapidly activating, delayed rectifier cardiac potassium current, was assessed using the patch clamp technique in stably transfected human embryonic kidney (HEK-293) cells that expressed the hERG gene (CRL study 1020-5458). This assay is employed as a screen to assess potential risks for QT interval prolongation.

The study was conducted in 2 phases: Phase 1 assessed the onset and steady-state inhibition of hERG at a selected concentration of 30 µM 5MeODMT; Phase 2 assessed the concentration response if the results from Phase 1 showed inhibition of 20% or more. The initial concentration of 30 µM was selected based on the results of an exploratory dose-range finding study in dogs, where intranasal administration of 2.5 mg/kg BPL-5MEO resulted in a mean $C_{max}$ of 803 ng/mL (3.67 µM) 5MeODMT. A solution of 30 µM used in Phase 1 provided an 8-fold margin over this concentration.

In Phase 1, the 30 µM concentration of 5MeODMT in protein free perfusate inhibited hERG potassium ion current by 77.8±7.4% (n=3). Therefore, Phase 2 was undertaken using concentrations of 1, 3, 10, and 35 µM 5MeODMT in protein free perfusate (corresponding to 0.2, 0.6, 2.0, and 7.2 µg/mL of unbound drug substance).

In Phase 2, 5MeODMT inhibited hERG potassium ion channel current in a concentration-dependent manner as presented in Table 3.

TABLE 3

Mean Percent Inhibition of hERG Potassium ion Channel Current by 5MeODMT (in protein free perfusate)

| | Concentration of 5MeODMT (µM) | | | |
|---|---|---|---|---|
| | 1 | 3 | 10 | 35 |
| Mean ± SD % inhibition (n = 3 cells) | 5.03 ± 1.95% | 23.77 ± 6.10% | 52.72 ± 2.61% | 82.22 ± 1.91% |

The calculated $IC_{50}$ of 5MeODMT for hERG potassium channel current was 8.69 µM (95% confidence limits 5.78-13.06 µM) compared to 12.8 nM (95% confidence limits 6.8-24.3 nM) for the positive control, terfenadine In Vivo Study The pharmacological effects of BPL-5MEO on cardiovascular function (arterial blood pressure and ECG) was monitored by telemetry, in conscious male beagle dogs, following a single intranasal administration.

The highest dose level was selected based on the results from an intranasal maximum tolerated dose (MTD) toxicity study in dogs (Study 62958) where repeated daily dosing 2.5 mg/kg/day of BPL-MEO once daily for 5 consecutive days was marginally tolerable and associated with transient clinical observations of moderate to severe incoordination, vocalization, salivation, shaking, circling, sneezing, decreased activity, and labored respiration that resolved within 60 minutes post dosing. Therefore, the highest dose selected for this study was 1.2 mg/kg/day. The lowest dose of 0.4 mg/kg/day was based on consideration of a maximum clinical dose of 14 mg/day, with the mid-dose of 0.8 mg/kg/day selected to provide a dose-response assessment.

BPL-5MEO and control/vehicle were administered by intranasal instillation to both nostrils per session to a total of 4 dogs. Each dog received 4 administrations (control/vehicle and 3 dose levels of BPL-5MEO) according to a Latin-square design, such that each dog received the various administrations in a unique sequence, as in Table 4. A washout period of at least 2 days was allowed between each successive dose.

TABLE 4

Latin-square design for Dog Cardiovascular Study

| Test Session | Treatment | | | | |
|---|---|---|---|---|---|
| | 1001A | 1002A | 1003A | 1004A[a] | 1104A |
| 1 | Control/Vehicle | Low Dose | Mid Dose | High Dose | — |
| 2 | High Dose | Control/Vehicle | Low Dose | Mid Dose | — |
| 3 | Mid Dose | High Dose | Control/Vehicle | — | Low Dose |
| 4 | Low Dose | Mid Dose | High Dose | — | Control/Vehicle |

[a] Animal 1004A was replaced prior to dosing for Test Session 3 with animal 1104A due to low implant battery.

Low Dose, Mid Dose, High Dose were 0.4, 0.8, and 1.2 mg/kg/day, respectively. The nominal dose levels refer to the freebase of 5MeODMT salt form.

The dose volume administered to each animal was 74/kg/nostril. No animal exceeded a dose volume of 1004/nostril.

The Control/Vehicle was 0.1% hydroxypropyl methyl cellulose (HPMC) in water.

The telemetry signals for arterial blood pressure and pulse rate, ECGs (heart rate [HR], RR, PR, QT, and QTcV intervals and QRS complex duration), body temperature, and locomotor activity, were recorded continuously over the telemetry recording period of at least 1.5 hours before the start of dosing and for at least 24 hours postdosing. Systolic, diastolic and mean arterial blood pressures and pulse rate were obtained from transmitter catheter inserted into the femoral artery. ECGs were obtained from the biopotential leads, from the telemetry transmitter, in a Lead II configuration.

During the study, all animals were also monitored for mortality and clinical signs. Body weights were recorded for general health status check and for dose calculation purposes only.

There were no deaths and no BPL-5MEO-related clinical signs during the study.

The morphology of the P-QRS-T waveforms remained normal and no rhythm or conduction abnormalities were observed in the ECGs between control and treated groups. There were minor differences in the % change of mean HR averaged between approximately 0 and 150 minutes post-dose between all dose levels and the control vehicle. While mean % increases in mean HR increased by 3.7% in the control vehicle during this period, compared to baseline, the observed increases with the low, mid and high dose levels of BPL-5MEO were respectively 7.6%, 10.3%, and 17.2%. However, arterial blood pressure did not seem to show any appreciable differences that were sufficient to have any effect on HR. No other findings were observed. The observed increases in mean HR with all dose levels were non-adverse, reversible and did not show a typical dose relationship.

In conclusion, the single intranasal instillation of BPL-5MEO to both nostrils at doses of 0.4, 0.8, and 1.2 mg/kg/day was well tolerated and did not result in any effects on the cardiovascular system of conscious male Beagle dogs.

Example 9: Absorption and Pharmacokinetics

In a 14-day intranasal toxicology in male and female rats (ITR report 700041), plasma concentrations of 5MeODMT increased as a function of the dose administered. Peak ($C_{max}$) concentrations were reached within 2 to 5 minutes post dosing ($T_{max}$) with apparent $t_{1/2}$ ranging from 6.8 to 9.4 minutes. Values trended lower on Day 14 compared to Day 1. There was no apparent sex difference and no evidence of accumulation with repeated dosing.

In a 14-day intranasal toxicology study in male and female dogs (ITR report 62959), plasma concentration of 5MeODMT increased as a function of the dose administered. Peak concentrations were reached within 3 to 14 minutes ($T_{max}$), post dosing with apparent elimination half-lives ranging from 19 to 95 minutes. The values were not markedly different on Day 1 and Day 14. There was no apparent sex difference and no evidence of accumulation with repeated dosing.

The data shows that across the dose ranges studied in rats (5, 20, 75 mg/kg), and dogs (0.4, 0.8, 1.5, and 2.5 mg/kg), exposure was generally increased dose-dependently, but not consistently in a dose-proportional manner as some increases were more or less than dose-proportional between different doses. The results do not indicate a saturation of MAOA-mediated metabolism at the doses studied in these species as seen previously in mice.

Example 10: Toxicology

The toxicology program completed with BPL-5MEO consisted of non-pivotal single/repeat dose intranasal studies to determine the MTD in order to help select the highest doses for the pivotal 14-day GLP intranasal toxicology studies in male and female Sprague Dawley rats and Beagle dogs. The intranasal route of administration was used as this is the clinical route of administration. The species selected were based upon information from the published literature, preliminary PK information, availability of historical control information from the testing laboratory, and their standard use and acceptance as appropriate surrogates for intranasal administration. The experimental design of the pivotal 14-day studies included an assessment of systemic exposures (toxicokinetics) and a 14-day recovery period to assess reversibility of any adverse or delayed responses. The once daily dosing for 14 consecutive days in the pivotal studies was intended to provide sufficient systemic exposure to characterize the toxicity potential for a drug substance with a very short half-life.

1. Non-Pivotal Single/Repeat Dose and Tolerance Studies a. Maximum Tolerated Dose Followed by 7-Day Repeat-Dose Toxicology in Rats (Study 700040)

The objectives of this non-GLP study were to determine the maximum tolerated dose and the toxicity profile of BPL-5MEO following intranasal instillation in the rat. The study consisted of 2 parts. The objective of the first part (Dose Escalation Phase), was to determine the MTD of BPL-5MEO following a single intranasal administration to Sprague-Dawley rats. The doses used in part 1 were 15, 30, 50, 65, and 75 mg/kg. Each subsequent dose was administered following at least 24 hours from the commencement of the previous dose. There were 2 males and 2 females in each dose group. The objective of the second part (Main Study Phase), was to determine the toxicity of BPL-5MEO at the MTD of 75 mg/kg following once daily intranasal administration for 7 consecutive days to Sprague-Dawley rats.

All the dose formulation samples collected and analyzed were between 89.2% and 101.3% of nominal concentration, and as such met the acceptance criteria for accuracy (100±15% of their nominal concentration). Analysis was performed using a non-GLP HPLC-UV assay.

All female groups received their targeted doses in both parts. However, as the maximum feasible loading dose was not to exceed 25 μL/naris, regardless of body weight, mean achieved doses for the males at the 30 were still 99.3%, 90.0%, 88.2%, and 89.6%, respectively and were considered to be acceptable.

During Phase I, assessments of mortality, clinical signs and body weights were performed. All animals were observed for 14 days after dosing, following which they were euthanized on Day 15 and subjected to a gross necropsy examination. The necropsy consisted of an external examination, including reference to all clinically-recorded lesions, as well as a detailed internal examination.

Single intranasal administration of 5MeODMT at the dose levels up to 75 mg/kg was tolerated. There was no mortality and gross pathology findings at any dose. Body weight gain was slightly suppressed females at 75 mg/kg. A range of clinical signs were observed and included incoordination, shallow or increased respiration, sneezing, salivation, decreased activity, piloerection, white pasty material around penis (for males), ptosis, laying on the cage floor, and sensitive to touch and shaking. The incidence and severity of these findings evolved as a function of the administered dose and were transient, with most being resolved within 1-hour post dose. Based on the clinical signs and maximal feasible volume/dose, 75 mg/kg was judged to be the MTD, and this dose was selected for Phase 2.

During Phase 2, assessments of mortality, clinical signs and body weights were performed. Following dosing, all animals were euthanized and subjected to a necropsy examination on Day 8. The necropsy consisted of an external examination, including reference to all clinically-recorded lesions, as well as a detailed internal examination. Study plan specific tissues/organs were collected and retained, then trimmed and preserved promptly once the animal was euthanized but these were not further examined microscopically.

Intranasal administration of 5MeODMT at 75 mg/kg for 7 consecutive days was tolerated. There were no mortalities. Body weight gain was slightly suppressed for both sexes. Transient clinical signs similar to those of the Phase I included incoordination, mydriasis, increased or shallow respiration, gasping, sneezing, salivation, pale in colour, decreased activity, lying on the cage floor, piloerection, white pasty material around penis (for males), erect penis (for males), cold to touch, partially or completely closed eyes, sensitive to touch and shaking. These signs were generally less pronounced in terms of severity and incidence during the last few dosing days of this phase, and were resolved daily following dosing within 1-hour post administration. Macroscopic observations of note were limited to dark/pale area of the lungs in 2/10 animals; however, in the absence of histopathological examination, a possible test item-relationship of these findings could not be excluded.

b. Maximum Tolerated Dose Followed by 7-Day Repeat-Dose Toxicology in Dogs (Study 62958)

The objectives of this study were to determine the maximum tolerated dose and the toxicity of the test item, 5MeODMT (as the hydrochloride salt), following intranasal instillation in the dogs. In support of these objectives, the study consisted of 2 individual phases.

The test item was administered once by intranasal instillation to one male and female dog for up to 5 dose levels until the highest tolerable dose (MTD) was determined as described in Table 5.

TABLE 5

Doses Administered in the Dose Escalation Phase in Study 62958

| Dosing Day[a] | Group Designation | Total Dose Level[b] (mg/kg) | Dose Concentration[c] (mg/mL) | Dose Volume (μL/kg) | Number of Animals Males | Number of Animals Females |
|---|---|---|---|---|---|---|
| Day 1 | Dose 1 | 2 | 100 | 10 Right Nostril + 10 Left Nostril | 1 | 1 |
| Day 7 | Dose 2 | 4 | 200 | | | |
| Day 10 | Dose 3 | 5[d] | 250 | | | |
| Day 14 | Dose 4 | 3 | 150 | | | |
| Day 17 | Dose 5 | 3.5 | 175 | | | |

[a] Each subsequent dose was administered following a washout period of minimum 3 days between doses.
[b] Dose levels refer to the freebase of BPL-5MEO salt form.
[c] Targeted dose concentrations were calculated based on an estimated body weight of 10 kg.
[d] These animals were dosed at higher dose level of 5 mg/kg.

There were no BPL-5MEO-related effects on mortality or bodyweights. Slight decreases in food intake were observed following administration for the male on Days 1 (Dose 1) and 9 (Dose 2) and for the female on Days 4 (Dose 1) and 9 (Dose 2). A range of clinical signs were observed and included gnawing cage wire, dilated pupils, changes in respiration, incoordination, decreased activity, vocalization, salivation, erect penis (for males) and shaking. After the last escalating dose at 3.5 mg/kg/day, the male animal presented a convulsion shortly after dosing which lasted for 8 minutes. All clinical signs disappeared within an hour after the dosing except for decreased activity, dilated pupils and lying on the cage floor which were present on few occasions at 1-hour post dose or a few minutes after. The MTD for the test item was considered to be 2.5 mg/kg.

In the phase 2 (dose confirmation), BPL-5MEO was administered at the MTD to one male and female dog once daily by intranasal instillation for 5 consecutive days and then twice daily on Days 6 and 7 (minimum 4 hours apart). During Phase 2, assessments of mortality, clinical signs, body weights and food consumption were performed. A series of blood samples were collected on Days 1 and 7 for determination of plasma concentrations of 5MeODMT using an LC/MS/MS method. Following the last dosing, all animals were euthanized and subjected to a necropsy examination on Day 8. The necropsy consisted of an external examination; including reference to all clinically-recorded lesions, as well as a detailed internal examination. Study plan specific tissues/organs were collected and preserved following necropsy but were not further examined microscopically.

There were no test item-related effects on mortality or bodyweights. Slight decreases in food intake were observed for the male animal on Day 7 and for the female animal on Days 5 and 7. A range of clinical signs were observed and included muscle stiffness, gnawing cage wire, dilated pupils, changes in respiration, decreased activity, incoordination, vocalization, salivation, erect penis (for the male) and shaking. All clinical signs disappeared within an hour after the dosing except for decreased activity, dilated pupils, and lying on the cage floor which were present on few occasions at 1-hour post dose or a few minutes after. All observations were considered transient.

Toxicokinetic assessments were performed on Days 1 and 7; the maximum BPL-5MEO plasma concentration ($C_{max}$) ranged from 541 to 803 ng/mL and was reached ($T_{max}$) within 2 to 15 minutes post dose in both sexes. Dose normalized AUCs ranged from 2980 to 7320 min*kg*ng/mL/mg in both sexes. After $T_{max}$, BPL-5MEO plasma concentrations declined at an estimated $t_{1/2}$ from 19.1 to 34 minutes in both sexes. There were no sex differences in any of the measured toxicokinetic parameters on either occasion. Over the 7-day treatment period, BPL-5MEO did not accumulate when administered daily by intranasal instillation.

2. Pivotal Studies a. A 14-Day Repeat-Dose Intranasal Toxicity Study Followed by a 14-Day Recovery Period in Rats (Study 700041)

The objective of this GLP study was to determine the toxicity and toxicokinetic (TK) profile of BPL-5MEO following intranasal instillation in Sprague Dawley rats for 14 consecutive days and to assess the persistence, delayed onset, or reversibility of any changes following a 14-day recovery period. BPL-5MEO and control/vehicle were administered to groups of rats once daily by intranasal instillation for 14 consecutive days as described in Table 6.

TABLE 6

Doses Administered in 14-Day Repeat Dose Study in Rats

| Group No. | Group Designation | Total Dose Level[b] (mg/kg/day) | Dose Conc. (mg/mL) | Dose Volume[c,d] (μL/kg) | Number of Animals Main Male | Number of Animals Main Female | Number of Animals Recovery Male | Number of Animals Recovery Female | Number of Animals Toxicokinetic Male | Number of Animals Toxicokinetic Female |
|---|---|---|---|---|---|---|---|---|---|---|
| 1 | Vehicle Control a | 0 | 0 | 75 Right Nostril + 75 Left Nostril | 10 | 10 | 5 | 5 | 3 | 3 |
| 2 | Low Dose | 5 | 33.3 | | 10 | 10 | — | — | 6 | 6 |
| 3 | Mid Dose | 20 | 133.3 | | 10 | 10 | — | — | 6 | 6 |
| 4 | High Dose | 75 | 500 | | 10 | 10 | 5 | 5 | 6 | 6 | a Vehicle control animals were administered 0.1% Hydroxypropyl methyl cellulose (HPMC) in water.
[b] Nominal dose levels refer to the freebase of 5MeODMT salt form.
[c] The dose volume administered to each animal was 75 μL/kg/nostril.
[d] Dose volume was not to exceed 25 μL/nostril for all animals regardless of their bodyweight.

The animals were monitored for mortality, clinical signs, respiratory measurements, body weights, food consumption, and body temperature. Ophthalmoscopic examinations and respiratory function tests were performed on all animals at scheduled timepoints. Clinical pathology assessments (hematology, coagulation, clinical chemistry, and urinalysis) were evaluated at termination. Blood samples were collected from the jugular vein from the TK animals on Days 1 and 14, for up to 8 hours after treatment for bioanalysis of 5MeODMT concentrations in plasma and the subsequent calculation of toxicokinetic parameters. Following dosing, the Main animals were euthanized and subjected to a complete necropsy examination on Day 15. The Recovery animals were observed for an additional 14 days and then euthanized and subjected to a complete necropsy examination on Day 28. TK animals were euthanized after the last blood collection and discarded without further examination. At terminal euthanasia, selected tissues/organs were weighed, and microscopic evaluations of a standard set of tissues including the nasal turbinates (4 sections) and brain (7 sections) were performed for all Main and Recovery study animals.

Following dosing, animals in the Main group were euthanized and subjected to a necropsy examination on Day 15. The animals in the Recovery group were observed for 14 days and then euthanized and subjected to a necropsy examination on Day 28. For toxicokinetics, a series of 8 blood samples (approximately 0.5 ml each) were collected from all rats in the Toxicokinetic group (3 rats/sex/timepoint) on Days 1 and 14 of the treatment period at 2, 5, 10, 15 and 30 minutes, and 1.0, 3.0 and 8 hours after treatment. For control rats (3 rats/sex) in the Toxicokinetic group only 1 sample was collected at the 15 minutes post dosing timepoint on Days 1 and 14.

Toxicity was based on the following parameters monitored: mortality/morbidity, clinical observations, body weights/gains, food consumption, ophthalmoscopy, clinical pathology (hematology, coagulation, chemistry, and urinalysis), necropsy observations, selected organ weights, and microscopic examination of a complete set of standard tissues including 4 cross levels of the nasal cavity and 7 sections of the brain.

Results

All the samples met the acceptance criteria for accuracy (100±10% of their nominal concentration).

All animals were dosed without any major incidents and no sneezing was noted. All groups received their targeted doses on Days 1 to 10. As the maximum feasible loading dose was not to exceed 254/naris (due to limited nasal surface area), once the bodyweights exceeded 333 g, male animals in all groups received slightly lower dose levels on Days 11 to 14. This was considered to have no impact on the study data as the differences were negligible.

No mortality occurred over the course of this study.

The observed clinical signs were as follows:

Group 2 (Low Dose)

Both male and female animals exhibited incoordination, shaking, salivation, decreased activity, lying on cage floor and sensitive to touch. For one female animal on Day 3, increased respiration was also observed.

Group 3 (Mid Dose)

Both male and female animals exhibited incoordination, shaking (or tremor), increased or shallow respiration, mydriasis, salivation, decreased activity, partially closed eyes, lying on cage floor and sensitive to touch. Male animals also exhibited erect penis.

Group 4 (High Dose)

Both male and female animals exhibited incoordination, shaking (or tremor), increased or shallow respiration, mydriasis, salivation, decreased activity, partially closed eyes, lying on cage floor and sensitive to touch. Male animals also exhibited erect penis.

Increased respiration was recorded for the mid and high dose group, however, measured respiratory values using plethysmographs proved that there were actually decreases in respiratory rates.

All the above clinical signs were considered to be transient for all groups.

Slight, generally dose-dependent body weight gain suppression was observed for both sexes between Days 1 to 14. There were no changes in food consumption that could be attributed to treatment with at dose levels ≤75 mg/kg/day for 14 days.

On Day 14, slight body temperature increases were observed at 15 minutes and 30 minutes postdose for all treated male animals, for females on Day 14, the body temperature increases were observed in one or all treated groups for all the timepoints (until 2 hours postdose). These increases in body temperature were more pronounced in the mid (20 mg/kg/day) and high (75 mg/kg/day) dose groups.

When compared to pretreatment or control group, decreases in respiratory rates were observed at 20 minutes postdose timepoint which resulted in decreases in respiratory minute volumes. Tidal volume values were either comparable to pre-dose or to control values. The 20-minute postdose respiratory measurements on Day 1 was not performed for Group 2 female animals inadvertently. This considered to have no impact on the study data as the data could be extrapolated form the male animals in the same group. There were no significant between the sexes.

There was no adverse ocular effect, caused by the administration of BPL-5MEO at dose levels ≤75 mg/kg/day for 14 days.

All other clinical observations, bodyweight changes, food consumption changes, and body temperature changes were considered to be not BPL-5MEO-related as they were sporadic, comparable to pretreatment signs or control animals, and not dose-related.

When compared to control Group, platelet, neutrophil, monocyte and basophil counts were slightly increased in mid and high dose groups in both sexes, however, these values were still within the historical ranges. On Day 28, all these values were compared to those in control group.

All changes in the hematology parameters, including those that reached statistical significance, were not attributed to the administration of BPL-5MEO as they were minor (within the normal physiological range), comparable to control values, and/or not dose-related.

When compared to control Group, activated partial thromboplastin times (APTT) were increased for both sexes in the mid (20 mg/kg/day) and high (75 mg/kg/day) dose groups. All the coagulation values on Day 28 were comparable to control group. All other changes in the coagulation parameters were not attributed to the administration of BPL-5MEO as they were minor (within the normal physiological range), comparable to control values, and/or not dose-related.

There were no changes in clinical chemistry and urinalysis parameters that could be attributed to the administration of BPL-5MEO at dose levels ≤75 mg/kg/day for 14 days. All changes in the parameters, including those clinical chemistry parameters that reached statistical significance, were not attributed to the administration of BPL-5MEO as they were minor (within the normal physiological range), comparable to control values, and/or not dose-related.

Compared to control values, there were decreases in thymus weights (absolute and relative to terminal body weight) observed in male animals as shown in Table 7.

TABLE 7

Thymus Weights for Male Animals Compared to Control Group

| Group (Males only) | Mean Absolute Weight [a] | Mean Relative to the Body Weight [a] |
|---|---|---|
| Control (Group 1) | 0.6028 | 0.1756 |
| Group 2 | −4 | −6 |
| Group 3 | 18 | −16 |
| Group 4 | −31 | −28 |

[a] For Control group, the organ weight in grams is reported, for other groups, the percentage compared to the control value is shown.

All changes in the organ weight parameters, including those that reached statistical significance, were not attributed to the administration of BPL-5MeO as they were minor, comparable to control values, and/or not dose related.

There were no macroscopic findings related to treatment with BPL-5MEO in rats in either the Main Recovery groups.

For animals in the Main group, microscopic findings related to treatment with BPL-5MEO, were noted in the nasal cavity sections 1, 2, 3 and 4 of Main rats.

A range of minimal to mild changes were noted in the respiratory, transitional, and/or olfactory epithelium of the nasal cavities, 1, 2, 3, and 4. The incidence and severity of changes were greater in males compared to females and were proportional to the dose of BPL-5MEO.

Microscopic changes observed in rats dosed with 75 mg/kg/day of BPL-5MEO (Group 4) included: respiratory epithelium, minimal to mild degeneration, hyperplasia, and squamous metaplasia, minimal mononuclear infiltrate and/or lumen exudate in nasal cavities 1, 2, 3, and/or 4; transitional epithelium, minimal hyperplasia in nasal cavity 1, and; olfactory epithelium, minimal to mild degeneration and/or minimal mononuclear infiltrate and erosion in nasal cavities 2, 3, and/or 4. Minimal degeneration of the olfactory epithelium of the nasal cavities 2 and 3 was noted in male and/or female rats dosed with 5 and/or 20 mg/kg/day of BPL-5MEO (Group 2 and 3). Minimal degeneration of the respiratory epithelium of the nasal cavities 1 and 2 was noted in male and/or female rats dosed with 20 mg/kg/day of BPL-5MEO (Group 3).

For animals in the Recovery group, microscopic findings related to treatment with BPL-5MEO, were noted in the nasal cavity sections 1, 2, 3, and 4 of Recovery rats. Minimal to mild changes were noted in the respiratory and olfactory epithelium of the nasal cavities, 1, 2, 3, and/or 4. The incidence and severity of changes were greater in males compared to females. Microscopic changes included minimal to mild degeneration of respiratory epithelium in nasal cavities 1 and 2 and minimal degeneration olfactory epithelium in nasal cavities 2, 3, and 4 indicating incomplete but progressive ongoing reversal of epithelial degeneration following a 14-day recovery period. There was complete reversal of all other microscopic changes noted previously in the nasal cavities of Main rats following a 14-day recovery period including reversal of epithelial hyperplasia, squamous metaplasia, mononuclear infiltrate, erosion, and lumen exudate.

Other microscopic findings in both the Main and Recovery groups were considered to be procedure-related or incidental as they were not dose-related, of low incidence or severity, and/or as they were also seen in the control animals.

Toxicokinetics

Over the dose range, exposure to 5MeODMT (based on the area under the plasma drug concentration-time curve from the time of dosing to the last quantifiable concentration [$AUC_{0-Tlast}$] values) on Days 1 and 14 generally increased dose-dependently (except for Group 4 as stated below), but not consistently in a dose-proportional manner as some increases were more or less than dose-proportional between different doses. Furthermore, on Day 14, the exposure in Female group 4 (75 mg/kg/day) decreased compared to Female Group 3 (20 mg/kg/day).

The sex ratios ranged between 0.4 and 6.2, but as the sex ratio randomly varied between dose groups and occasions, it was considered there was no sex-related difference.

Accumulation ratios (based on $AUC_{0-Tlast}$) ranged sporadically from 0.3 to 2.9 (Day 14/Day 1) suggesting that 5MeODMT does not accumulate when administered once daily for 14 consecutive days (2 weeks) by intranasal instillation in the Sprague Dawley rats at doses up to 75 mg/kg/days.

The mean toxicokinetic parameters for Groups 2, 3, and 4 are presented in Table 8.

TABLE 8

Mean Toxicokinetic Parameters From Study 700041

| Group | Dose (mg/kg/day) | Parameter | Day 1 Male | Day 1 Female | Day 14 Male | Day 14 Female |
|---|---|---|---|---|---|---|
| 2 | 5 | $T_{max}$ (h) | 0.0833 | 0.166 | 0.0833 | 0.0333 |
| | | $AUC_{0-Tlast}$ [SE] | 39.9 [7.35] | 53.2 [15.9] | 114 [13.8] | 63.8 [4.55] |
| | | ($AUC_{INF\_obs}$) (h*ng/mL) | (40.1) | (53.7) | (115) | (64.0) |
| | | $C_{max}$ [SE] (ng/mL) | 191 [45.6] | 186 [98.7] | 627 [102] | 645 [106] |
| | | $t_{1/2}$ (h) | 0.137 | 0.150 | 0.142 | 0.113 |
| 3 | 20 | $T_{max}$ (h) | 0.0333 | 0.0833 | 0.0333 | 0.0833 |
| | | $AUC_{0-Tlast}$ [SE] | 420 [62.1] | 198 [15.2] | 133 [57.2] | 169 [21.2] |
| | | ($AUC_{INF\_obs}$) (h*ng/mL) | (421) | (198) | (133) | (169) |
| | | $C_{max}$ [SE] (ng/mL) | 4190 [1040] | 679 [162] | 1200 [857] | 795 [115] |
| | | $t_{1/2}$ (h) | 0.125 | 0.140 | 0.143 | 0.147 |
| 4 | 75 | $T_{max}$ (h) | 0.0333 | 0.0333 | 0.0333 | 0.0333 |
| | | $AUC_{0-Tlast}$ [SE] | 1030 [114] | 228 [49.7] | 391 [228] | 155 [53.8] |
| | | ($AUC_{INF\_obs}$) (h*ng/mL) | (1040) | (228) | (392) | (156) |
| | | $C_{max}$ [SE] (ng/mL) | 7010 [1010] | 1310 [802] | 3290 [2510] | 870 [361] |
| | | $t_{1/2}$ (h) | 0.133 | 0.156 | 0.116 | 0.130 |

Abbreviations: $AUC_{0-Tlast}$ = Area under the plasma drug concentration-time curve from the time of dosing to the last quantifiable concentration; $AUC_{INF\_obs}$ = Area under the plasma drug concentration-time curve from the time of dosing extrapolated to infinity; $C_{max}$ = The maximum plasma concentration; h = hours; SE = standard error of mean; $t_{1/2}$ = Terminal elimination half-life; $T_{max}$ = Time to maximum plasma concentration.

Conclusion

Intranasal administration of BPL-5MEO at dose levels ≤75 mg/kg/day for 14 consecutive days was tolerated with no BPL-5MEO-related effects on mortality, ophthalmology, clinical chemistry, macroscopic findings and urinalysis. Slight dose-dependent body weight gain suppression was observed for both sexes. Transient clinical signs included incoordination, shaking (or tremor), increased or shallow respiration, mydriasis, salivation, decreased activity, partially closed eyes, lying on cage floor and sensitive to touch. Male animals also exhibited erect penis. Slight dose dependent body temperature increases were observed for both sexes.

Decreases in respiratory rates were observed at 20 minutes post dose timepoint which resulted in decreases in respiratory minute volumes. Platelet, neutrophil, monocyte and basophil counts were slightly increased in mid and high dose groups in both sexes. APTT were increased for both sexes for main animals in the mid (20 mg/kg/day) and high (75 mg/kg/day) dose groups. There were decreases in thymus weights (absolute and relative to terminal bodyweight) observed in male animals. Microscopic changes were noted in nasal cavities 1, 2, 3, and/or 4 involving the respiratory, olfactory, and transitional epithelium. The incidence and severity of findings were greater in males compared to females and were proportional to the dose of BPL-5MEO with incomplete but progressive on-going reversal following a 14-day recovery period.

The NOAEL was reported as the lowest dose of 5 mg/kg.

b. A 14-Day Repeat-Dose Intranasal Toxicity Study Followed by a 14-Day Recovery Period in Dogs (Study 62959)

The objective of this GLP study (Study 62959) was to determine the toxicity and TK profile of BPL-5MEO following intranasal instillation in Beagle dogs for 14 consecutive days and to assess the persistence, delayed onset, or reversibility of any changes following a 14-day recovery period. BPL-5MEO and control/vehicle were administered to groups of dogs once daily by intranasal instillation for 14 consecutive days as described in Table 9.

in plasma and the subsequent calculation of toxicokinetic parameters. Following dosing, the Main animals were euthanized and subjected to a complete necropsy examination on Day 15. The Recovery animals were observed for an additional 14 days test article free and then euthanized and subjected to a complete necropsy examination on Day 28. All Main and Recovery study animals underwent complete necropsy examinations, selected tissues/organs were retained, and microscopic evaluations of a standard set of tissues were performed.

For toxicokinetics, a series of 8 blood samples were collected from the jugular vein from all treated animals on each of Days 1 and 14 of the treatment period at 2, 5, 10, 15, 30, and 60 minutes as well as 3 and 8 hours after treatment. For Group 1, only one sample was taken at 15 minutes post dosing on Days 1 and 14 in order to confirm the absence of BPL-5MEO in animals in the vehicle control group. Blood samples were analysed for the BPL-5MEO concentration in plasma and the subsequent calculation of TK parameters.

Results

All the dose formulation samples collected and analyzed met the acceptance criteria for accuracy (100±10% of their nominal concentration).

Daily intranasal administration of BPL-5MEO to both nostrils of Beagle dogs once daily for 14 consecutive days at dose levels up to 1.5 mg/kg/day did not cause any mortality. High dose animals initially given to a subset of dogs at 2.5 mg/kg and showed severe clinical signs of muscle stiffness (rigidity), tachycardia, tachypnea, hyperthermia and aggressiveness after dosing on Day 1 and this dose exceeded the MTD. The high dose was subsequently lowered on Day 2 to 1.5 mg/kg/day and this dose was tolerated. Animals in all treated Groups exhibited transient clinical observation of incoordination, vocalization, mydriasis, decreased or increased activity, increased respiration, gnawing cage wire, excessive licking of nose or lips and circling. In addition, eye discharge and shaking were observed in the Mid and High dose groups. Erect penis was also recorded for the high dose male animals. All these

TABLE 9

Doses Administered in 14-Day Repeat Dose Study in Dogs

| Group Number | Group Designation | Total Dose Level [b] (mg/kg/day) | Dose Conc. (mg/mL) | Dose Volume [d, e] (μL/kg) | Number of Animals | | | |
|---|---|---|---|---|---|---|---|---|
| | | | | | Main | | Recovery | |
| | | | | | Male | Female | Male | Female |
| 1 | Vehicle Control [a] | 0 | 0 | 10 Right Nostril + 10 Left Nostril | 3 | 3 | 2 | 2 |
| 2 | Low Dose | 0.4 | 20 | | 3 | 3 | — | — |
| 3 | Mid Dose | 0.8 | 40 | | 3 | 3 | — | — |
| 4 | High Dose | 2.5 & 1.5[c] | 125 & 75[c] | | 3 | 3 | 2 | 2 |

[a] Vehicle control animals were administered 0.1% Hydroxypropyl methyl cellulose (HPMC) in water.
[b] Dose levels refer to the freebase of 5MeODMT salt form.
[c] Replicate A high dose animals showed severe clinical signs of muscle stiffness (rigidity), tachycardia, tachypnea, hyperthermia and aggressiveness after dosing on Day 1 at the dose level of 2.5 mg/kg. The dose level was subsequently decreased on Day 1 for the Replicates B and C to 1.5 mg/kg. Replicate A received 1.5 mg/kg on Days 2 to 14.
[d] The dose volume administered to each animal was 10 μL/kg/nostril.
[e] Dose volume was not to exceed 100 μL/nostril for all animals regardless of their bodyweight.

Assessments of mortality, clinical signs, olfactory reflex, body weights, food consumption, ophthalmology, and electrocardiograms were performed. In addition, clinical pathology assessments (hematology, coagulation, clinical chemistry and urinalysis) were evaluated once pretreatment and at termination. Blood samples were collected from the jugular vein of all animals on Days 1 and 14, at up to 8 time points relative to treatment, for analysis of test item concentration clinical signs were considered to be exacerbated pharmacology manifestations, occurred within 10 to 30 minutes of dosing, and were resolved within 90 minutes.

When compared to control Group, the triglyceride level of 1/3 Group 3 female, 1/5 Group 4 male and 4/5 Group 4 females were increased, these data are presented in Table 10. There were no other treatment-related clinical pathology findings.

TABLE 10

Mean ± SD Day 14 Triglyceride Values Compared to Control Group

| Group | Dose (mg/kg/day) | Triglyceride (mmol/L) Males [a] | Triglyceride (mmol/L) Females [a] |
|---|---|---|---|
| Group 1 | Control | 0.38 ± 0.13 | 0.34 ± 0.12 |
| Group 2 | 0.4 | 0.40 ± 0.11 | 0.46 ± 0.61 |
| Group 3 | 0.8 | 0.44 ± 0.07 | 0.47 ± 0.22 |
| Group 4 | 2.5 & 1.5[b] | 0.42 ± 0.16 | 0.69 ± 0.24 |

Abbreviations: SD = standard deviation
[a] for Control group, the control value is mentioned, for other groups, the percentage compared to the control value is shown.
[b] Replicate A high dose animals showed severe clinical signs of muscle stiffness (rigidity), tachycardia, tachypnea, hyperthermia and aggressiveness after dosing on Day 1 at the dose level of 2.5 mg/kg. The dose level was subsequently decreased on Day 1 for the Replicates B and C to 1.5 mg/kg. Replicate A received 1.5 mg/kg on Days 2 to 14.

All other changes in the clinical chemistry parameters, including those that reached statistical significance, were not attributed to the administration of BPL-5MEO as they were minor (within the normal physiological range), comparable to control values, and/or not dose related.

There were no changes in olfactory reflex, food consumption, body weight, ocular effect, or ECG that could be clearly attributed to treatment with BPL-5MEO at a dose level ≤1.5 mg/kg/day for 14 days. All body weight changes were not attributed to the administration of the test item as they were minor, and not toxicologically relevant. All food consumption changes, including those that were statistically significant, were not attributed to the administration of the test item as they were minor, and not toxicologically relevant.

Animals showed hyperthermia at the dose level of 2.5 mg/kg/day on Day 1. Transient body temperature increases were observed on Day 14 for high dose group in both sexes at 15 and 30 minutes postdose. All other body temperature changes were not attributed to the administration of the test item as they were minor, and not toxicologically relevant.

Histopathological examination results for Main animals included minimal to moderate decreased cellularity of the thymic lymphocytes at dose levels of 0.8 (1 male) and 1.5 mg/kg/day (3 males), which was determined as stress related. Minimal epithelial metaplasia of respiratory epithelium in the nasal cavities found at dose levels of 0.8 (1 female) and 1.5 mg/kg/day (2 males) and minimal to mild mononuclear cell infiltrate of the olfactory epithelium in the nasal cavities seen at a dose level of 1.5 mg/kg/day (1 male/1 female) were considered to be signs of irritation caused by BPL-5MEO but not adverse.

In animals euthanized after a 14-day recovery period, only minimal mononuclear cell infiltrate of the olfactory epithelium in the nasal cavities was still present at a dose level of 1.5 mg/kg/day (1 female) but at a lower severity when compared with animals euthanized terminally, indicative of recovery. Decreased cellularity of thymic lymphocytes was no longer observed.

Toxicokinetics

BPL-5MEO was not detected in any of the samples collected from the Control (Group 1) animals on Days 1 and 14.

The mean toxicokinetic parameters for Groups 2, 3, and 4 are presented in Table 11.

TABLE 11

Mean Toxicokinetic Parameters From Study 62959

| Group | Dose (mg/kg/day) | Parameter | Day 1 Male | Day 1 Female | Day 14 Male | Day 14 Female |
|---|---|---|---|---|---|---|
| 2 | 0.4 | $T_{max}$ (h) | 0.0942 | 0.194 | 0.111 | 0.0942 |
|   |     | $AUC_{0-Tlast}$ ($AUC_{INF\_obs}$) (h*ng/mL) | 77.9 (80.9) | 104 (106) | 70.6 (77.7) | 86.4 (95.9) |
|   |     | $C_{max}$ (ng/mL) | 343 | 242 | 285 | 196 |
|   |     | $t_{1/2}$ (h) | 0.571 | 0.312 | 0.429 | 0.706 |
| 3 | 0.8 | $T_{max}$ (h) | 0.111 | 0.139 | 0.111 | 0.0833 |
|   |     | $AUC_{0-Tlast}$ ($AUC_{INF\_obs}$) (h*ng/mL) | 152 (160) | 261 (265) | 298 (322) | 248 (279) |
|   |     | $C_{max}$ (ng/mL) | 300 | 328 | 411 | 244 |
|   |     | $t_{1/2}$ (h) | 0.595 | 0.730 | 1.32 | 1.59 |
| 4 | 2.5 & 1.5[a] | $T_{max}$ (h) | 0.146 | 0.111 | 0.223 | 0.0898 |
|   |     | $AUC_{0-Tlast}$ ($AUC_{INF\_obs}$) (h*ng/mL) | 277 (280) | 263 (271) | 260 (287) | 165 (167) |
|   |     | $C_{max}$ (ng/mL) | 561 | 348 | 464 | 379 |
|   |     | $t_{1/2}$ (h) | 0.718 | 0.848 | 0.816 | 0.725 |

Abbreviations: $AUC_{0-Tlast}$ = Area under the plasma drug concentration-time curve from the time of dosing to the last quantifiable concentration; $AUC_{INF\_obs}$ = Area under the plasma drug concentration-time curve from the time of dosing extrapolated to infinity; $C_{max}$ = The maximum plasma concentration; h = hours; $t_{1/2}$ = Terminal elimination half-life; $T_{max}$ = Time to maximum plasma concentration.
[a] Replicate A high dose animals showed severe clinical signs of muscle stiffness (rigidity), tachycardia, tachypnea, hyperthermia and aggressiveness after dosing on Day 1 at the dose level of 2.5 mg/kg. The dose level was subsequently decreased on Day 1 for the Replicates B and C to 1.5 mg/kg. Replicate A received 1.5 mg/kg on Days 2 to 14.

Over the dose range, exposure to BPL-5MEO (based on $AUC_{0-Tlast}$ values) on Days 1 and 14 generally increased dose-dependently (except for Group 4 as stated below), but not consistently in a dose-proportional manner as some increases were more or less than dose-proportional between different doses. Furthermore, on Day 14, the exposure in Group 4 (1.5 mg/kg/day) decreased compared to Group 3 (0.8 mg/kg/day).

There were no marked sex-related differences in any of the measured toxicokinetic parameters, except on Day 14 where $T_{max}$ occurred slightly later in Group 4 males as compared to Group 4 females. The sex ratios (male/female), with the exception of Group 4 $T_{max}$, ranged sporadically from 0.5 to 1.7 on Days 1 and 14.

Accumulation ratios (based on $AUC_{0-Tlast}$) ranged sporadically from 0.6 to 2.0 (Day 14/Day 1) suggesting that BPL-5MEO does not accumulate when administered once daily for 14 consecutive days (2 weeks) by intranasal instillation in beagle dogs at doses up to 1.5 mg/kg/day.

Conclusion

Based on the parameters examined where all the changes noted were considered either non-adverse or related to exaggerated pharmacological effects, the reported NOAEL for BPL-5MEO, when dosed for 14 consecutive days by intranasal administration, followed by a 14-day recovery period was considered to be 1.5 mg/kg/day, corresponding to a $C_{max}$ of 421 ng/mL, and $AUC_{0\text{-}Tlast}$ ($AUC_{INF\_obs}$) of 213 (220) h*ng/mL (combined for both sexes).

Toxicokinetic Considerations

Based on preliminary data from another ongoing study in dogs, it has been observed that the site of blood sampling in dogs may impact the measured plasma exposure. Samples from the jugular vein may result in higher apparent exposure levels than samples from the cephalic vein, which might be due to the local transmucosal route of administration (also reported in the scientific literature (Illum, 2003; Sohlberg, 2013)). Therefore, dose escalation criteria for the Phase 1 Single Ascending Dose study are based on assessment of clinical criteria, safety factors and exposure. A maximum dose of 14 mg has been designated. Table 12 summarizes the clinical observations in the rat and dog toxicity studies performed with BPL-5MEO. These clinical signs are considered to be related to the pharmacological activity of BPL-5MEO and demonstrate a dose-related increase in severity of findings on both species, generally ranging from mild to moderate at 0.4 to 1.5 mg/kg in dogs and 1.5 to 5 mg/kg in rats.

TABLE 12

Summary of Clinical Observations in Applicant-Sponsored Animal Studies

Dog (HED)

| 0.4 mg/kg (14 mg) | 0.8 mg/kg (26 mg) | 1.5 mg/kg[a] (50 mg) | 2.5 mg/kg (83 mg) | 3.0-5.0 mg/kg (100-166 mg) |
|---|---|---|---|---|
| Salivation | Mydriasis | Mydriasis | Salivation | Mydriasis |
| Mydriasis | Salivation | Salivation, | Pupil dilated | Salivation |
| Incoor-dination | Excessive licking | Excessive licking | Circling Muscle | Excessive licking |
| Vocalization | Incoor-dination | Dilated pupil | stiffness Activity | Dilated pupil Vocalizing |
| Decreased activity | Vocalization | Vocalizing | decreased | Labored |
| Increased activity | Decreased activity | Tachypnea Increased | Increased respiration | respiration Gnawing |
| Increased respiration | Increased activity | respiration Tachycardia | Diarrhea Hunched | cage Tongue |
| Gnawing cage wire | Increased respiration | Muscle rigidity | Erect penis Excessive | outside Hunched |
| Excessive licking | Gnawing cage wire | Erect penis Twitches | grooming Excessive | Erect penis Tremor |
| Circling | Circling Eye | Tense abdomen | fear Hyper- | Shaking Lying |
| | discharge Shaking | Splay posture | sensitive to stimuli | Decreased activity |
| | Head shaking | Lying on cage | Aggressive-ness | Uncoordinated Aggressive- |
| | Slight tremor | floor Uncoor- | Tachycardia Loss of | ness Circling |
| | (1.0 mg/kg)[b] | dinated Circling | righting reflex | Not responsive to stimuli |
| | | Head shaking | Hyperthermia (single dose) | Hyperthermia Convulsion |
| | | Tremor Myoclonic jerk[b] | Shaking Tremors | |

Rat (HED)

| 1.5 mg/kg (14 mg) | 3.0 mg/kg (29 mg) | 5.0 mg/kg[a] (48 mg) | 10 mg/kg (96 mg) | 20-75 mg/kg (194-726 mg) |
|---|---|---|---|---|
| Salivation | Salivation | Salivation | Salivation | Increased |
| Piloerection | Piloerection | Piloerection | Piloerection | respiration |
| Increased respiration | Increased respiration | Increased respiration | Decreased activity | Shallow respiration |

TABLE 12-continued

Summary of Clinical Observations in Applicant-Sponsored Animal Studies

| Dilated pupils | Gasping Dilated | Dilated pupils | Increased or shallow | Mydriasis Salivation |
|---|---|---|---|---|
| Decreased activity | pupils Decreased | Slight hyper- | respiration Gasping | Decreased activity |
| Decreased rearing | activity Decreased | thermia (repeated | Lying Decreased | Partially closed |
| Lying Hypo-thermia | rearing Lying | dose) Uncoor-dinated | rearing Hypothermia (single dose) | eyes Lying on cage floor |
| (single dose) | Hypo-thermia (single dose) | Shaking Decreased activity | Twitching Tremor | Sensitive to touch Erect penis |
| | Uncoor-dinated Tremor | Lying Sensitive to touch | | Hyperthermia Uncoordinated Shaking (or tremor) |

Abbreviations: HED = Human Equivalent Dose (for a 60 kg human)
[a]NOAEL determined in the 14-day toxicology studies for both species.
[b] Preliminary data, ongoing study (Slight tremor was observed at 1.0 mg/kg = 33 mg HED)
Note: these signs were of short duration, and generally resolved within one to two hours in both species.

Example 11: Genotoxicity

The genotoxicity potential of 5MeODMT was evaluated in silico (computational analysis) for structural alerts and in vitro in GLP assays to assess mutagenic and clastogenic potential following the ICH S2 (R1) Guidance.

In Silico

5MeODMT, its primary active metabolite, bufotenine, and an identified drug substance impurity, MW234, were evaluated for quantitative structural activity relationships for potential mutagenicity and/or carcinogenicity using two computation analytical methods, Derek Nexus and the Leadscope Genetox Statistical Models. The evaluation from both analyses did not identify any structural alerts associated with 5MeODMT or bufotenine, and a possible nor an identified drug substance impurity MW234.

In Vitro Mutagenicity

The mutagenic potential of 5MeODMT was evaluated in a GLP Bacterial Reverse Mutation Test (Ames test) for the ability to induce reverse mutations at selected loci of *Salmonella typhimurium* tester strains TA98, TA100, TA1535, and TA1537 and the *Escherichia coli* tester strain WP2uvrA. These strains were treated with 5MeODMT at concentrations of 1.6, 5, 16, 50, 160, 500, 1600 and 5000 m per plate along with the vehicle/negative and appropriate positive controls. The assay was performed in triplicate using the pre-incubation method in the absence and presence of an exogenous metabolic activation system, phenobarbital/5,6-benzoflavone-induced rat liver S9 microsomal enzyme mix (S9 mix)

A slight cytotoxicity was seen at the concentration of 1600 m/plate in all *S. typhimurium* strains. Although higher levels of cytotoxicity were observed at 5000 µg/plate in the absence of S9 mix, it remained slight in the presence of S9 mix in these strains. No cytotoxicity was noted in the *E. coli* strain in either the absence or presence of S9 mix.

Overall, no increases (≥2× of the vehicle/negative values) in the number of revertant colonies per plate was observed with 5MeODMT in *S. typhimurium* tester strains TA1535, TA100, *E. coli* WP2uvrA in either the absence and presence of S9 or with TA1537 and TA98 in the presence of S9 mix. Three exceptions were a 2.1-fold increase at 1600 m/plate without S9 seen in *E. coli* WP2uvrA, a 2.0-fold increase in S. typhimurium TA1537 at 50 µg/plate with S9, and 2.1-fold increase in S. typhimurium TA1535 at 1600 m/plate with S9. However, these values were not considered biologically relevant as the values were within laboratory's historical vehicle/negative control range and were not dose-related. Two of the 5MeODMT-treated S. typhimurium strains, TA1537 and TA98, in the absence of S9 mix, showed a number of revertant colony counts slightly higher than twice of the vehicle/negative values at 160 µg/plate and 500 µg/plate with fold-increases at 2.3- and 2.7-fold in TA1537 and 2.2- and 2.4-fold in TA98. The increased colony counts observed in these strains were still within the laboratory's historical vehicle/negative control range and were not overall dose-related; therefore, they did not meet the criteria of positive results. However, as the increases were seen in TA98 and TA1537 in 2 adjacent dose levels and that 2 strains showed a similar trend of increases in revertant colony counts at the same concentration levels, the results were judged equivocal. Therefore, the bacterial reverse mutation test was repeated in the absence of S9 mix for these 2 strains in order to investigate these equivocal results. The repeat test used a narrower concentration range of 15, 30, 60, 120, 250, 500, 1000, and 2000 µg per plate. The results from repeated test showed no increases in the revertant colonies number per plate for both 5MeODMT-treated strains in all concentration levels tested up to the maximal dose of 2000 m/plate. Therefore, it was concluded that the small increases observed in the first test for S. typhimurium tester stains TA 1537 and TA98 were not biologically relevant.

In conclusion, the results of the bacterial reverse mutation assays indicated that 5MeODMT did not induce any increase in revertant colony numbers with any of the bacteria strains tested either in the absence or presence of the rat liver S9 microsomal metabolic activation system. 5MeODMT has no mutagenic potential in the bacterial reverse mutation test. The expected response of the positive and negative controls affirmed the sensitivity and validity of assay.

In Vitro Clastogenicity

The clastogenic potential of 5MeODMT was evaluated in a GLP in vitro micronucleus test using Chinese hamster ovary (CHO)-K1 cells using flow cytometry. Exponentially growing cells were treated in duplicate with the 5MeODMT at 9 concentrations up to the recommended upper limit of 1 mM (corresponding to approximately 300 µg/mL): 1.25, 2.5, 5.0, 10, 20, 40, 80, 150 and 300 µg/mL. The treatment with the vehicle/negative and positive controls was concurrently performed. There were 3 treatment regimens: a 4-hour-short exposure in either absence or presence of an exogenous metabolic activation system, phenobarbital/5,6 benzoflavone rat liver S9 microsomal enzyme mix (S9 mix), and a 26 hour-extended exposure, considered a confirmatory phase, in the absence of S9 mix.

No cytotoxicity or precipitation was observed in 5MeODMT-treated cells up to the maximal dose level of 300 µg/mL throughout the treatment periods. In all treatment regimens, the results of the in vitro micronucleus test indicate that 5MeODMT did not induce any increases in micronuclei or hypodiploid cells either in the absence or presence of the rat liver S9 microsomal metabolic activation system. In conclusion, 5MeODMT showed no chromosome-damaging potential in the in vitro micronucleus test with CHO-K1 cells. The expected response of the positive and negative controls affirmed the sensitivity and validity of assay.

Reproductive and Development Toxicity

Reproductive and developmental toxicity studies have not been conducted. In the 14-day pivotal GLP intranasal toxicity studies in rats and dogs, there was no evidence of an adverse effect on reproductive tissues with systemic exposure to BPL-5MEO.

Example 12: Formulation

BPL-5MEO has been synthesised to Good Manufacturing Practice (GMP) standards and prefilled into the Aptar Unidose Intranasal Liquid Delivery System device. The device allows a single fixed dose of BPL-5MEO to be administered intranasally. The liquid is prefilled into and administered using a standard single unit dose nasal pump device. Excipients used in the formulation are water, 0.1% hydroxypropyl methylcellulose (HPMC) and sodium hydroxide (NaOH). Two concentrations of the formulation will be used, 70 mg/mL (for dose levels below 7 mg), and 140 mg/mL (for dose levels above 7 mg).

In one embodiment, there is provided a composition comprising 5MeODMT hydrochloride, wherein the composition comprises:
Water;
0.1% hydroxypropyl methylcellulose (HPMC);
0.1% sodium hydroxide (NaOH); and
70 mg/ml 5MeODMT.

In one embodiment, there is provided a composition comprising 5MeODMT hydrochloride, wherein the composition comprises:
Water;
0.1% hydroxypropyl methylcellulose (HPMC);
0.1% sodium hydroxide (NaOH); and
140 mg/ml 5MeODMT.

In one embodiment, there is provided an intranasal composition comprising 5MeODMT hydrochloride, wherein the composition comprises:
Water;
0.1% hydroxypropyl methylcellulose (HPMC);
0.1% sodium hydroxide (NaOH); and
70 mg/ml 5MeODMT.

In one embodiment, there is provided an intranasal composition comprising 5MeODMT hydrochloride, wherein the composition comprises:
Water;
0.1% hydroxypropyl methylcellulose (HPMC);
0.1% sodium hydroxide (NaOH); and
140 mg/ml 5MeODMT.

In one embodiment, the composition comprises 25-400 mg/mL; 25-300 mg/mL; 25-200 mg/mL; 25-100 mg/mL; 25-50 mg/mL; 50-400 mg/mL; 50-300 mg/mL; 60-400 mg/mL; 60-300 mg/mL; 150-400 mg/mL; 150-300 mg/mL; 200-300 mg/mL; 200-400 mg/mL; 30-100 mg/mL; 300-400 mg/mL; 300-500 mg/mL; 45-75 mg/mL; 50-70 mg/mL; 55-65 mg/mL; or 50-60 mg/mL 5MeODMT.

In one embodiment, there is provided an intranasal liquid delivery system comprising a composition of 5MeODMT.

In one embodiment, there is provided a single unit dose capsule of a composition of 5MeODMT.

Example 13: Administration

BPL-5MEO is administered to subjects by a trained member of the research team using a single unit dose pump spray. The unit contains only 1 spray, so should not be tested before use. While sitting down the subject is asked to blow their nose to clear the nasal passages. Once the tip of the device is placed into the nostril the clinic staff will press the plunger to release the dose.

In one embodiment, there is provided a method for the administration of 5MeODMT comprising administering the 5MeODMT as an instranasal spray to a human subject wherein the human subject has followed patient preparation parameters that include blowing their nose to clear their nasal passages immediately prior to administration.

In one embodiment, the human subject is seated.

In one embodiment, there is provided a method for the delivery of 5MeODMT to the brain of a human subject comprising administering the 5MeODMT as an instranasal spray to a human subject wherein the human subject has followed patient preparation parameters that include blowing their nose to clear their nasal passages immediately prior to administration.

Example 14: X-Ray Powder Diffractogram (XRPD) Analysis

Figure 4:
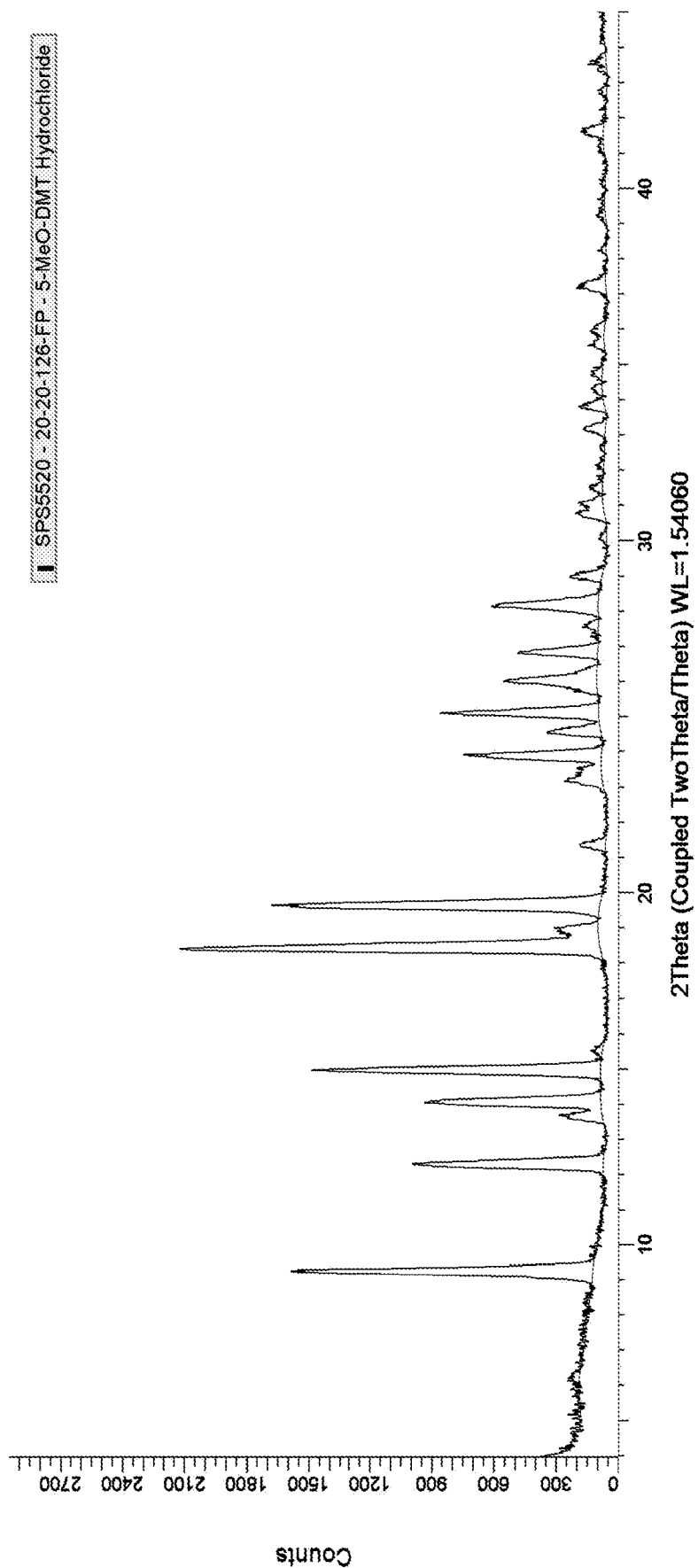
FIG. 4 shows an XRPD diffractogram for 5MeODMT hydrochloride lot 20/20/126-FP.
Figure 5:
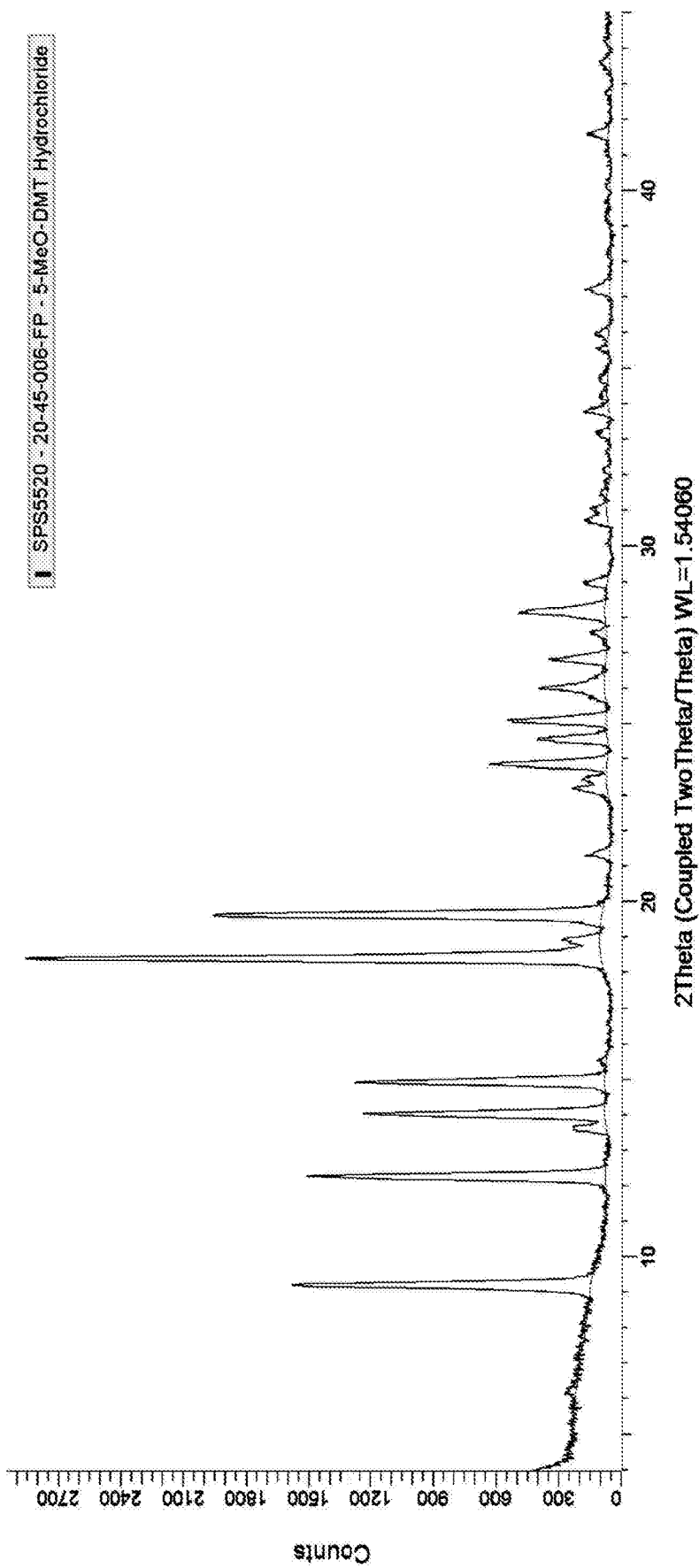
FIG. 5 shows an XRPD diffractogram for 5MeODMT hydrochloride lot 20/45/006-FP.
Figure 6:
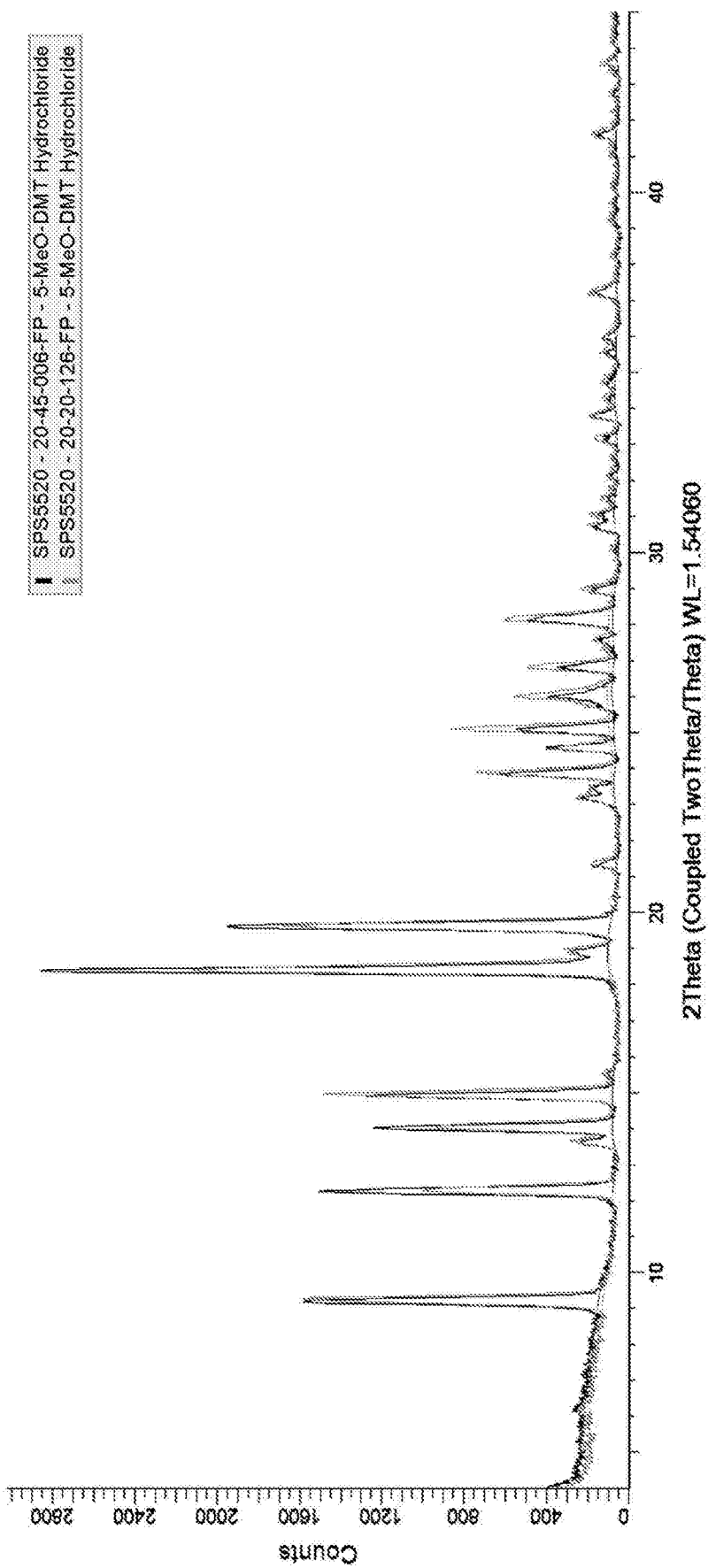
FIG. 6 shows the XRPD diffractogram of FIGS. 4 and 5 overlaid on top of one another.

XRPD analysis of two lots of 5MeODMT hydrochloride (lot 20/20/126-FP and lot 20/45/006-FP) was performed, both were of well-ordered material with moderate relative crystallinity and exhibited the same crystalline pattern, which can be seen in FIGS. 4-6. In the absence of any other known sample label, the pattern was assigned as 5MeODMT Hydrochloride Pattern A. In one embodiment, there is provided crystalline 5MeODMT hydrochloride, characterised by peaks in an XRPD diffractogram at 9.2, 12.2, 14.1, 15.0, 18.5 and 19.5°2θ±0.1°2θ.

In one embodiment, there is provided crystalline 5MeODMT hydrochloride, characterised by peaks in an XRPD diffractogram at 9.2, 12.2, 14.1, 15.0, 18.5 and 19.5°2θ±0.2°2θ.

In one embodiment, there is provided crystalline 5MeODMT hydrochloride, characterised by peaks in an XRPD diffractogram at 9.2, 12.2, 14.1, 15.0, 18.5 and 19.5°2θ±0.3°2θ.

In one embodiment, there is provided crystalline 5MeODMT hydrochloride, characterised by peaks in an XRPD diffractogram at 9.2, 12.2, 14.1, 15.0, 18.5 and 19.5°2θ±0.1°2θ as measured by x-ray powder diffraction using an x-ray wavelength of 1.5406 Å.

In one embodiment, there is provided crystalline 5MeODMT hydrochloride, characterised by peaks in an XRPD diffractogram at 9.2, 12.2, 14.1, 15.0, 18.5 and 19.5°2θ±0.2°2θ as measured by x-ray powder diffraction using an x-ray wavelength of 1.5406 Å.

In one embodiment, there is provided crystalline 5MeODMT hydrochloride, characterised by peaks in an XRPD diffractogram at 9.2, 12.2, 14.1, 15.0, 18.5 and 19.5°2θ±0.3°2θ as measured by x-ray powder diffraction using an x-ray wavelength of 1.5406 Å.

In one embodiment, there is provided crystalline 5MeODMT hydrochloride, characterised by peaks in an XRPD diffractogram at 9.2, 12.2, 14.1, 15.0, 18.5, 19.5, 23.9, 24.5, 25.1, 26.0, 26.9 and 28.3°2θ±0.1°2θ.

In one embodiment, there is provided crystalline 5MeODMT hydrochloride, characterised by peaks in an XRPD diffractogram at 9.2, 12.2, 14.1, 15.0, 18.5, 19.5, 23.9, 24.5, 25.1, 26.0, 26.9 and 28.3°2θ±0.2°2θ.

In one embodiment, there is provided crystalline 5MeODMT hydrochloride, characterised by peaks in an XRPD diffractogram at 9.2, 12.2, 14.1, 15.0, 18.5, 19.5, 23.9, 24.5, 25.1, 26.0, 26.9 and 28.3°2θ±0.3°2θ.

In one embodiment, there is provided crystalline 5MeODMT hydrochloride, characterised by peaks in an XRPD diffractogram at 9.2, 12.2, 14.1, 15.0, 18.5, 19.5, 23.9, 24.5, 25.1, 26.0, 26.9 and 28.3°2θ±0.1°2θ as measured by x-ray powder diffraction using an x-ray wavelength of 1.5406 Å.

In one embodiment, there is provided crystalline 5MeODMT hydrochloride, characterised by peaks in an XRPD diffractogram at 9.2, 12.2, 14.1, 15.0, 18.5, 19.5, 23.9, 24.5, 25.1, 26.0, 26.9 and 28.3°2θ±0.2°2θ as measured by x-ray powder diffraction using an x-ray wavelength of 1.5406 Å.

In one embodiment, there is provided crystalline 5MeODMT hydrochloride, characterised by peaks in an XRPD diffractogram at 9.2, 12.2, 14.1, 15.0, 18.5, 19.5, 23.9, 24.5, 25.1, 26.0, 26.9 and 28.3°2θ±0.3°2θ as measured by x-ray powder diffraction using an x-ray wavelength of 1.5406 Å.

In one embodiment, there is provided crystalline 5MeODMT hydrochloride, characterised by peaks in an XRPD diffractogram at 9.2, 12.2, 13.7, 14.1, 15.0, 18.5, 19.0, 19.5, 21.2, 23.3, 23.9, 24.5, 25.1, 26.0, 26.9, 27.5, 28.3, 29.0, 30.9 and 31.1°2θ±0.1°2θ.

In one embodiment, there is provided crystalline 5MeODMT hydrochloride, characterised by peaks in an XRPD diffractogram at 9.2, 12.2, 13.7, 14.1, 15.0, 18.5, 19.0, 19.5, 21.2, 23.3, 23.9, 24.5, 25.1, 26.0, 26.9, 27.5, 28.3, 29.0, 30.9 and 31.1°2θ±0.1°2θ.

In one embodiment, there is provided crystalline 5MeODMT hydrochloride, characterised by peaks in an XRPD diffractogram at 9.2, 12.2, 13.7, 14.1, 15.0, 18.5, 19.0, 19.5, 21.2, 23.3, 23.9, 24.5, 25.1, 26.0, 26.9, 27.5, 28.3, 29.0, 30.9 and 31.1°2θ±0.2°2θ.

In one embodiment, there is provided crystalline 5MeODMT hydrochloride, characterised by peaks in an XRPD diffractogram at 9.2, 12.2, 13.7, 14.1, 15.0, 18.5, 19.0, 19.5, 21.2, 23.3, 23.9, 24.5, 25.1, 26.0, 26.9, 27.5, 28.3, 29.0, 30.9 and 31.1°2θ±03°2θ.

In one embodiment, there is provided crystalline 5MeODMT hydrochloride, characterised by peaks in an XRPD diffractogram at 9.2, 12.2, 13.7, 14.1, 15.0, 18.5, 19.0, 19.5, 21.2, 23.3, 23.9, 24.5, 25.1, 26.0, 26.9, 27.5, 28.3, 29.0, 30.9 and 31.1°2θ±0.1°2θ as measured by x-ray powder diffraction using an x-ray wavelength of 1.5406 Å.

In one embodiment, there is provided crystalline 5MeODMT hydrochloride, characterised by peaks in an XRPD diffractogram at 9.2, 12.2, 13.7, 14.1, 15.0, 18.5, 19.0, 19.5, 21.2, 23.3, 23.9, 24.5, 25.1, 26.0, 26.9, 27.5, 28.3, 29.0, 30.9 and 31.1°2θ±0.2°2θ as measured by x-ray powder diffraction using an x-ray wavelength of 1.5406 Å.

In one embodiment, there is provided crystalline 5MeODMT hydrochloride, characterised by peaks in an XRPD diffractogram at 9.2, 12.2, 13.7, 14.1, 15.0, 18.5, 19.0, 19.5, 21.2, 23.3, 23.9, 24.5, 25.1, 26.0, 26.9, 27.5, 28.3, 29.0, 30.9 and 31.1°2θ±0.3°2θ as measured by x-ray powder diffraction using an x-ray wavelength of 1.5406 Å.

In one embodiment, there is provided crystalline 5MeODMT hydrochloride, characterised by peaks in an XRPD diffractogram as substantially illustrated in FIG. 4, 5 or 6.

In one embodiment, there is provided crystalline 5MeODMT hydrochloride, characterised by peaks in an XRPD diffractogram as substantially illustrated in FIG. 4.

In one embodiment, there is provided crystalline 5MeODMT hydrochloride, characterised by peaks in an XRPD diffractogram as substantially illustrated in FIG. 5.

In one embodiment, there is provided crystalline 5MeODMT hydrochloride, characterised by peaks in an XRPD diffractogram as substantially illustrated in FIG. 6. In one embodiment, there is provided crystalline 5MeODMT hydrochloride, characterised by one or more of: Peaks in an XRPD diffractogram as previously or subsequently described;
An endothermic event in a DSC thermograph as previously or subsequently described;
An onset of decomposition in a TGA thermograph as previously or subsequently described;
A DVS isotherm profile as previously or subsequently described; and
A crystalline structure as previously or subsequently described.

Example 15: Thermal Analysis

Differential scanning calorimetry (DSC) and thermogravimetric analysis (TGA) was performed on both lots at a standard heating rate of 10° C./Min from 30-400° C. In addition, DSC assessments of the solids were also conducted at 5, 20 and 40° C./Min heating rates. No significant differences in profile were observed between samples via DSC or TGA or via the variable DSC heating rates. An unstable DSC baseline is observed from 290° C. onwards due to rapid decomposition of the material.

Figure 7:
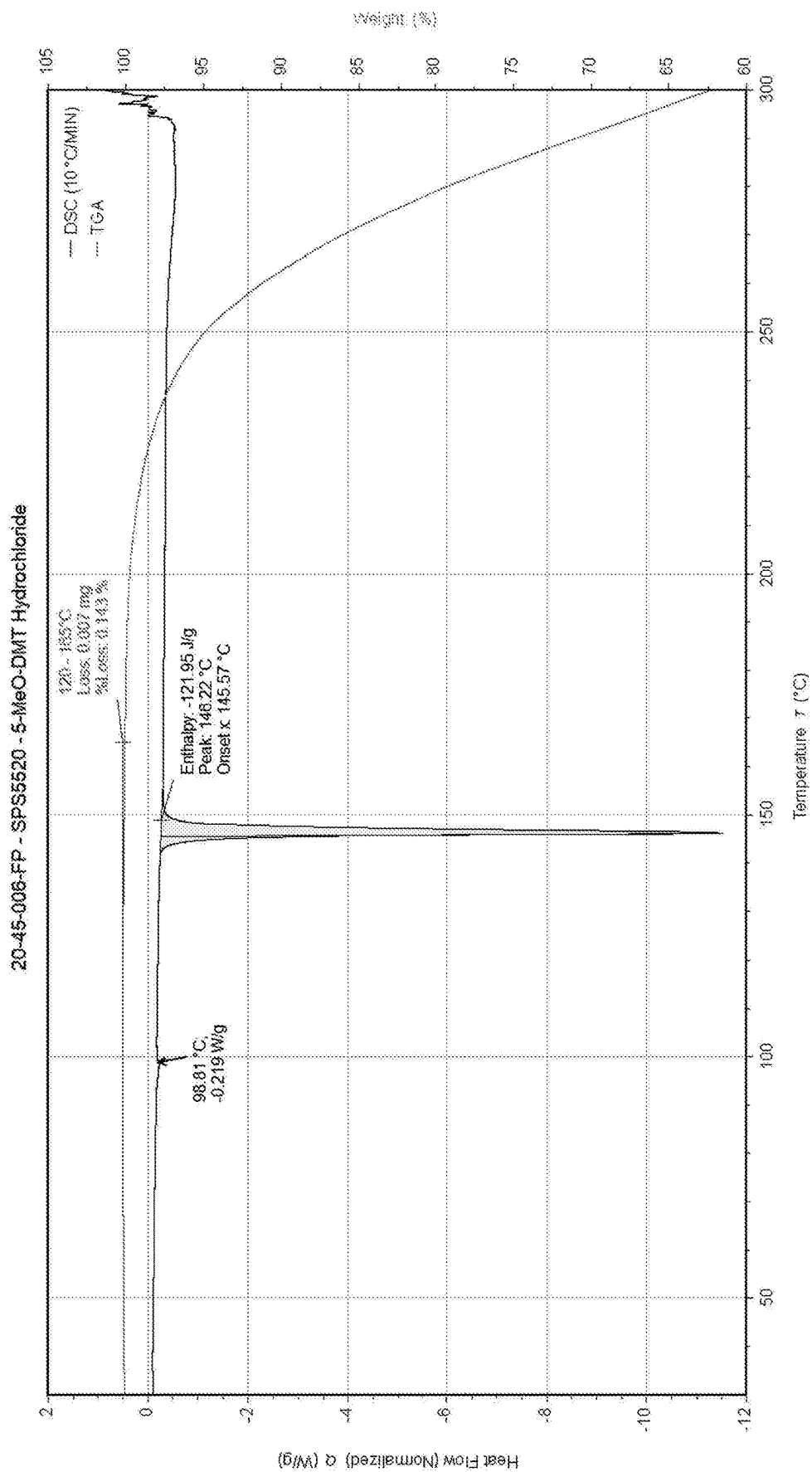
FIG. 7 shows a DSC and TGA thermograph of 5MeODMT Hydrochloride, lot 20/20/126-FP at 10° C./Min heating rate.
Figure 8:
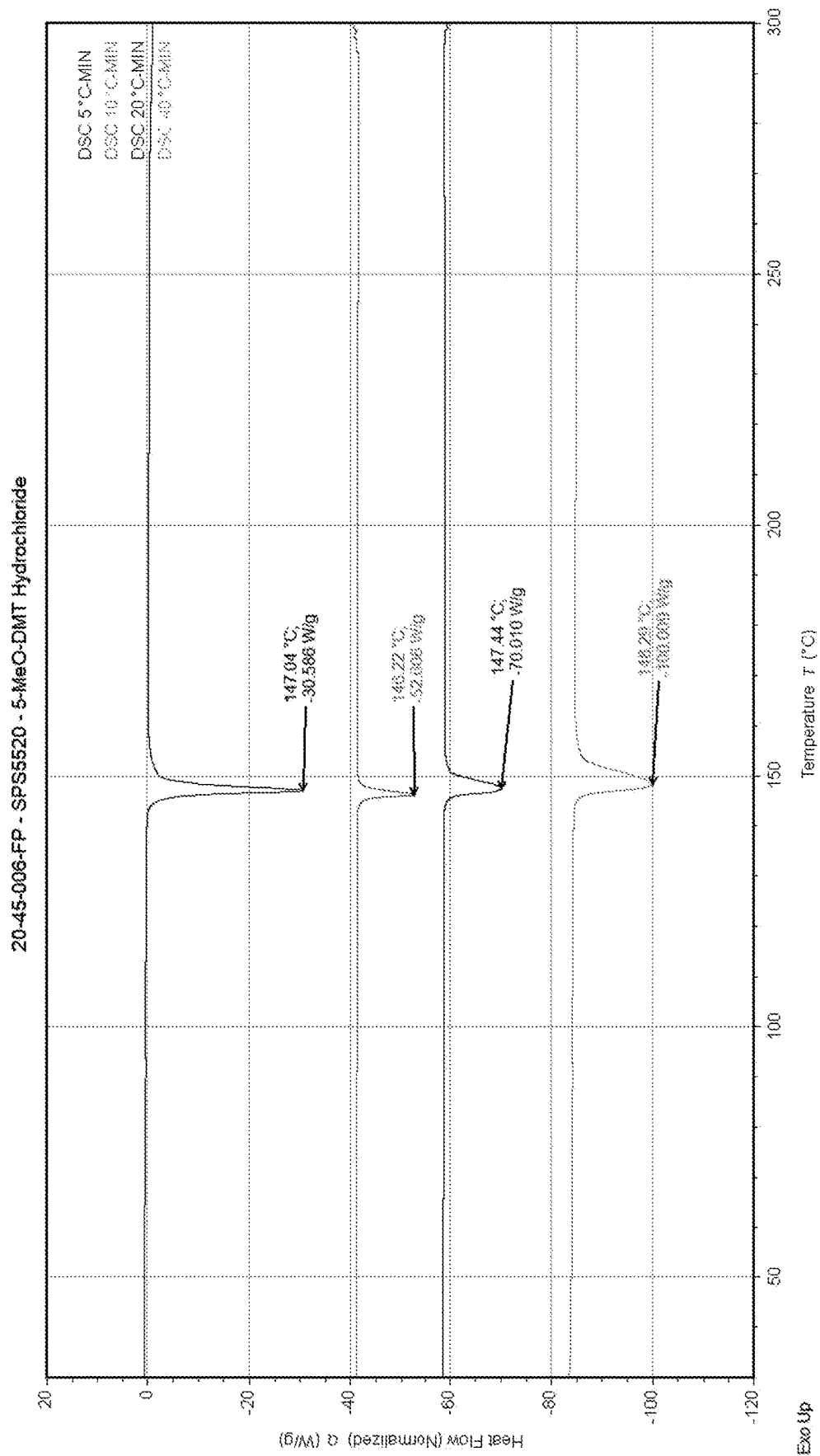
FIG. 8 shows DSC thermographs of 5MeODMT hydrochloride, lot 20/20/126-FP at 5° C./Min (Black), 10° C./Min (Red), 20° C./Min (Blue) and 40° C./Min (Green) heating rates.

FIG. 7 shows a DSC and TGA thermograph of 5MeODMT Hydrochloride, lot 20/20/126-FP at 10° C./Min heating rate. FIG. 8 shows DSC thermographs of 5MeODMT hydrochloride, lot 20/20/126-FP at 5° C./Min (Black), 10° C./Min (Red), 20° C./Min (Blue) and 40° C./Min (Green) heating rates.

Figure 9:
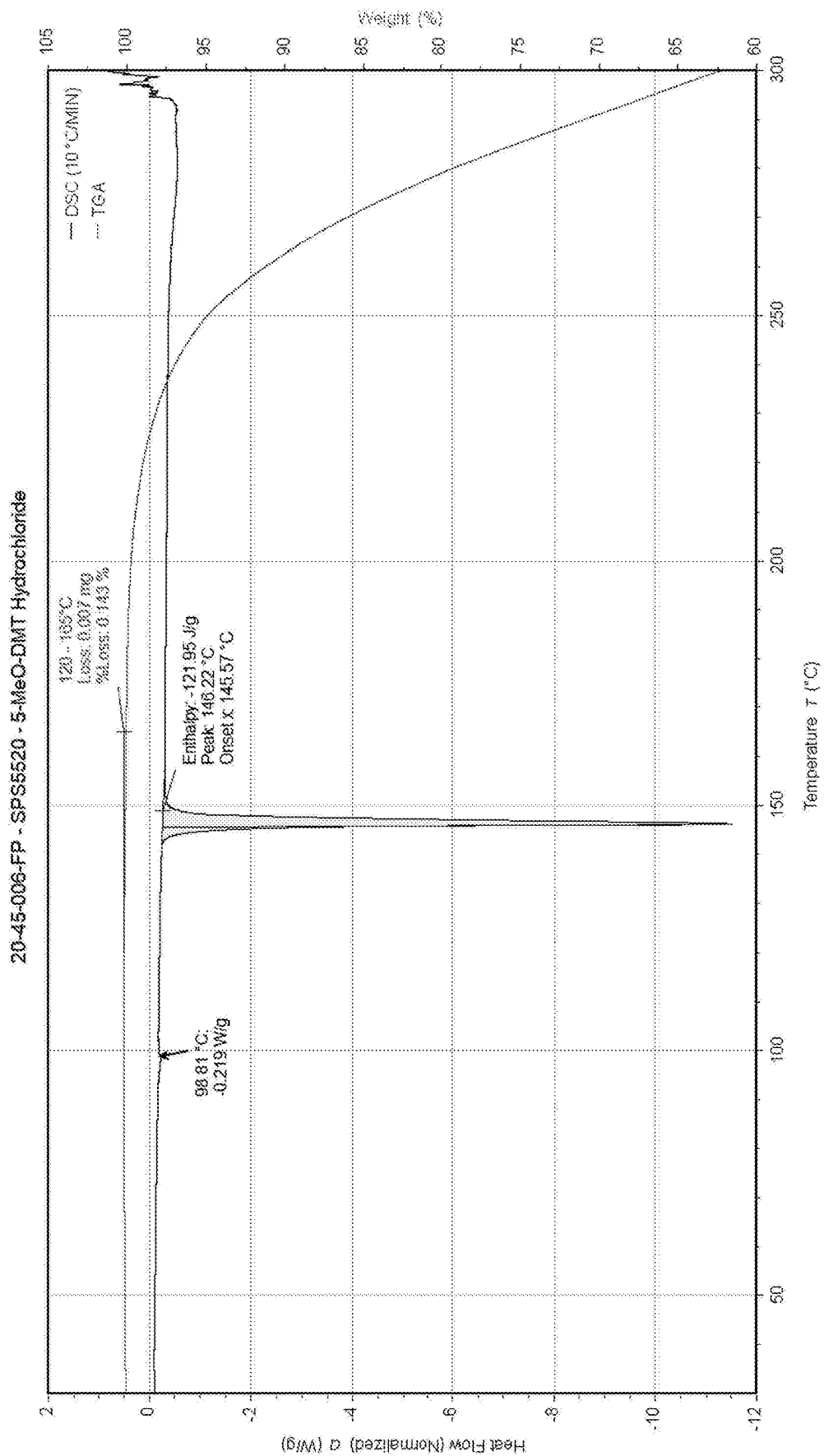
FIG. 9 shows a DSC and TGA thermograph of 5MeODMT Hydrochloride, lot 20/45/006-FP at 10° C./Min heating rate.
Figure 10:
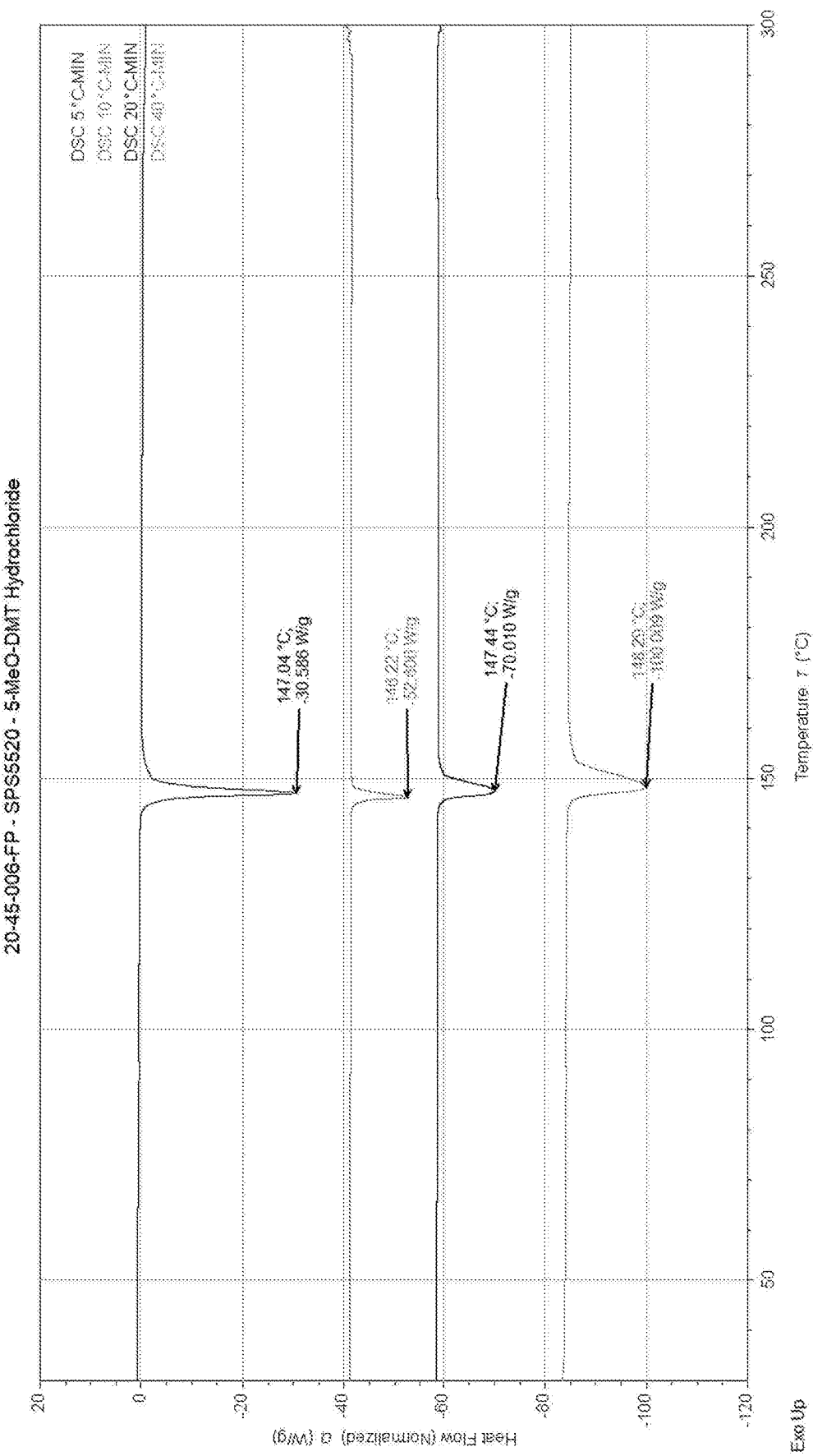
FIG. 10 shows DSC thermographs of 5MeODMT hydrochloride, lot 20/45/06-FP at 5° C./Min (Black), 10° C./Min (Red), 20° C./Min (Blue) and 40° C./Min (Green) heating rates.

FIG. 9 shows a DSC and TGA thermograph of 5MeODMT Hydrochloride, lot 20/45/006-FP at 10° C./Min heating rate. FIG. 10 shows DSC thermographs of 5MeODMT hydrochloride, lot 20/45/006-FP at 5° C./Min (Black), 10° C./Min (Red), 20° C./Min (Blue) and 40° C./Min (Green) heating rates.

In one embodiment, there is provided a crystalline 5MeODMT Hydrochloride, characterised by an endothermic event in a DSC thermograph having an onset temperature of between 140 and 150° C.

In one embodiment, there is provided a crystalline 5MeODMT Hydrochloride, characterised by an endothermic event in a DSC thermograph having an onset temperature of between 140 and 150° C., as substantially illustrated in FIG. 7 or FIG. 8.

In one embodiment, there is provided a crystalline 5MeODMT Hydrochloride, characterised by an endothermic event in a DSC thermograph having an onset temperature of 146° C.

In one embodiment, there is provided a crystalline 5MeODMT Hydrochloride, characterised by an endothermic event in a DSC thermograph having an onset temperature of 146° C. as substantially illustrated in FIG. 7 or FIG. 8.

In one embodiment, there is provided a crystalline 5MeODMT Hydrochloride, characterised by an endothermic event in a DSC thermograph having an onset temperature of between 140 and 150° C. and a peak of between 142 and 148° C.

In one embodiment, there is provided a crystalline 5MeODMT Hydrochloride, characterised by an endothermic event in a DSC thermograph having an onset temperature of between 140 and 150° C. and a peak of between 142 and 148° C. as substantially illustrated in FIG. 7 or FIG. 8.

In one embodiment, there is provided a crystalline 5MeODMT Hydrochloride, characterised by an endothermic event in a DSC thermograph having an onset temperature of 145.95° C. and a peak of 146.74° C.

In one embodiment, there is provided a crystalline 5MeODMT Hydrochloride, characterised by an endothermic event in a DSC thermograph having an onset temperature of 145.95° C. and a peak of 146.74° C. as substantially illustrated in FIG. 7 or FIG. 8.

In one embodiment, there is provided a crystalline 5MeODMT Hydrochloride, characterised by an endothermic event in a DSC thermograph having an onset temperature of between 140 and 150° C. and an enthalpy of between −113 J/g and −123 J/g.

In one embodiment, there is provided a crystalline 5MeODMT Hydrochloride, characterised by an endothermic event in a DSC thermograph having an onset temperature of between 140 and 150° C. and an enthalpy of between −113 J/g and −123 J/g as substantially illustrated in FIG. 7 or FIG. 8.

In one embodiment, there is provided a crystalline 5MeODMT Hydrochloride, characterised by an endothermic event in a DSC thermograph having an onset temperature of between 140 and 150° C., a peak of between 142 and 148° C. and an enthalpy of between −113 J/g and −123 J/g.

In one embodiment, there is provided a crystalline 5MeODMT Hydrochloride, characterised by an endothermic event in a DSC thermograph having an onset temperature of between 140 and 150° C., a peak of between 142 and 148° C. and an enthalpy of between −113 J/g and −123 J/g as substantially illustrated in FIG. 7 or FIG. 8.

In one embodiment, there is provided a crystalline 5MeODMT Hydrochloride, characterised by an endothermic event in a DSC thermograph having an onset temperature of 145.95° C., a peak of 146.74° C. and an enthalpy of −118.29/g.

In one embodiment, there is provided a crystalline 5MeODMT Hydrochloride, characterised by an endothermic event in a DSC thermograph having an onset temperature of 145.95° C., a peak of 146.74° C. and an enthalpy of −118.29/g as substantially illustrated in FIG. 7 or FIG. 8.

In one embodiment, there is provided a crystalline 5MeODMT Hydrochloride, characterised by an onset of decomposition in a TGA thermograph of between 120 and 165° C.

In one embodiment, there is provided a crystalline 5MeODMT Hydrochloride, characterised by an onset of decomposition in a TGA thermograph of between 120 and 165° C. as substantially illustrated in FIG. 7.

In one embodiment, there is provided a crystalline 5MeODMT Hydrochloride, characterised by one or more of:
an endothermic event in a DSC thermograph having an onset temperature of between 140 and 150° C.; and
an onset of decomposition in a TGA thermograph of between 120 and 165° C.

In one embodiment, there is provided a crystalline 5MeODMT Hydrochloride, characterised by one or more of:
an endothermic event in a DSC thermograph having an onset temperature of between 140 and 150° C. as substantially illustrated in FIG. 7 or FIG. 8; and
an onset of decomposition in a TGA thermograph of between 120 and 165° C., as substantially illustrated in FIG. 7.

In one embodiment, there is provided a crystalline 5MeODMT Hydrochloride, characterised by one or more of:

an endothermic event in a DSC thermograph having an onset temperature of between 140 and 150° C., a peak of between 142 and 148° C.; and
an onset of decomposition in a TGA thermograph of between 120 and 165° C.

In one embodiment, there is provided a crystalline 5MeODMT Hydrochloride, characterised by one or more of:
an endothermic event in a DSC thermograph having an onset temperature of between 140 and 150° C., a peak of between 142 and 148° C. as substantially illustrated in FIG. 7 or FIG. 8; and
an onset of decomposition in a TGA thermograph of between 120 and 165° C. as substantially illustrated in FIG. 7.

In one embodiment, there is provided a crystalline 5MeODMT Hydrochloride, characterised by one or more of:
an endothermic event in a DSC thermograph having an onset temperature of between 140 and 150° C., a peak of between 142 and 148° C. and an enthalpy of between −113 J/g and −123 J/g; and
an onset of decomposition in a TGA thermograph of between 120 and 165° C.

In one embodiment, there is provided a crystalline 5MeODMT Hydrochloride, characterised by one or more of:
an endothermic event in a DSC thermograph having an onset temperature of between 140 and 150° C., a peak of between 142 and 148° C. and an enthalpy of between −113 J/g and −123 J/gas substantially illustrated in FIG. 7 or FIG. 8; and
an onset of decomposition in a TGA thermograph of between 120 and 165° C. as substantially illustrated in FIG. 7.

In one embodiment, there is provided a crystalline 5MeODMT Hydrochloride, characterised by one or more of:
an endothermic event in a DSC thermograph having an onset temperature of 145.95° C., a peak of 146.74° C. and an enthalpy of −118.29 J/g; and
an onset of decomposition in a TGA thermograph of between 120 and 165° C.

In one embodiment, there is provided a crystalline 5MeODMT Hydrochloride, characterised by one or more of:
an endothermic event in a DSC thermograph having an onset temperature of 145.95° C., a peak of 146.74° C. and an enthalpy of −118.29 J/g as substantially illustrated in FIG. 7 or FIG. 8; and
an onset of decomposition in a TGA thermograph of between 120 and 165° C. as substantially illustrated in FIG. 7.

In one embodiment, there is provided a crystalline 5MeODMT Hydrochloride, characterised by an endothermic event in a DSC thermograph having an onset temperature of between 140 and 150° C.

In one embodiment, there is provided a crystalline 5MeODMT Hydrochloride, characterised by an endothermic event in a DSC thermograph having an onset temperature of between 140 and 150° C., as substantially illustrated in FIG. 9.

In one embodiment, there is provided a crystalline 5MeODMT Hydrochloride, characterised by an endothermic event in a DSC thermograph having an onset temperature of 146° C.

In one embodiment, there is provided a crystalline 5MeODMT Hydrochloride, characterised by an endothermic event in a DSC thermograph having an onset temperature of 146° C. as substantially illustrated in FIG. 9.

In one embodiment, there is provided a crystalline 5MeODMT Hydrochloride, characterised by an endothermic event in a DSC thermograph having an onset temperature of 145° C.

In one embodiment, there is provided a crystalline 5MeODMT Hydrochloride, characterised by an endothermic event in a DSC thermograph having an onset temperature of 145° C. as substantially illustrated in FIG. 9.

In one embodiment, there is provided a crystalline 5MeODMT Hydrochloride, characterised by an endothermic event in a DSC thermograph having an onset temperature of between 140 and 150° C. and a peak of between 142 and 148° C.

In one embodiment, there is provided a crystalline 5MeODMT Hydrochloride, characterised by an endothermic event in a DSC thermograph having an onset temperature of between 140 and 150° C. and a peak of between 142 and 148° C. as substantially illustrated in FIG. 9.

In one embodiment, there is provided a crystalline 5MeODMT Hydrochloride, characterised by an endothermic event in a DSC thermograph having an onset temperature of 145.57° C. and a peak of 146.22° C.

In one embodiment, there is provided a crystalline 5MeODMT Hydrochloride, characterised by an endothermic event in a DSC thermograph having an onset temperature of 145.57° C. and a peak of 146.22° C. as substantially illustrated in FIG. 9.

In one embodiment, there is provided a crystalline 5MeODMT Hydrochloride, characterised by an endothermic event in a DSC thermograph having an onset temperature of between 140 and 150° C. and an enthalpy of between −115 J/g and −125 J/g.

In one embodiment, there is provided a crystalline 5MeODMT Hydrochloride, characterised by an endothermic event in a DSC thermograph having an onset temperature of between 140 and 150° C. and an enthalpy of between −115 J/g and −125 J/g as substantially illustrated in FIG. 9.

In one embodiment, there is provided a crystalline 5MeODMT Hydrochloride, characterised by an endothermic event in a DSC thermograph having an onset temperature of between 140 and 150° C., a peak of between 142 and 148° C. and an enthalpy of between −115 J/g and −125 J/g.

In one embodiment, there is provided a crystalline 5MeODMT Hydrochloride, characterised by an endothermic event in a DSC thermograph having an onset temperature of between 140 and 150° C., a peak of between 142 and 148° C. and an enthalpy of between −115 J/g and −125 J/g as substantially illustrated in FIG. 9.

In one embodiment, there is provided a crystalline 5MeODMT Hydrochloride, characterised by an endothermic event in a DSC thermograph having an onset temperature of 145.57° C., a peak of 146.22° C. and an enthalpy of −121.95 J/g.

In one embodiment, there is provided a crystalline 5MeODMT Hydrochloride, characterised by an endothermic event in a DSC thermograph having an onset temperature of 145.57° C., a peak of 146.22° C. and an enthalpy of −121.95 J/g as substantially illustrated in FIG. 9.

In one embodiment, there is provided a crystalline 5MeODMT Hydrochloride, characterised by an onset of decomposition in a TGA thermograph of between 120 and 165° C.

In one embodiment, there is provided a crystalline 5MeODMT Hydrochloride, characterised by an onset of decomposition in a TGA thermograph of between 120 and 165° C. as substantially illustrated in FIG. 9.

In one embodiment, there is provided a crystalline 5MeODMT Hydrochloride, characterised by one or more of:
an endothermic event in a DSC thermograph having an onset temperature of between 140 and 150° C.; and
an onset of decomposition in a TGA thermograph of between 120 and 165° C.

In one embodiment, there is provided a crystalline 5MeODMT Hydrochloride, characterised by one or more of:
an endothermic event in a DSC thermograph having an onset temperature of between 140 and 150° C. as substantially illustrated in FIG. 9 or FIG. 10; and
an onset of decomposition in a TGA thermograph of between 120 and 165° C., as substantially illustrated in FIG. 9.

In one embodiment, there is provided a crystalline 5MeODMT Hydrochloride, characterised by one or more of:
an endothermic event in a DSC thermograph having an onset temperature of between 140 and 150° C., a peak of between 142 and 148° C.; and
an onset of decomposition in a TGA thermograph of between 120 and 165° C.

In one embodiment, there is provided a crystalline 5MeODMT Hydrochloride, characterised by one or more of:
an endothermic event in a DSC thermograph having an onset temperature of between 140 and 150° C., a peak of between 142 and 148° C. as substantially illustrated in FIG. 9 or FIG. 10; and
an onset of decomposition in a TGA thermograph of between 120 and 165° C. as substantially illustrated in FIG. 9.

In one embodiment, there is provided a crystalline 5MeODMT Hydrochloride, characterised by one or more of:
an endothermic event in a DSC thermograph having an onset temperature of between 140 and 150° C., a peak of between 142 and 148° C. and an enthalpy of between −115 J/g and −125 J/g; and
an onset of decomposition in a TGA thermograph of between 120 and 165° C.

In one embodiment, there is provided a crystalline 5MeODMT Hydrochloride, characterised by one or more of:
an endothermic event in a DSC thermograph having an onset temperature of between 140 and 150° C., a peak of between 142 and 148° C. and an enthalpy of between −115 J/g and −125 J/gas substantially illustrated in FIG. 9 or FIG. 10; and
an onset of decomposition in a TGA thermograph of between 120 and 165° C. as substantially illustrated in FIG. 9.

In one embodiment, there is provided a crystalline 5MeODMT Hydrochloride, characterised by one or more of:
an endothermic event in a DSC thermograph having an onset temperature of 145.57° C., a peak of 146.22° C. and an enthalpy of −121.95 J/g; and
an onset of decomposition in a TGA thermograph of between 120 and 165° C.

In one embodiment, there is provided a crystalline 5MeODMT Hydrochloride, characterised by one or more of:
an endothermic event in a DSC thermograph having an onset temperature of 145.57° C., a peak of 146.22° C. and an enthalpy of −121.95 J/g as substantially illustrated in FIG. 9 or FIG. 10; and
an onset of decomposition in a TGA thermograph of between 120 and 165° C. as substantially illustrated in FIG. 9.

Example 16: JH-NMR

1H-NMR spectra of the solids were collected (ca. 10 mg of sample in 0.7 ml of DMSO-$_{d6}$) using a JEOL Eclipse 400 MHz spectrometer equipped with an auto-sampler and acquired using Delta NMR Processing and Control Software version 4.3.6.

Example 17: Dynamic Vapour Sorption (DVS)

Sorption isotherms were obtained using a Hiden Isochema moisture sorption analyser (IGAsorp Systems Firmware V20.19.005 COM3) and operated by Isochema HIsorp 2019 V4.02.0102. The sample was maintained at a constant temperature (25° C.) by the instrument controls. The humidity was controlled by mixing streams of dry and wet nitrogen, with a total flow of 250 ml·min-1. The weight change of the sample was monitored as a function of humidity by a microbalance (accuracy+/−0.005 mg). The instrument was verified for relative humidity content by measuring three calibrated Rotronic salt solutions (10-50—88%).

A defined amount of sample was placed in a tared mesh stainless steel basket under ambient conditions. A typical experimental run consisted of three cycles (desorption, sorption, desorption, sorption, desorption and sorption) at a constant temperature (25° C.) and 10% RH intervals over a 0-90% RH range (60 minutes for each humidity level). This type of experiment should demonstrate the ability of samples studied to absorb moisture (or not) over a set of well-determined humidity ranges.

The DVS isotherm of 5MeODMT Hydrochloride, lot 20/20/126-FP (FIG. 11) was found to undergo significant moisture uptake upon the first sorption cycle from 70% RH. Approximately 23% w/w uptake is observed between 70-80% RH, whereas less than 0.3% w/w, moisture uptake from 0-70% RH was observed. A further 20% w/w, moisture uptake is observed up to and when held at 90% RH before commencement of the second desorption cycle. Subsequent sorption and desorption cycles follow a similar profile with some observed hysteresis between operations that do not match the original desorption step. These return to ca. 6-9% w/w, above the minimum mass recorded at 0% RH, which indicates significant retention of moisture. Upon completion of the DVS cycle, the input material was noted to have completed deliquesced.

Following the DVS observations of 5MeODMT Hydrochloride, lot 20/20/126-FP, a modified DVS isotherm of lot 20/45/006-FP (the same crystalline version) was undertaken to examine material behaviour from 60% RH and above. A 2 cycle DVS with desorption beginning from 40-0% RH with sorption from 0-60% RH in 10% RH intervals, followed by incremental 5% RH increases to 65, 70, 75, 80 and finally 85% RH. This is to obtain in-depth profiling of the material towards humidity at these elevated levels.

No significant moisture uptake/loss in first desorption-sorption profile between 0-70% RH was noted (FIG. 12), followed by a ca. 0.46% w/w increase from 70-75% RH. A further ca. 7% uptake is observed from 75-80% RH, then ca. 40% from 80-85% w/w. Complete deliquescence of the solids was observed upon isolation of the material post DVS analysis, which has likely occurred above 80% RH. Despite the observed deliquescence above 80% RH, the solids demonstrate robustness between 0-75% RH and with adequate protection from moisture and conditional storage, this issue would likely be easily mitigated.

Figure 11:
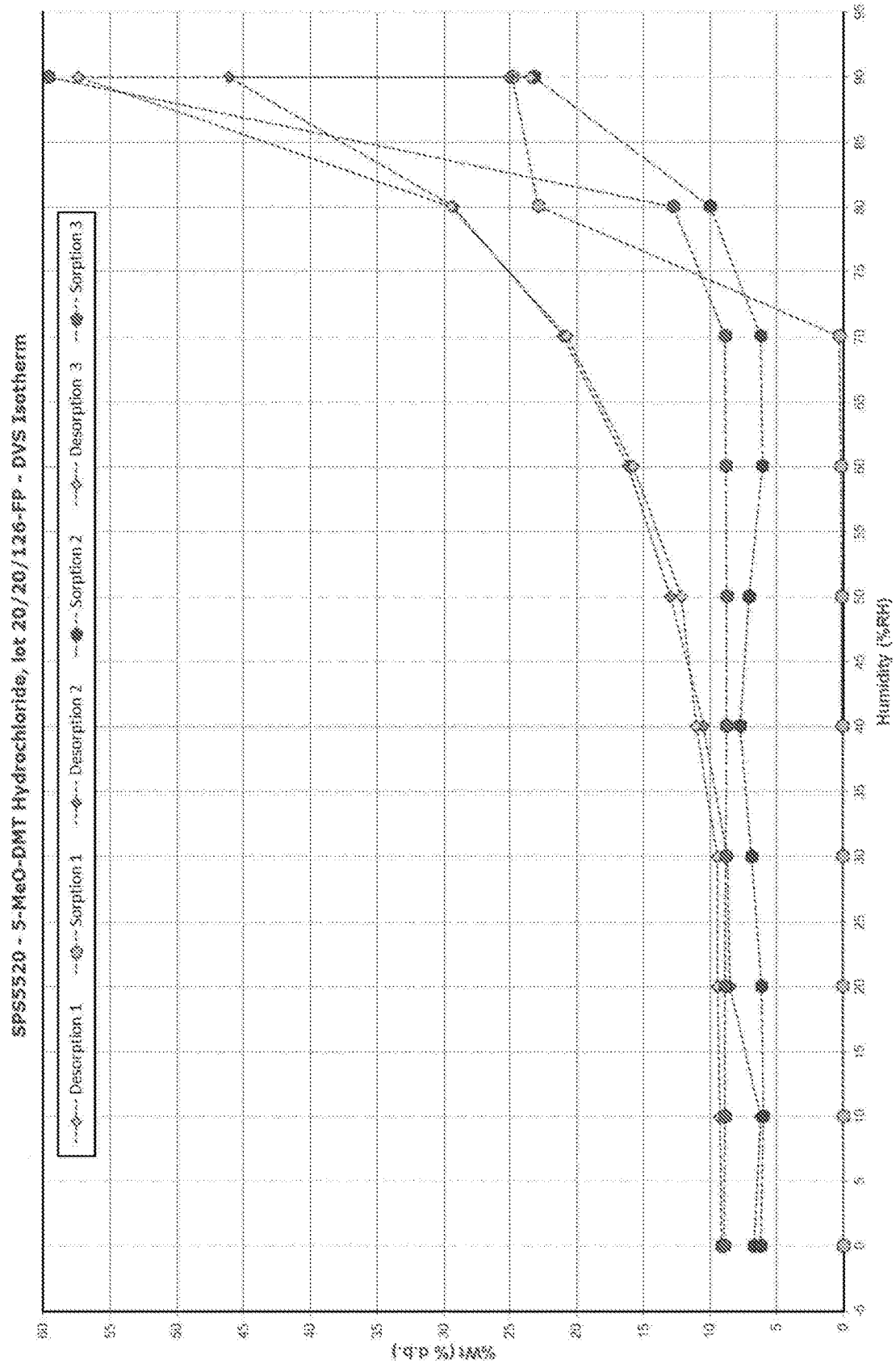
FIG. 11 shows the DVS isotherm of 5MeODMT Hydrochloride, lot 20/20/126-FP.
Figure 12:
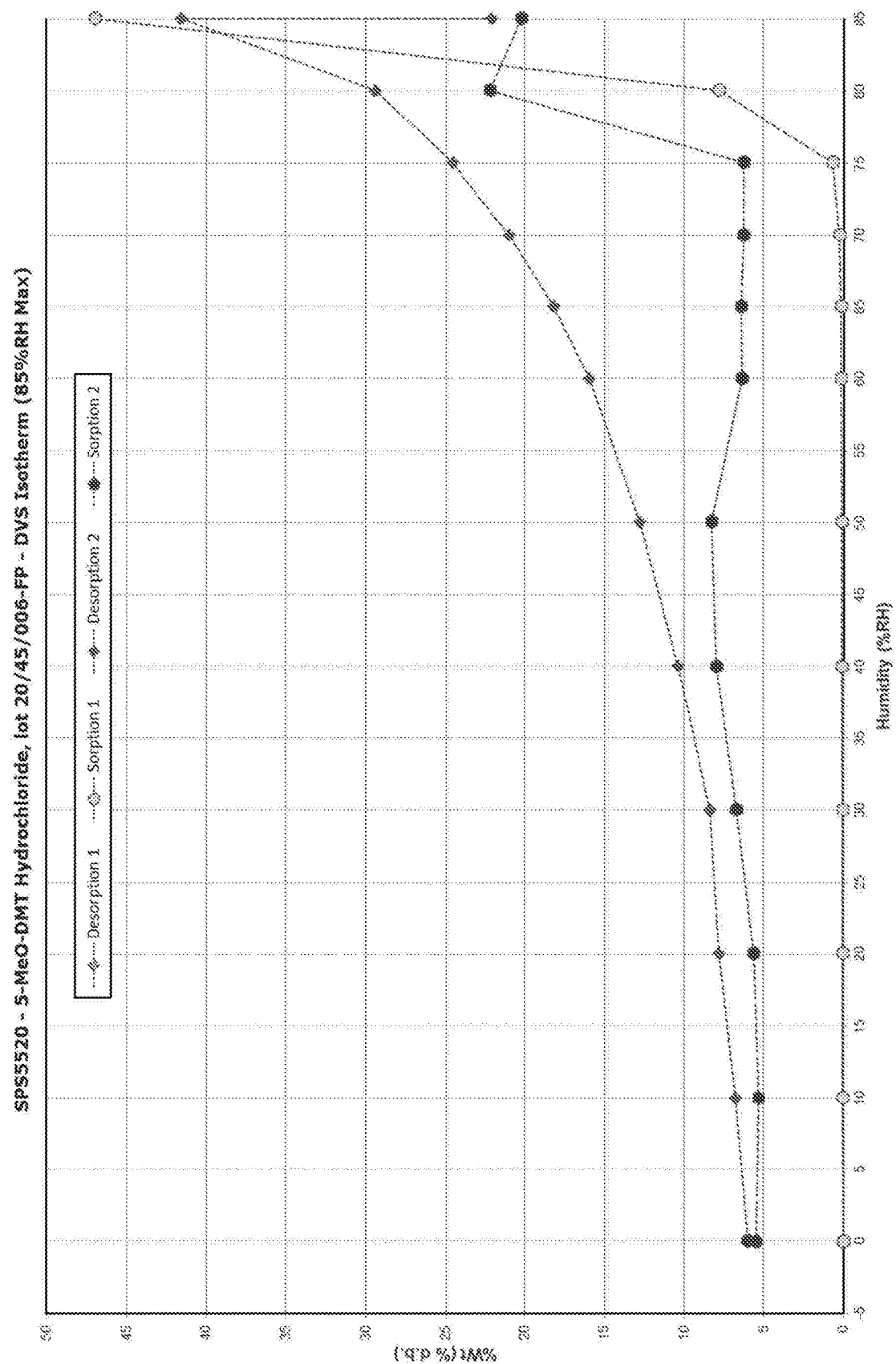
FIG. 12 shows the DVS isotherm of 5MeODMT Hydrochloride, lot 20/45/006-FP.

In one embodiment, there is provided crystalline 5MeODMT Hydrochloride, characterised by a DVS isotherm profile as substantially illustrated in FIG. 11 or FIG. 12.

In one embodiment, there is provided a crystalline 5MeODMT Hydrochloride, characterised by one or more of:

an endothermic event in a DSC thermograph having an onset temperature of between 140 and 150° C., optionally a peak of between 142 and 148° C. and optionally an enthalpy of between −115 J/g and −125 J/g;

an onset of decomposition in a TGA thermograph of between 120 and 165° C.; and a DVS isotherm profile as substantially illustrated in FIG. 11 or FIG. 12.

In one embodiment, there is provided a crystalline 5MeODMT Hydrochloride, characterised by one or more of:

an endothermic event in a DSC thermograph having an onset temperature of between 140 and 150° C., optionally a peak of between 142 and 148° C. and optionally an enthalpy of between −115 J/g and −125 J/g as substantially illustrated in FIG. 9 or FIG. 10;

an onset of decomposition in a TGA thermograph of between 120 and 165° C. as substantially illustrated in FIG. 9; and a DVS isotherm profile as substantially illustrated in FIG. 11 or FIG. 12.

Example 18: Optical Microscopy

Optical microscopy examination was undertaken using an Olympus BX53M polarised light microscope and an Olympus SC50 digital video camera for image capture using imaging software Olympus Stream Basic, V2.4. The image scale bar was verified against an external graticule, 1.5/0.6/0.01 mm DIV, on a monthly basis.

A small amount of each sample was placed onto a glass slide and dispersed as best as possible, using mineral dispersion oil if required. The samples were viewed with appropriate magnification and various images recorded.

Figure 13:
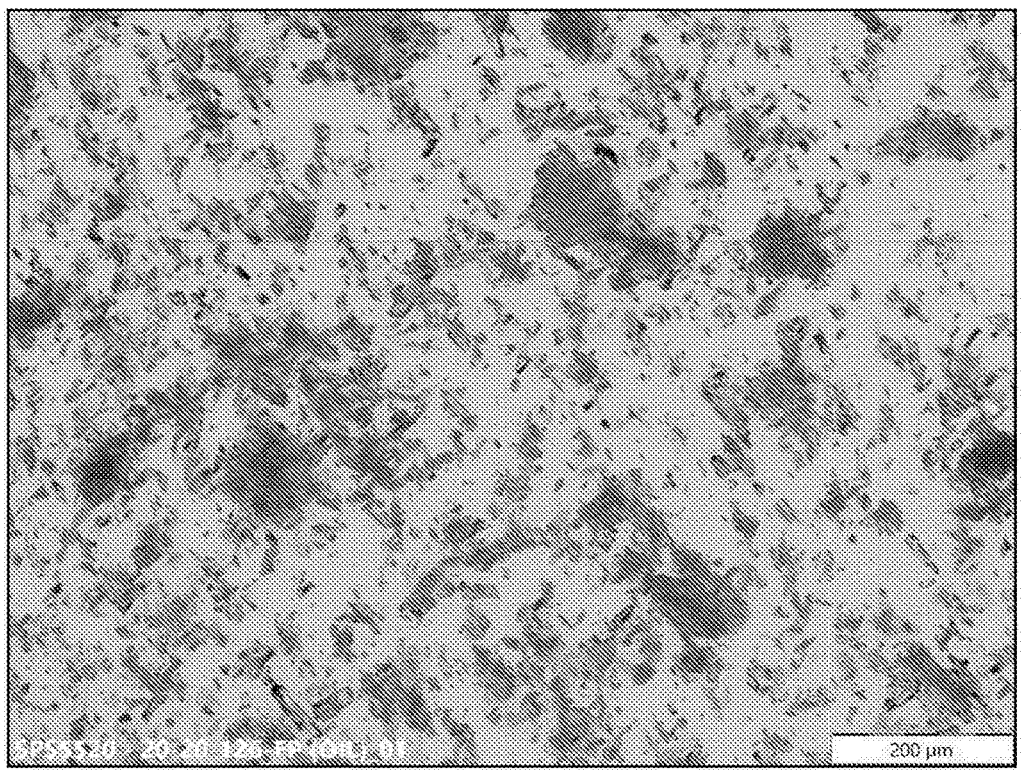
FIG. 13 shows an optical micrograph of lot 20/20/126-FP of 5MeODMT Hydrochloride at ×10 magnification (A) and polarised (B).
Figure 13:
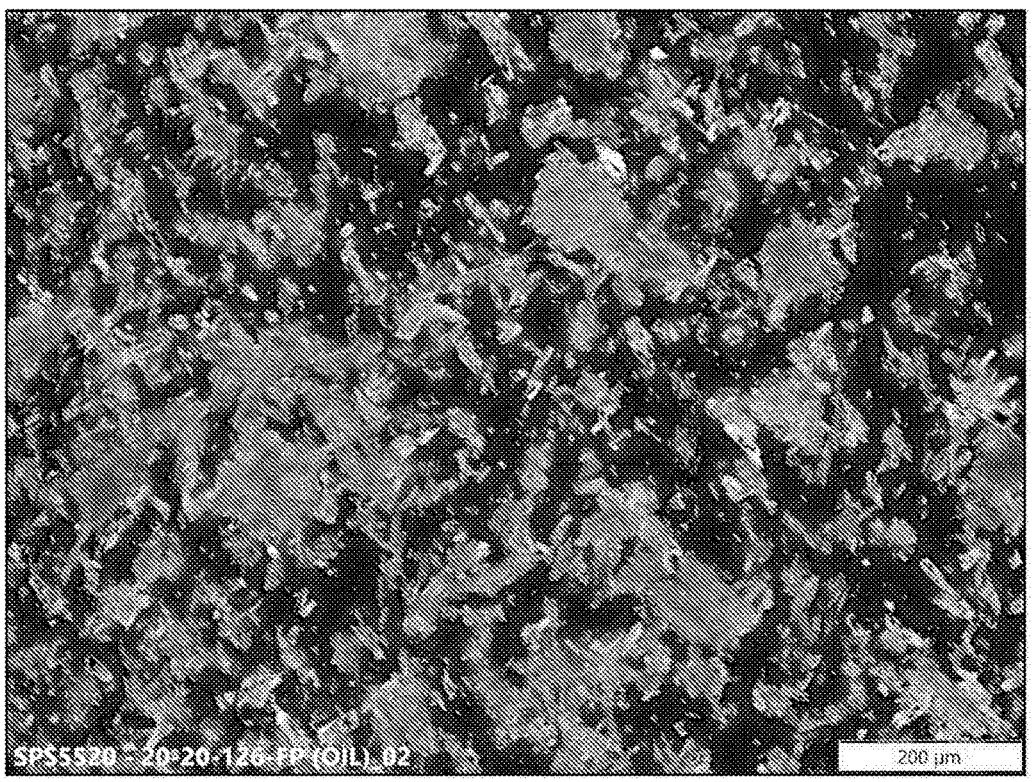
Figure 14:
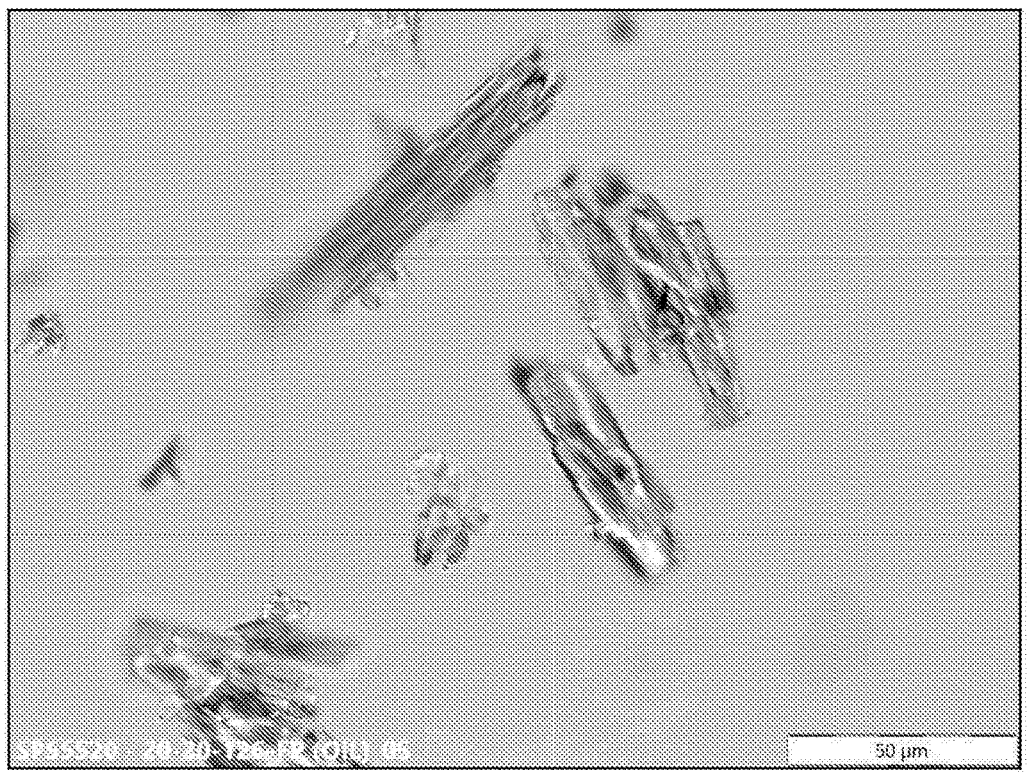
FIG. 14 shows optical micrographs of lot 20/20/126-FP of 5MeODMT Hydrochloride at ×50 magnification (A) and (B).
Figure 14:
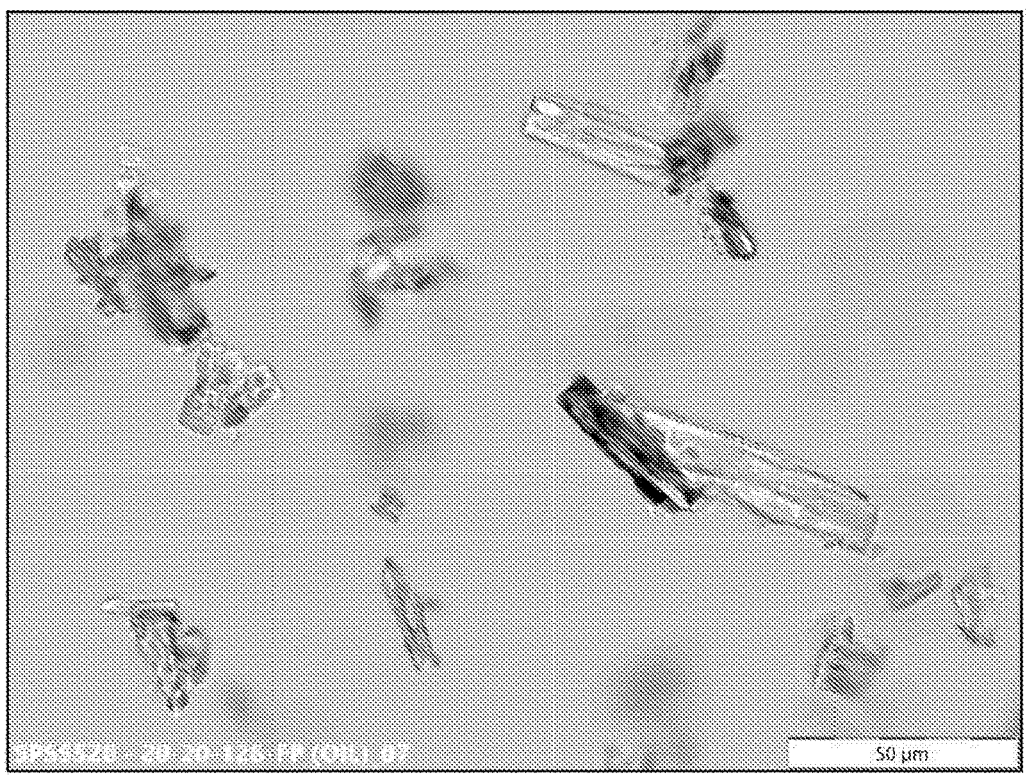
Figure 15:
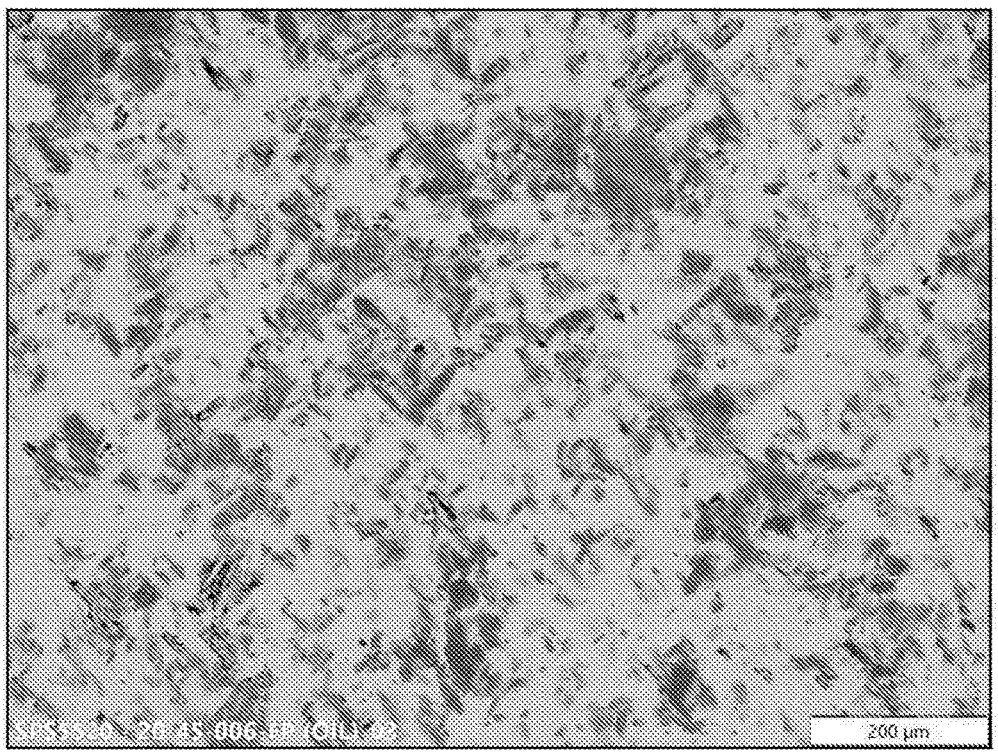
FIG. 15 shows an optical micrograph of lot 20/45/006-FP of 5MeODMT Hydrochloride at ×10 magnification (A) and polarised (B).
Figure 15:
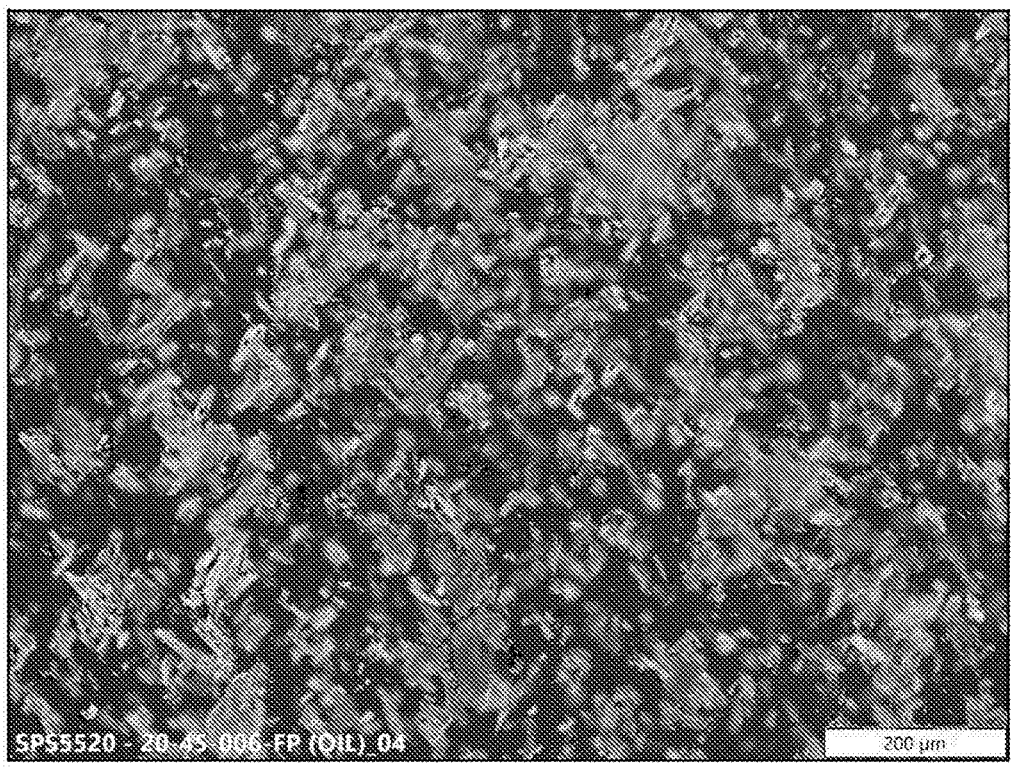
Figure 16:
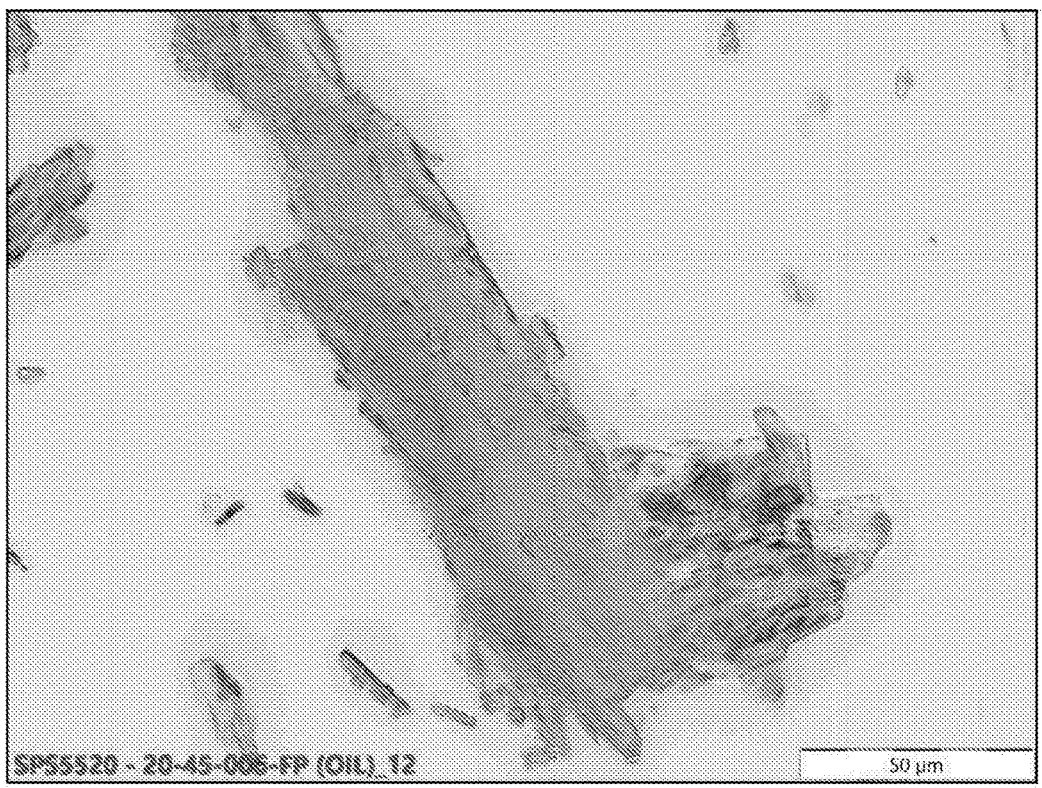
FIG. 16 shows an optical micrograph of lot 20/45/006-FP of 5MeODMT Hydrochloride at ×50 magnification (A) and (B).
Figure 16:
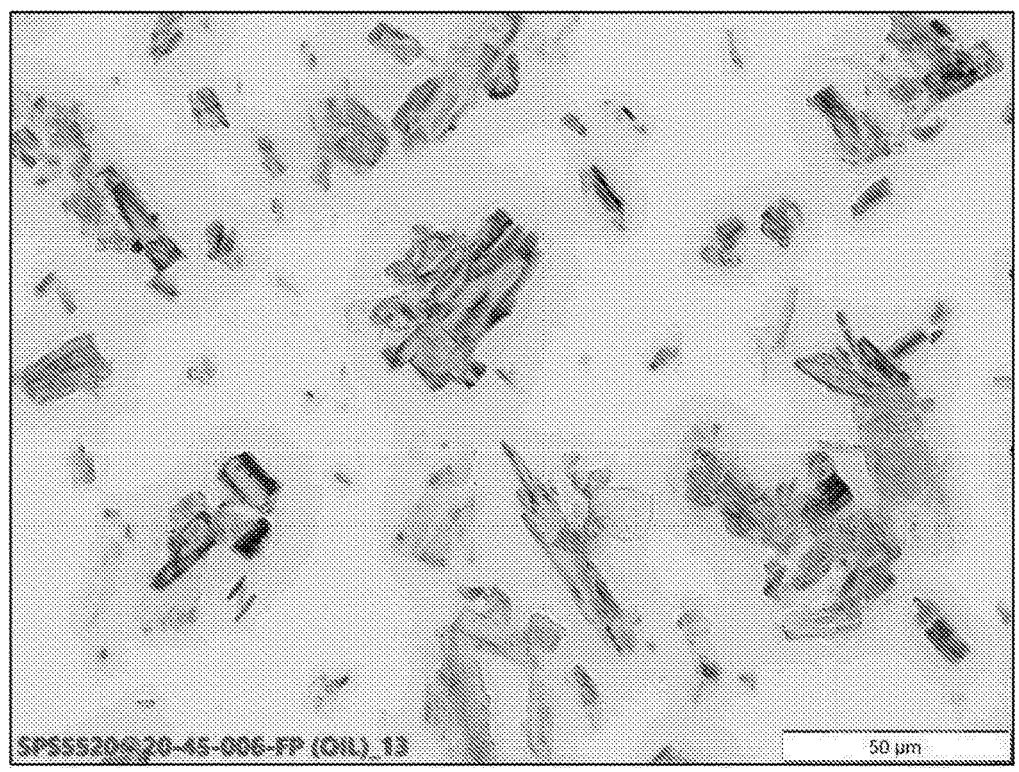
Figure 17:
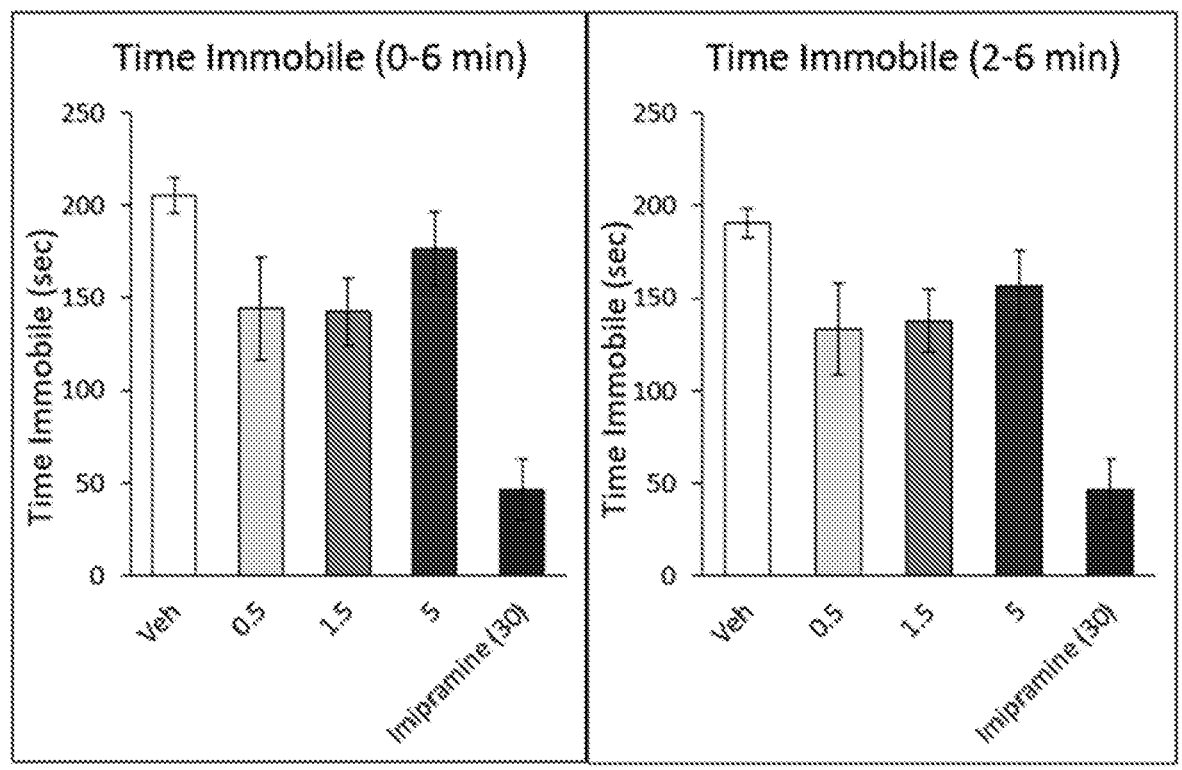
FIG. 17 shows Forced Swim Test results, Time Immobile, for 5MeODMT benzoate, vehicle and imipramine.

The microscopy of 5MeODMT Hydrochloride, lots 20/20/126-FP (FIGS. 13-14) and 20/45/006-FP (FIGS. 15-16) do not differ significantly. Both consist of highly birefringent particulates with evidence of significant solid attrition of the particulates. A thin, columnar habit is, however, observed from individual crystallites that remain intact. There is also evidence of larger particulates that are made up of several individual crystallites that have accreted together during manufacture. Particle size of the main individual crystallites is estimated between ca. 10-50 μm, with some longer particulates up to 100 μm and a width of ca. 5-10 μm. A large quantity of smaller fragments of variable size and shape below 10 μm are noted, with several large solid accretions above 100 μm in diameter also present.

Example 19: Mouse Forced Swim Test

This study aimed to assess the effect of the active agent 5MeODMT, formulated as the benzoate salt, at three doses in the mouse Forced Swim Test (FST). The forced swim test is a model of behavioural despair and is sensitive to detection of various classes of antidepressant drugs.

Husbandry

Housing and Acclimation

Animals received a 72-hour period of acclimation to the test facility prior to the commencement of testing. Animals were housed four per cage in polycarbonate cages bedded with ¼" bed-o'cob. Cages were changed, and enrichment provided according to standard operating procedures. Animals were maintained on a 12-hour light/12-hour dark cycle with all experimental activity occurring during the animals' light cycle. All animal use procedures were performed in accordance with the principles of the Canadian Council on Animal Care (CCAC).

Food and Water

Certified Rodent Diet (LabDiet® 5001) was offered ad libitum. Animals were not fasted prior to, or after the experiment was initiated. Water was provided ad libitum in glass bottles with stainless steel sippers.

Study Design

Test Subjects

Male CD-1 mice from Charles River Laboratories (St. Constant, Quebec, Canada) served as test subjects in this study. Animals generally weighed 25-30 g at the time of testing.

Schedule of Events

| Study Day | Key Event | Procedure |
|---|---|---|
| −8 | Animal arrival | Acclimation to the animal facility |
| −7, to −1 | Daily obs. | Daily health observations |
| 0 | Forced Swim Test | Body weights and observations<br>Dosing with 5-MeO DMT Benzoate, Imipramine, and vehicle<br>Pre-FST behavioural test<br>Forced swim test |

Treatment Groups

Animals were randomly allocated into the following treatment groups:

| Group | Treatment | Route | Pre-treatment time | Group Size |
|---|---|---|---|---|
| A | Vehicle | SC | 3 hr | N = 8 |
| B | 5-MeO DMT Benzoate (0.5 mg/kg) | SC | 3 hr | N = 8 |
| C | 5-MeO DMT Benzoate (1.5 mg/kg) | SC | 3 hr | N = 8 |
| D | 5-MeO DMT Benzoate (5 mg/kg) | SC | 3 hr | N = 8 |
| E | Imipramine (30 mg/kg) | IP | 3 hr | N = 8 |

Pre-FST Behavioural Test

On day 0, in addition to the forced swim test animals were evaluated for signs of 5-HT (serotonin) syndrome. Animals were exposed to activity chambers for 10 minutes at two timepoints post dose: (1) 5-15 minutes post dose, and (2) 2.5 hours post dose.

Forced Swim Test

Male CD-1 mice received the appropriate dose of vehicle, test article, or positive control (treatments summarized above). Following the appropriate pre-treatment time, animals were gently placed into tall glass cylinders filled with water (20-25° C.). After a period of vigorous activity, each mouse adopted a characteristic immobile posture which is readily identifiable. The swim test involves scoring the duration of immobility. Over a 6-minute test session, the latency to first immobility is recorded (in seconds). The duration of immobility (in seconds) during the last 4 minutes of the test is also measured. Activity or inactivity from 0-2 minutes is not recorded.

Test Articles

5-MeODMT Benzoate

BEW: 1.59 (Benzoate salt form)

MW: 340.40 g/mol

Doses: 0.5, 1.5, 5 mg/kg (doses corrected to base)

Route of administration, dose volume: SC., 10 mL/kg

Pre-treatment time: 3 hr

Vehicle: 0.9% Saline

Imipramine

BEW: 1.13

MW: 280.415 g/mol

Figure 18:
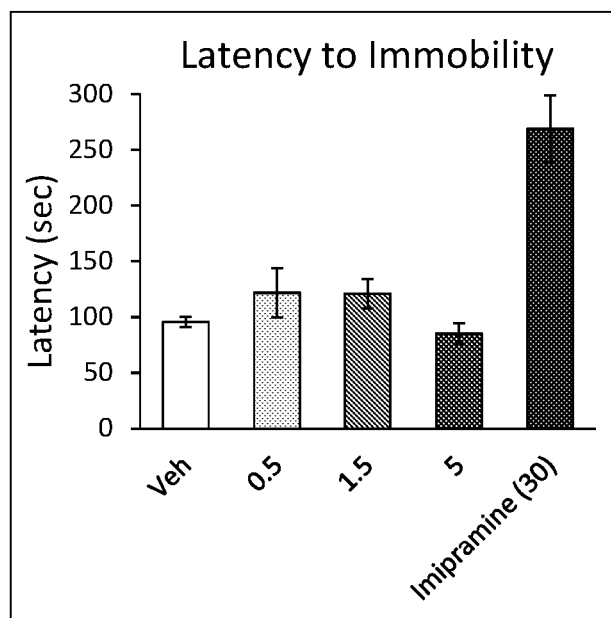
FIG. 18 shows Forced Swim Test results, Latency to Immobility, for 5MeODMT benzoate, vehicle and imipramine.

Doses: 30 mg/kg (doses corrected to base)
Route of administration, dose volume: IP., 10 mL/kg
Pre-treatment time: 3 hr
Vehicle: 0.9% Saline
Results At 3-hour post-dose, over the 6-minute test session, there is a positive trend in reducing the duration of immobility and increasing latency to immobility by the low doses of 5MeODMT salt (0.5 and 1.5 mg/kg), compared to vehicle-treated mice (time immobile 2-6 minutes, vehicle: 190.4±7.7 seconds—5MeODMT salt: 133.2±24.9 seconds (0.5 mg/kg), 137.6±17.0 seconds (1.5 mg/kg), 156.8±18.7 seconds (5 mg/kg)—Imipramine 46.8±16.6 seconds, FIG. 94. Latency to immobility, vehicle: 95.5±4.6 seconds—5MeODMT salt 121.8±22.0 seconds (0.5 mg/kg), 120.9±13.3 seconds (1.5 mg/kg), 85.0±9.5 seconds (5 mg/kg), imipramine 268.6±30.3 second, FIG. 18).

Example 20: Administration of a 5MeODMT Salt

The physical surroundings of the participant/patient/subject are of high importance in the character of many psychedelic experiences. The space should be private, meaning that there should be no chance of intrusion by others. Ideally, sound from outside (e.g. the hallway, the street, etc.) will be minimal. The dosing sessions should take place in rooms that feel like a living room or den rather than a clinical setting. Artwork, plants, flowers, soft furniture, soft lighting, and related décor should be employed in creating a cozy and relaxing aesthetic. Artwork with any specific religious iconography, ideological connotation, or tendency to evoke negative emotions should be avoided. The dosing room may also provide comfortable furniture for the participant and the therapists, who may sit on either side of the participant. Participants under the effect of 5MEODMT may exhibit spontaneous movement or slide off of the bed or couch in their prone position. It is therefore important to make sure no sharp or hard objects are nearby that the participant may fall on. Additionally, pillows may be useful to physically support participants who are mobile during the experience. A therapist can provide physical support to the participant by placing a pillow between their hands and the participant's body.

Music may accompany the experience, so the dosing room should be equipped with a stereo. The room should shield the participant from sights and sounds of the world beyond the room, and the participant should not have any cause for concern of observation or interruption by anyone other than the therapists. The space may also contain:

The tools for safety procedures and medical devices necessary to respond in the unlikely event of a medical complication. The participant should be made aware of these procedures and the equipment, but as much as possible they should be hidden from view.

A secured and locked space for study materials and documentation in the session room or nearby.

An approved safe for storing the 5MEODMT in the session room or nearby.

Audio and video-recording equipment: If allowed in the study protocol the participant will have already consented to being recorded, and should be made aware of the equipment, but it should be placed to be as unobtrusive as possible. Participants may request the cessation of recording at any time.

Physical Space

The space may be large enough to accommodate chairs for two therapists, the stereo equipment and cabinet for storage of the participant's belongings and any extra supplies the therapists may need during the day. The space may accommodate a bed or couch on which the participant can either sit up or lie down with a comfortable surroundings of pillows. The space may be at least $100^2$ feet or $10^2$ meters so that participants do not feel cramped or too physically close to therapists. Participants should have room to explore a variety of positions including sitting on the floor or stretch their bodies without restriction. A bathroom should be either accessible directly from the session room or nearby.

Music

5MEODMT sessions may use a pre-set playlist of nature sounds for creating a calm atmosphere. These nature sounds are considered to be a background element, helping drown out any noise from outside the room, and keep the participant focused on their experience. Participants are not instructed to listen to the sounds in any particular way, but may be asked to focus on it as a way of grounding their senses and relaxing before or after session.

Medication Discontinuation

Medication discontinuation can be challenging for participants. Participants are to have discontinued all contraindicated medications and completed washout periods prior to Prep-1 with the therapist. The study team members, including the therapist, may provide supportive check-in calls with the participant prior to this, as-needed during the washout period, but should not start Prep-1 until washout is complete and the participant confirms intention to continue with the therapy.

Preparatory Sessions

This treatment model includes three, 60-90 minute preparatory sessions with the therapist. These take place 7 days, 4 days, and 1 day before the 5MEODMT session. Preparatory sessions are designed to take place via telemedicine, but can be in-person if possible.

Preparatory Session 1

The following topics may be covered in the first preparatory session.

Getting to Know the Participant

The therapist will spend some of the preparation session time getting to know the participant. The therapist may ask open-ended questions about:

How they found out about the treatment and what their expectations are;

Current life situation with regards to living situation, work, school, and important relationships;

Understanding of their own depression;

Key life events that the participant feels might be of relevance

The therapist should be listening for how the participant talks about themselves and their relationship to their depression, how they relate to the therapist and study environment, and stay attuned to establishing a sense of trust and rapport with the participant. Clinical impressions of difficulty forming a trusting relationship with the therapist or any other clinical factors that could interfere with the participants' ability to engage in the treatment should be noted and discussed with the study team. Although in the preparatory session stage, the therapist may learn more of the participant that could be reasons for study exclusion.

Establishing the Role of the Therapist

Therapists in the 5MEODMT-assisted therapy treatment model form a relationship with study participants which becomes part of the container in which the 5MDE (subjective experience of 5MeODMT) takes place. This formation of this relationship is deliberate on the therapist's part and characterized by the therapist establishing transparency and trust, taking clinical responsibility for the patient's wellbeing, and relational and emotional safety for the patient. The therapeutic relationship is understood as a critical component of the set and setting for the therapeutic use of the 5MDE. The communication and establishment of this relationship is both explicit (overt) and implicit (covert) in the therapists behaviours and mannerisms throughout the treatment.

Explaining the therapeutic model with participant as active participant in their process The therapist should explain the therapeutic model used in this research study to the participant in the first preparation session. The explanation should include:
Practical aspects:
How many meetings with the therapist will occur, and for how long.
That the therapy is thought to work by:
Creating a safe container for the experience so that the participant knows what to expect and can fully let go into their experience,
Helping the participant focus on and explore their own responses to the experience,
Facilitating a process of the participant determining for themselves how they will put their insights into practice in their life.
That the therapist's role is:
Supporting the participant through the session, engaging in a series of activities to elicit the participant's unique experience and insights, fostering the participant's process of implementing the resulting changes in their life.
That the therapy is:
Not a full deep dive into participant's personal history, not a place to do specific problem solving or engage in CBT, Psychodynamic interpretations, get general advice, or receive other interventions the participant may be familiar with.

Establishing Physical, Emotional, and Psychological/Relational Safety

Beginning in the first preparatory session the therapist establishes the environment of physical, emotional, and psychological safety. The therapist explains the safety of 5MEODMT and the safety procedures relevant to the participant's physical health for the session. With regards to emotional safety the therapist states that all emotional experiences are welcomed, that there is no area of experience that the participant is not welcome to share. Safety can also be established through the calm reassuring presence of the therapist, which does not always require the use of language.

The use of self-disclosure is not prohibited, but should be used very sparingly. A participant may be seeking safety by asking personal questions of the therapist. If the therapist chooses to disclose, it should be brief and under the condition the participant share why this personal information is important to them.

Psychological/relational safety is established by assuring the participant that their wishes will be respected with regards to the use of touch. Also, the participant is to be reassured that if they choose not to participate in the 5MDE experience they may do so at any point up until drug administration and that this will be respected, and that the therapy sessions will still be available to them if they make that choice.

The therapist can use the following techniques to establish safety with the participant:
Ask open-ended questions that invite the expression of doubts, hesitancies, or concerns:
What questions do you have for me?
What more would you like to know about 5MeODMT?
What would you find helpful in the event . . . ?
How could I be of assistance to you if you feel . . . ?
Encourage and engage with the full range of participant's emotions and experiences without trying to fix or resolve them:
Participant expresses skepticism about the 5MEODMT Experience: I appreciate you sharing that doubt with me. What do you make of that in light of your presence here at this time?
Participant expresses fear about the 5MDE Experience: What more can you tell me about your fear and how it manifests for you? How could I be helpful to you as you experience this?
Use affirmations to establish an environment of valuing the participant's time and effort:
I really appreciate the time you are putting into this treatment and your willingness to participate in research.
Your experience is unique to you and I appreciate the opportunity to see you through this process.

Expected Potential Subjective Drug Effects (Unity, "feeling Like Dying", "the Void".)

It may be helpful to discuss the concept of "non-ordinary state of consciousness" with participants. In the past, "altered state of consciousness" was often associated with experienced engendered by psychedelic compounds. However, alterations of consciousness are experienced on a daily basis, as moods or feelings shift, or when people shift from awake alertness to feeling tired and drowsy. "Non-ordinary state of consciousness" emphasizes the quality of an experience that is not ordinarily had on a daily occurrence, but can still be within human experience.

The therapist may begin this conversation by asking the participant about their existing knowledge of 5MEODMT effects, and listen for specific expectation or ideas about it. The therapist is to encourage an attitude of openness toward the experience, encouraging participants to explore what kinds/ideas they may have and be open to the possibility that it will not be possible to imagine what this will be like. Participants may have specific expectations based on the media, prior experience with 5MEODMT or other psychedelics, or other kinds of non-ordinary states of consciousness. It is important for therapists to provide a balanced description of what the participant may experience.

Different people have different levels of comfort with "not knowing" what something will be like, or what to expect. The therapist may explore the participant's level of comfort with the unknown, their relationship to the idea the future not being fully knowable in any situation, and how they generally relate to this. Among participants with depression there may be deep fear of the unknown, anticipation of what is expected in the future (more negative experiences), resulting in a feedback loop of feeling fearful and depressed. Therapists should elicit and explore this area during preparation.

Common 5MeODMT Experiences: The therapist should also introduce a few key terms and commonly reported experiences known to occur under 5MEODMT. These include a feeling of unity, a feeling of dying, and a feeling of entering or experiencing a "void" (absence of material reality). Some participants may have an existing spiritual, philosophical, or religious belief system through which they will interpret or make meaning of these experiences. Therapists should enquire about this and work with the participant's own explanation and terms, without taking a stance as to whether these are correct or erroneous.

Social Support and Social Media

Participant's social support may be assessed during preparation sessions and be determined by the therapist to be adequate to support the patient through the process of change, especially in the event of either disappointment or dramatic symptom reduction. In the event the participant has a psychotherapist outside of the study the study therapist may, with the participant's permission, have a phone call with the participants therapist to describe the nature of the study and therapeutic approach and answer any questions the therapist may have. The study therapist may also educate any friends or family members who are close to the participant and have questions regarding the nature of the study, the 5MEODMT experience, and what to expect. The therapist should discuss social support with the participant including preparing the participant for the variety of reactions their friends and family may have.

Therapists may advise participants to take caution around posting about their experience on social media so as not to elicit excessive public commentary. Inadequate social support or use of social media in a way that may be disruptive to the therapeutic process may be discussed and resolved prior to 5MEODMT Administration.

Preparatory Session 2

The following topics may be covered in the second preparatory session.

Drug experience preparation: trust, surrender (let go), embrace, transcendence.

There are several key attitudes towards psychedelic experiences that are considered to be conducive to a positive and clinically helpful experience. The more participants can embody a relaxed stance toward their experience the less likely they are to struggle, inadvertently creating a loop of stress and distress that heightens attention to negative aspects and interpretations. The therapist may educate the participant on the purpose of deliberately generating an attitude of trust, surrendering to the experience, and letting go of attempts to control the experience. Therapists may encourage participants to develop an attitude of welcoming and embracing all experiences they may have as part of their 5MEODMT experience. The therapist may suggest to a participant that all aspects of the experience (feelings, sensations, and thoughts) can be welcomed. Previous research with psychedelics has demonstrated that a capacity to be absorbed by the experience can contribute to the potency of a mystical experience.

The Drug Administration

The therapist should explain that on the day of the session that a member of the research team will enter the room briefly to administer the study drug. The therapist should explain the participant positioning, e.g. they will be in a seated position on the bed or couch, that the research team member will insert the nasal spray device in one nostril, and that they will be asked to allow the therapist to assist them in lying down on the bed or couch immediately afterward.

Session Procedures Including Boundaries, Use of Touch, Safety, Etc.

The therapist will explain the process of the session. The session is contained by the timing of the dosing and the physical environment of the dosing room. It begins when the participant enters the room and engages with the therapist in the Session Opening. Session Opening is a formal moment in which the participant and therapist sit together in the room, all preparations having been made, and playlist started. The therapist may lead a breathing exercise of the participant's choice, if the participant is open to engaging in one, and ask the participant to reflect on the values they choose in the preparation session, or any other value or intention that is important to them. Once the participant signals that they are ready, a member of the research team will administer the nasal spray to the participant. Trust and safety are not only communicated verbally, but also this may be nonverbally through how a therapist holds themselves in the presence of the participant. If a therapist is overly anxious, or fearful, this may be felt by the participant. It is important that the therapist is centered throughout the dosing session, particularly at times when a participant is expressing intense affect, unusual somatic expressions, or is asking for support.

Somatic Changes and Shifts in One's Sense of their Body

Some participants may experience an intensified awareness of their body such as feeling their heart rate more strongly or physical sensations in their temple. Other participants may be aware of a tingling in their body, changes or perceived difficulty breathing, or other unusual physiological experiences. It is important for the therapist to communicate that these changes in perception are normal and should not be a focus of preoccupation or fear. If these sensations arise, the participant should be encouraged to communicate these to the therapist, if they so desire. The therapist should reassure the participant that these sensations are expected and are normal to have. The therapist can inform and remind the participant that naturally occurring 5MEODMT has been consumed in other settings for hundreds of years with no indication that it is physically harmful, and that these changes are expected and will resolve shortly.

Discussing Expectations and Intentions

Expectations can be defined as mental representations and beliefs of how something in the future will be. Sometimes expectations can be explicitly identified, and sometimes they are subperceptual, taken for granted. Both kinds of expectations may be important to treatment. The therapist should ask about explicit expectations and encourage the participant to acknowledge and set these aside such that they do not engage in comparing their experience to expectations. The therapist is also listening for subperceptual expectations that may come into awareness through the therapy. Intentions are ways of relating to a behavior or experience. In the 5MEODMT treatment, it can be important for the therapist to elicit and understand the participant's intentions as these can vary greatly and may be taken for granted. Therapists are to engage participants in a process of identifying and setting their intentions such that these are explicit and can be referenced later in integration. The purpose of the intention is for it to be identified and then let go of, with the knowledge that it can be part of the 5MED.

Recurrence of Acute Effects

Some individuals who used 5MEODMT in non-clinical contexts have reported re-experiencing 5MEODMT's subjective effects in the days after. The dose used, purity, and other factors were not monitored in these cases. The likelihood of these reactivations occurring in a controlled clinical study context is not known, but estimated to be less likely. Nonetheless, it is important for participants to be made aware of this phenomenon. The experience of reactivations are often reported as pleasant, brief (lasting a few moments to minutes), and do not occur with enough frequency to interfere with a person's life. These reactivations are thought by some as part of the integration process. If a participant notices certain activities trigger reactivations, such as certain meditative states, stimulants, or other drugs, and the participant finds these reactivations unpleasant, it should be suggested to the participant that they avoid such triggers.

Processing the 5MEODMT experience in therapy, as part of integration, may also be helpful.

Discussing the Use of Touch

Therapists in this modality may engage in two types of touch: therapeutic touch, and touch for safety reasons. During preparation the therapist should explain and define each. Therapeutic touch is touch that is intended to connect with, sooth, or otherwise communicate with the participant for therapeutic aims. It is always fully consensual, non-sexual, and the participant is encouraged to decline or cease therapeutic touch at any time. Touch for safety reasons can include supporting a participant who is having trouble walking by offering an arm to hold, or blocking a patient back from leaving the room while under acute drug effects. This touch is agreed to in advance, is always non-sexual, and limited to specific safety concerns. Therapists should discuss both of these and establish boundaries with participants ahead of session.

Preparing for after the Session (What to Expect, What to do, Setting Aside Time for Integration)

Participants should be encouraged to take some time to rest and integrate their experience after their session day. Study therapists should ask participants to plan for time off after their session, at least the full day of the session and the day after the session. Therapists should explain that after the acute effects of the 5MeODMT have worn off they will stay together in the room for a while. This period of time will be for the participant to readjust to their experience after the acute effects. They will be asked to share what they can recall about their experience and any reactions they have. They will not be asked to share anything they don't want to share, and are welcome to keep their experience private. They may choose to write or draw about their experience, art supplies and writing supplies will be available. They may be encouraged to spend some time continue to stay with their experience, with the therapist's support, for around an hour. They will then meet with the study team for a safety assessment before going home. Once at home they are encouraged to rest and continue to stay with the experience and the insights, ideas, or new understanding they may have from it. Participants should be reminded that they do not need to share their experience with others unless they want to, and are encouraged to continue to focus on it in whatever way they find most helpful. Participants should refrain from returning to work, from driving, drinking alcohol, drug use, or being a sole caregiver for a child or dependent for the rest of the day.

Therapist Teaches Breathing Exercise for Dosing Session

When stressed, breaths become shorter and shallower, and when relaxed, the breath becomes longer and slower. Working with the breath is a way of modulating and regulating one's mental state. The therapist may teach and practice two breathing techniques with the participant. These are designed to help the participant relax their body and mind, tolerate stressful or uncomfortable experiences, and develop autonomy through practice on their own. These are not for use during the acute effects of 5MeODMT, but can be used prior to dosing and afterward.

When teaching the practices, the therapist elicits the participant's individual response to each practice to assess suitability of using it. Breathing practices include: Balancing Breath, Diaphragmatic Breath and Counted Breath.

Preparatory Session 3

Values Card Sort with Prompts

The therapeutic protocol may use a customized Personal Values Card Sort to assist with the therapeutic focus on shift in sense of self. This is done by asking about how people relate to their chosen values before the session, and how they relate to them afterward, drawing attention to shifts, changes, and using these as a guide for the kind of changes the participant may desire to make. It is used as a way to elicit conversation about the participant's sense of self, beliefs about self, and changes in those senses/beliefs throughout the therapy. Therapists may engage participants in the card sort exercise in the third preparation session such that it occurs 1-2 days before the dosing session.

The Values Card Sort Instructions are:
1. Place five anchor cards in order from 1-5 in front of the participant from left to right in order of least to most important.
2. Shuffle the 100 value cards; keep the 2 blank cards separate.
3. Instruct the participant to sort the cards using the following script: "I placed Jive title cards in front of you not important to me, somewhat important to me, important to me, very important to me, most important to me. I'm going to give you a stack of 100 personal value cards. I would like you to look at each card and place it under one of the Jive title cards. There are also two blank cards. If there is a value you would like to include, write it on the card and put it in whichever pile you would like. I would like you to sort all 100 cards, but whether you use the two additional cards is optional. Do you have any questions?"
4. When the participant is finished sorting, thank them and invite them to look at the "most important" category, removing the other cards from the table.
5. Read the following: "For the second task, I'd like you to focus on the top values you put in the "most important" category and choose the top five."
6. When the participant has chosen their top five cards, thank them read the following: "For the third task, I'd like you to focus on the top five values you chose and rank them in order from most to least important."
7. When the participant indicates they are finished ordering, check to make sure you understand how the cards were sorted (ascending or descending). Point to the #1 spot and say, "I want to make sure I have this right—is this your number one value?"
8. Record values on a scoring sheet, journal or by taking a picture of the cards. Participants should keep a record of their card selections as well.

Debriefing and Discussion:

Next, invite the participant to engage in a structured discussion of each value using a few of the following open-ended prompts, or similar prompts depending on the context of your work:

You selected _____ as your #_____ value?;

Please tell me more about what _____ means to you?

What are some ways _____ has been represented in your life?

What are some ways you'd like to see more of _____ in your life?

How does your decision to _____ or not relate to this value?

How much _____ would you like to have in your life?

How would you know if _____ was increasing or decreasing in your life?

How does _____ relate to the change you are trying to make (or considering making)?

Invite the participant to journal about their answers to the same questions with the remaining cards afterwards. In later sessions it can be helpful to check in on the values and revisit these questions, see how answers have changed, and how participants are currently relating to their values.

Assistant Therapist

The session may be conducted by the therapist with an assistant therapist such that a second person is available to assist in case of any adverse event or physical complication in the participants safety. The assistant who will be present for the session should be introduced in Prep Session 3 and included in a conversation such that they get to know the participant.

Session-Specific Therapeutic Tasks

Therapists should aim to complete the therapeutic tasks outlined above according to the chart below, while acknowledging that some variation will occur based on individual participant needs.

| | |
|---|---|
| Prep Session 1 | Getting to know the participant |
| | Establishing the role of the therapist |
| | Explaining the therapeutic approach/model with participant as active participant in their process |
| | Establishing physical, emotional, and psychological/relational safety. |
| | Expected potential subjective drug effects (unity, "feeling like dying", "the void",) |
| | Social Support and Social Media |
| Prep Session 2 | Drug specific preparation: trust, surrender (let go), embrace, transcendence, |
| | Drug Administration |
| | Session procedures including boundaries, use of touch, safety, etc. |
| | Discussing expectations and intentions |
| | Discussing the use of touch |
| | Preparing for after the session (what to expect, what to do, setting aside time for integration) |
| | Teach and practice Breathing Exercises |
| Prep Session 3 | Values card sort with prompts |
| | Instruction to continue values card sort inquiry for homework after session if needed. |
| | Confirm plans for session and review any questions participant has. |
| | Assistant Therapist joins the session for an introduction if needed |

5MeODMT Experience Session

The therapist is present with the participant during the session—including pre-experience and post-experience times. This is the only session that must be conducted in-person. The site and therapist should schedule about 3 hours for the session, including pre-experience and post-experience time. This does not include the time allotted to engage in baseline measures and enrolment confirmation prior to the session. Local regulatory approvals will determine the minimum length of time a participant must be under observation following 5MEODMT administration.

Pre-Experience (Around 30 Minutes)

After the participant has completed all enrolment confirmation and randomization procedures and is cleared to participate, the Therapist, Assistant Therapist, and participant together in the room review all aspects of the room and safety procedures. The therapist should introduce the participant to the team member administering the 5MEODMT, to create a sense of familiarity. Therapist introduces any Assistant Therapist and reviews safety features of the room and the equipment present. Participant has time to ask any questions. The therapist will ask about any responses to the situation and how the participant is feeling about their session. The participant should not be rushed into the dosing by the therapists. The therapist will ask the participant to engage in a period of relaxation prior to dosing. Participant will be asked to lie down, close their eyes, listen to the music, and, if willing, engage in at least one of the breathing exercises with the therapist's guidance. When the participant is settled and comfortable, the therapist will initiate the Session Opening. This practice helps contain and emphasize the specialness of the experience. Therapists will contact the member of the research team to come to the room and administer the 5MEODMT. The team member should be aware not to disrupt the peaceful atmosphere of the room. The participant should be in a seated position when insufflating the 5MEODMT, as the effects may be felt quickly, the participant should be transitioned to a prone position and remain prone for the duration of the effect of the 5MEODMT.

Experience (Around 60 Minutes)

It is expected that the onset of acute effects will occur very rapidly after administration. Therapists should be aware of the time of administration so they can be aware of the participant's response in relation to the expected course of duration. Some participants may want to know how long they experienced the effects of the 5MEODMT and it is appropriate to share this information if asked. A significant portion of the time the participant may be nonverbal, focused inward, and engaging in their experience. It is important for the therapist to be mindfully aware of the participant, but not interfering with the participant's experience, unless it is clear that participant is seeking the therapist's support. Therapists are encouraged to engage in self-regulation techniques while the participant is undergoing their experience. This may be in the form of slow intentional inhaling and exhaling, or any other activity that helps the therapist ground and self-regulate. This is both for the therapist's benefit, as well as the participants', because a participant in a heightened non-ordinary state may be particularly attune to or pick up on their therapist's anxiety. It is optimal for the therapist to follow the participant's lead when choosing to verbally engage as the 5MEODMT experience appears to be subsiding. Therapists may be eager to ask the participant about their experience, but it is preferable to wait until the participant is ready to share on their own. A participant may wish to remain in a period of silence, even after the apparent acute 5MEODMT effect is gone. It is appropriate for therapists to greet participants with a friendly smile and welcoming nonverbal behavior, and allow participants to take the lead on sharing when they feel ready.

Post-Experience (Around 90 Minutes)

Therapist will encourage the participant to stay with their experience for a period of time of at least one hour after the acute effects of the 5MEODMT have worn off and the participant is once again aware of their surroundings and situation in the treatment room. To stay with the experience means to continue directing attention toward it in whatever way feels most appropriate to the participant, without turning to engagement in distractions, entertainment, or the concerns of daily life. During this time the therapist will invite the participant to describe their experience, if they choose to, and respect the choice not to if the participant is unready. If the participant does describe their experience the therapist is to listen and encourage the participant to express whatever they would like to share without interpretation or attempts to make meaning. The therapist practices simply listening, encouraging the participant to describe what they can about the experience. The therapist also offers the participant the option of resting and listening to the music, or to write about or draw any aspects of the experience they desire. At the end of this time period, the therapist will verify with the participant that they feel ready to close the session, will engage in the Session Closing, and contact the study team for exit assessment.

Integration Sessions

The key principle of integration sessions is to help the participant focus on shifts in their perception of themselves and the implications of these as they relate to their depression. Self, for the purpose of this study, is broadly defined as the narrative or historical self, the sense of a coherent "I" that moves through experiences, and the self-identities one may use. It is key to remember that the sense of self, or the "I," is reflected in both the experiencer's self-experience and experience of the object of experience, therefore descriptions may, on the surface, be of changes in the perception of the external world, but reflect shifts in the internal processes. To this end, the following therapeutic tasks will guide the integration sessions.

These sessions are less structured than preparatory sessions to accommodate variations in participant responses. There are three tasks: The first should occur at all sessions, the second and third may be introduced and engaged in if and when the participant is ready and willing. The tasks are:

Listening and Hearing about the Participant's Experience

Therapists ask open-ended questions about the participant's experience and listen with non judgmental curiosity to the participant's descriptions. Therapists ask only that participants focus on the 5MDE and related material, such that their time together is focused on the treatment. Therapists should focus inquiry on the participant's experience, asking them to tune into any aspect of the three types of sense of self they can identify.

Reintroducing the Values and Discussing Relationship to Each

The therapist will reintroduce the values identified in the Values Card Sort from preparation and bring discussion back to them if and when appropriate in the integration sessions. There is by no means a requirement to engage in the structured discussion of the values, but it serves as a framework where needed to direct the focus of sessions toward participants' shift in sense of self The Therapist May Ask for Example, to Reintroduce the Values:

Therapist: Before your 5MDE we discussed a list of Values you hold and how you were relating to each of those. I'd like to draw our attention back to that and ask for a little detail about how those ways of relating might have shifted. For instance you named "Family" as one thing that was important to you, but you were concerned that you weren't feeling well enough to be present for family relationships. You said you were isolating from your family a lot by working on your computer from your makeshift office in the garage every evening. How do you relate to the value of "Family" now?

In the dialogue, the therapist can for example continue to focus on shifts in how the participant is relating to his value of "Family" by enquiring about what he is noticing in this area.

Create ways the participant can act to enhance their relationship to their chosen values; identify value-oriented action in their life as an integration practice. Integration can be understood as a process of embodying or living out the insights one has. In at least one of the integration sessions, the earliest the therapist feels the participant can engage in this stage, the therapist should introduce the idea of identifying value-oriented actions they can take in their lives as integration practices. Explaining the concept as above, the therapist can invite the participant to recall the values they identified (or any other that is important to them), recall the insights or experiences of their 5MEODMT session, and think creatively about things they might try intentionally doing differently in order to implement positive change in their relationship to the values based on those insights and experiences Items:

1. A method of administering 5MeODMT or a pharmaceutically acceptable salt thereof to a patient who is diagnosed with depression, the method comprising:
   the discontinuation of the use by the patient of any mood-altering substance or any other substance, medications or preparation which may affect serotonergic function;
   the relaxation of the patient, such as the patient is instructed to lay down, close their eyes, and listen to music and/or engage in one or more breathing exercises guided by a therapist;
   optionally, the clearing of their nasal passages, by blowing their nose, by the patient e.g. whilst sat down;
   the administration of 5MeODMT, optionally by via insufflation, and optionally wherein the patient is in a prone position for the duration of the effects of 5MeODMT.
2. The method of item 1, wherein the patient has discontinued the use of monoamine oxidase (MAO) inhibitors, CYP2D6 inhibitors, selective serotonin reuptake inhibitors (SSRIs), serotonin-norepinephrine reuptake inhibitors (SNRIs), tricyclic antidepressants (TCAs), lithium, antipsychotics, triptans, tramadol, 5-hydroxytryptophan, herbal preparations which may contain 5-HTP, St John's Wort and any benzodiazepines prior to administration of 5MeODMT.
3. The method of item 1 or item 2, wherein the 5MeODMT is administered via the Aptar Unidose (UDS) liquid delivery system.
4. The method of item 1, item 2 or item 3, wherein the 5MeODMT is the benzoate salt, optionally a polymorph of the benzoate salt.
5. The method of any one of items 1 to 4, wherein the patient participates in at least one psychological support session before administration of the 5MeODMT.
6. The method of item 5, wherein the patient participates in at least three psychological support sessions before administration of the 5MeODMT.
7. The method of item 6, wherein the patient participates in three psychological support sessions, wherein these sessions take place 7 days, 4 days and 1 day before the administration of the 5MeODMT.
8. The method of any one of items 5 to 7, wherein the psychological support sessions are 60-90 minutes in length.
9. The method of any one of items 5 to 8, wherein at least one therapeutic intention is discussed during the psychological support session.
10. The method of any one of items 5 to 9, wherein self-directed inquiry and experiential processing are practiced during the psychological support session.
11. The method of any one of items 1 to 10, wherein the patient participates in at least one psychological support session after administration of the 5MeODMT.
12. The method of item 11, wherein the patient participates in at least three psychological support sessions after administration of the 5MeODMT.

13. The method of item 11 or item 12, wherein the patient participates in three psychological support sessions, wherein these sessions take place 1 day, 4 days and 7 days after the administration of the 5MeODMT.
14. The method of any one of items 11 to 13, wherein the psychological support sessions are 60-90 minutes in length.
15. The method of any one of items 1 to 14, wherein the 5MeODMT is administered to the patient in a room with a substantially non-clinical appearance.
16. The method of item 15, wherein the room comprises soft furniture.
17. The method of item 15 or 16, wherein the room is decorated using muted colours.
18. The method of any one of items 15 to 17, wherein the room comprises a high-resolution sound system.
19. The method of any one of items 15 to 18 wherein the room comprises food and drink for the patient and therapist.
20. The method of any one of items 15 to 19 wherein the room comprises an approved safe for storing 5MeODMT.
21. The method of any one of items 15 to 20 wherein the room is insulated such that the patient is shielded from sights and sounds of the world beyond the room.
22. The method of any one of items 15 to 21 wherein the room does not contain any artwork or decoration with any specific religious iconography, ideological connotation, or other such artwork or decoration which may evoke negative emotions in a patient.
23. The method of any one of items 15 to 22, wherein the room comprises a bed or a couch.
24. The method of item 23, wherein the patient lies in the bed or on the couch for approximately 0.5-8 hours, or a substantial fraction thereof, after administration of the 5MeODMT.
25. The method of any one of items 1 to 24, wherein the patient listens to music for approximately 0.5-8 hours, or a substantial fraction thereof, after administration of the 5MeODMT.
26. The method of any one of items 1 to 25, wherein the patient wears an eye mask for approximately 0.5-8 hours, or a substantial fraction thereof, after administration of the 5MeODMT.
27. The method of any one of items 1 to 26, wherein a therapist provides psychological support to the patient for approximately 0.5-8 hours after administration of the 5MeODMT
28. The method of any one of items 1 to 27, wherein the therapist uses guided imagery and/or breathing exercises to calm the patient and/or focus the patient's attention.
29. The method of any one of items 1 to 28, wherein the therapist provides reassuring physical contact with the patient.
30. The method of item 29, wherein the therapist holds the hand, arm, or shoulder of the patient.
31. The method of any one of items 1 to 30, wherein the therapist encourages the patient to perform self-directed inquiry and experiential processing.
32. The method of item 31, wherein the therapist reminds the patient of at least one therapeutic intention.
33. The method of any one of items 1 to 32, wherein the therapist counsels the patient to do one or more of the following:
(1) to accept feelings of anxiety,
(2) to allow the experience to unfold naturally,
(3) to avoid psychologically resisting the experience,
(4) to relax, and/or
(5) to explore the patient's own mental space.
34. The method of any one of items 1 to 33, wherein the therapist does not initiate conversation with the patient.
35. The method of item 34, wherein the therapist responds to the patient if the patient initiates conversation.
36. The method of any one of items 5 to 35, wherein psychological support is provided remotely to the patient.
37. The method of item 36, wherein the psychological support is provided via a digital or electronic system.
38. The method of item 37, wherein the digital or electronic system is a mobile phone app.
39. The method of item 38, wherein the digital or electronic system is a website.

Example 21: Study 5MEO-TOX-PK-DOG

The objective of this toxicokinetic study was to assess and compare the toxicokinetic profile of the test items, 5MeODMT-HCl (in a vehicle of 0.1% metolose, Group 2) and 5MeODMT-benzoate (in a vehicle of 0.2% metolose+ 0.01% BZK, Group 4).

Figure 19:
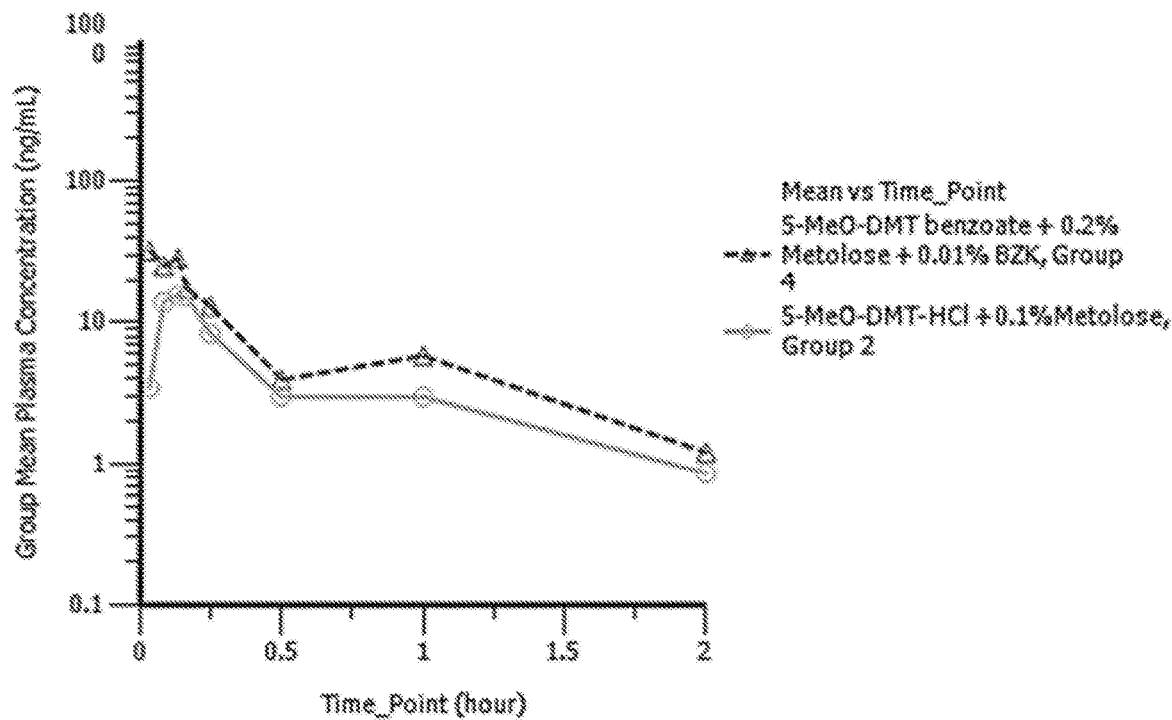
FIG. 19 shows 5MeODMT Group Mean Plasma Concentration (ng/mL) in Male Beagle Dogs—Group 2 (HCl salt) and Group 4 (benzoate salt)—Dose Level (0.4 mg/kg); wherein the Mean Plasma Concentration of Groups 2 and 4 are substantially the same with dose time.

On day 1, the vehicle or active test item formulations were administered to male Beagle dogs intranasally, at a dose level of 0.4 mg/kg in the active groups (corresponding to freebase). Following administration, a series of blood samples was collected from each dog at the following time points: pre-dose (0), 2, 5, 8, 10, 15, 30 and 60 minutes, and 2- and 8-hours post-dose. Plasma samples were analysed for quantification of concentration of 5MeODMT in each sample using a validated method 5MeODMT was not detected in any of the samples collected from the control animals on Day 1 (not shown). Peak plasma exposure levels (Cmax) were reported at 16.4 ng/mL and 35.4 ng/mL, for groups 2 and 4, respectively (see table below). FIG. 19 presents the time-course plot of mean plasma concentrations, which shows a broadly comparable TK profile between the HCl and benzoate salt formulations.

| Mean $C_{max}$ values for 5MeODMT in groups 2 and 4 on day 1 | | | | |
|---|---|---|---|---|
| Group Designation | Day | Dose Level (mg/kg) | $C_{max}$ (ng/mL) Mean | SE | N |
| Group 2 | | | | | |
| 5MeODMT-HCl + 0.1% Metolose | 1 | 0.4 | 16.4 | 1.37 | 3 |
| Group 4 | | | | | |
| 5MeODMT benzoate + 0.2% Metolose + 0.01% BZK | 1 | 0.4 | 35.4 | 16.6 | 3 |

See also FIG. 19 which shows 5MeODMT Group Mean Plasma Concentration (ng/mL) in Male Beagle Dogs— Group 2 (the 5MEODMT HCl salt formulation) and Group 4 (the 5MEODMT benzoate salt formulation)—Dose Level (0.4 mg/kg); wherein the Mean Plasma Concentration of Groups 2 and 4 are substantially the same with dose time.

Example 22: Further Embodiments

In one embodiment, there is provided a polymorph of 5MeODMT benzoate as characterised by an XRPD pattern as substantially illustrated in any one of the Figures or as previously or subsequently described.

In one embodiment, there is provided a polymorph of 5MeODMT benzoate as characterised by one or more peaks in an XRPD diffractogram as substantially illustrated in any one of the Figures or as previously or subsequently described.

In one embodiment, there is provided a polymorph of 5MeODMT benzoate as characterised by one or more endothermic events in a DSC thermograph as substantially illustrated in any one of the Figures or as previously or subsequently described.

In one embodiment, there is provided a polymorph of 5MeODMT benzoate as characterised by TGA thermograph as substantially illustrated in any one of the Figures or as previously or subsequently described.

Herein disclosed is the use of a composition as herein described for the manufacture of a medicament for the treatment of any one of: conditions caused by dysfunctions of the central nervous system, conditions caused by dysfunctions of the peripheral nervous system, conditions benefiting from sleep regulation (such as insomnia), conditions benefiting from analgesics (such as chronic pain), migraines, trigeminal autonomic cephalgias (such as short-lasting unilateral neuralgiform headache with conjunctival injection and tearing (SUNCT), and short-lasting neuralgiform headaches with cranial autonomic symptoms (SUNA)), conditions benefiting from neurogenesis (such as stroke, traumatic brain injury, Parkinson's dementia), conditions benefiting from anti-inflammatory treatment, depression, treatment resistant depression, anxiety, substance use disorder, addictive disorder, gambling disorder, eating disorders, obsessive-compulsive disorders, or body dysmorphic disorders.

Herein disclosed is a method of treating any one of: conditions caused by dysfunctions of the central nervous system, conditions caused by dysfunctions of the peripheral nervous system, conditions benefiting from sleep regulation (such as insomnia), conditions benefiting from analgesics (such as chronic pain), migraines, trigeminal autonomic cephalgias (such as short-lasting unilateral neuralgiform headache with conjunctival injection and tearing (SUNCT), and short-lasting neuralgiform headaches with cranial autonomic symptoms (SUNA)), conditions benefiting from neurogenesis (such as stroke, traumatic brain injury, Parkinson's dementia), conditions benefiting from anti-inflammatory treatment, depression, treatment resistant depression, anxiety, substance use disorder, addictive disorder, gambling disorder, eating disorders, obsessive-compulsive disorders, or body dysmorphic in a patient by the administration of a composition as described herein.

The invention claimed is:

1. A method of treatment of a patient, the method comprising administering crystalline 5-methoxy-N,N-dimethyltryptamine (5-MeO-DMT)hydrochloride to the patient, wherein the crystalline 5-MeO-DMT hydrochloride is characterized by peaks in an X-ray powder diffraction (XRPD) diffractogram at 2θ values of 9.2°±0.1°, 12.2°±0.1°, 14.1°±0.1°, 15.0°±0.1°, 18.5°±0.1°, and 19.5°±0.1°, as measured using an X-ray wavelength of 1.5406 Å, wherein the patient has depression, an eating disorder, a substance use disorder, an addictive disorder, an obsessive-compulsive disorder, a body dysmorphic disorder, a post-traumatic stress disorder, or anxiety.

2. The method of claim 1, wherein the patient has depression.

3. The method of claim 2, wherein the patient has treatment-resistant depression.

4. The method of claim 1, wherein the patient has an eating disorder or a substance use disorder.

5. The method of claim 1, wherein the patient has an addictive disorder.

6. The method of claim 1, wherein the patient has an obsessive-compulsive disorder.

7. The method of claim 1, wherein the patient has a body dysmorphic disorder.

8. The method of claim 1, wherein the patient has anxiety.

9. The method of claim 1, wherein the crystalline 5-MeO-DMT hydrochloride is administered by inhalation via a reservoir dry powder inhaler, a unit dose dry powder inhaler, a pre-metered multi-dose dry powder inhaler, or a pressurized metered dose inhaler.

10. The method of claim 1, wherein the crystalline 5-MeO-DMT hydrochloride is administered orally, buccally, sublingually, labially, by injection, or as a suppository.

11. The method of claim 9, wherein the crystalline 5-MeO-DMT hydrochloride is administered one or more times per year.

12. The method of claim 11, wherein the crystalline 5-MeO-DMT hydrochloride is administered one or more times a month.

13. The method of claim 12, wherein the crystalline 5-MeO-DMT hydrochloride is administered one or more times a week.

14. The method of claim 9, wherein the crystalline 5-MeO-DMT hydrochloride is administered alongside psychotherapy.

15. The method of claim 1, wherein 100 mg of the crystalline 5-MeO-DMT hydrochloride is administered.

16. The method of claim 1, wherein 50 mg of the crystalline 5-MeO-DMT hydrochloride is administered.

17. The method of claim 1, wherein 25 mg of the crystalline 5-MeO-DMT hydrochloride is administered.

18. The method of claim 1, wherein 10 mg of the crystalline 5-MeO-DMT hydrochloride is administered.

19. The method of claim 1, wherein 5 mg of the crystalline 5-MeO-DMT hydrochloride is administered.

* * * * *